(12) United States Patent
Smith et al.

(10) Patent No.: US 7,132,248 B2
(45) Date of Patent: Nov. 7, 2006

(54) USES OF GALANIN GALR2 RECEPTORS

(75) Inventors: Kelli E. Smith, Wayne, NJ (US); David Linemeyer, Guilford, CT (US); Christophe P. G. Gerald, Ridgewood, NJ (US); Theresa Branchek, Teaneck, NJ (US); Richard L. Weinshank, Teaneck, NJ (US); Carlos Forray, Paramus, NJ (US)

(73) Assignee: H. Lundbeck A/S, Valby-Copenhagen (DK)

( * ) Notice: Subject to any disclaimer, the term of this patent is extended or adjusted under 35 U.S.C. 154(b) by 716 days.

(21) Appl. No.: 10/285,019

(22) Filed: Oct. 31, 2002

(65) Prior Publication Data

US 2003/0215823 A1    Nov. 20, 2003

Related U.S. Application Data

(63) Continuation of application No. 08/899,112, filed on Jul. 23, 1997, now Pat. No. 6,586,191, which is a continuation-in-part of application No. PCT/US97/01301, filed on Jan. 24, 1997, which is a continuation-in-part of application No. 08/721,837, filed on Sep. 27, 1996, now abandoned, which is a continuation-in-part of application No. 08/626,685, filed on Apr. 1, 1996, now Pat. No. 5,972,624, and a continuation-in-part of application No. 08/626,046, filed on Apr. 1, 1996, now abandoned, and a continuation-in-part of application No. 08/590,494, filed on Jan. 24, 1996, now abandoned, and a continuation-in-part of application No. 08/590,494, filed on Jan. 24, 1996, now abandoned.

(51) Int. Cl.
*G01N 33/53* (2006.01)

(52) U.S. Cl. ...................... 435/7.2; 435/69.1

(58) Field of Classification Search ............ None
See application file for complete search history.

(56) References Cited

U.S. PATENT DOCUMENTS

| | | | |
|---|---|---|---|
| 5,290,808 A | 3/1994 | Sofia et al. | |
| 5,436,128 A | 7/1995 | Harpold et al. | |
| 5,436,155 A | 7/1995 | Bell et al. | |
| 5,462,856 A | 10/1995 | Lerner et al. | |
| 5,508,164 A | 4/1996 | Kausch et al. | |
| 5,567,714 A | 10/1996 | Bruns et al. | |
| 5,576,296 A | 11/1996 | Bartfai et al. | |
| 5,972,624 A | 10/1999 | Smith et al. | |

FOREIGN PATENT DOCUMENTS

| | | |
|---|---|---|
| AU | 730137 | 6/2001 |
| EP | 514361 | 11/1992 |
| EP | 711830 | 5/1996 |
| WO | WO9212997 | 8/1992 |
| WO | WO9215015 | 9/1992 |
| WO | WO9215681 | 9/1992 |
| WO | WO9522608 | 8/1995 |
| WO | WO9746681 | 12/1997 |
| WO | WO9803059 | 1/1998 |
| WO | WO9803548 | 1/1998 |
| WO | WO9829439 | 7/1998 |

OTHER PUBLICATIONS

Ahmad, A., et al., Identification and Molecular Cloning of a Novel Galanin Receptor (GALR-2) In Rat Sensory Neurons. *Soc. Neurosci. Abstr.* (1996) vol. 22, No. 3, p. 1682, Abstract No. 661.10.

Ahmad, S., et al., Molecular Cloning of a Novel, Widely Distributed Galanin Receptor Sub-Type (GALR-2). *Astra Pain Control*, (1996), poster.

Ahmad, S., et al., Molecular Cloning of a Novel, Widely Distributed Galanin Receptor Subtype (GALR2). *International Association for the Study of Pain*, IASP Press (1996) Abstract No. 81, p. 134.

Bartfai, T., et al., Galanin Receptor Ligand M40 Peptide Distinguished Between Putative Galanin-Receptor Subtypes. *PNAS (USA)* (1993) vol. 90, pp. 11287-11291.

Bouvier, M., et al., Dynamic Palmitoylation of G-Protein-Coupled Receptors in Eukaryotic Cells. *Methods in Enzymology* (1995) vol. 250, pp. 300-314.

Bowie, James U., et al., Deciphering the Message in Protein Sequences: Tolerance to Amino Acid Substitutions. *Science*, (Mar. 1990), vol. 247, pp. 1306-1310.

Burgevin, M.C., et al., Cloning Pharmacological Characterization, and Anatomical Distribution of a Rat cDNA Encoding for a Galanin Receptor. *J. Molec. Neurosci.* (1995) vol. 6, pp. 33-41.

Chen, Y., et al., Purification of a Galanin Receptor From Pig Brain. *PNAS (USA)* (1993) vol. 90, pp. 3845-3849.

Deecher, D.C., et al., Galanin Receptors in Human Basal Forebrain Differ From Receptors in the Hypothalamus: Characterization Using [$^{125}$I] Galanin (Porcine) and [$^{125}$I] Galantide. *J. Pharmocol. Exp. Ther.* (1995) vol. 275, pp. 720-727.

(Continued)

*Primary Examiner*—Michael Pak
(74) *Attorney, Agent, or Firm*—Stephen G. Kalincha

(57) ABSTRACT

This invention provides isolated nucleic acids encoding mammalian galanin receptors, isolated galanin receptor proteins, vectors comprising isolated nucleic acid encoding a mammalian galanin receptor, cells comprising such vectors, antibodies directed to a mammalian galanin receptor, nucleic acid probes useful for detecting nucleic acid encoding a mammalian galanin receptor, antisense oligonucleotides complementary to unique sequences of nucleic acid encoding a mammalian galanin receptor, nonhuman transgenic animals which express DNA encoding a normal or a mutant mammalian galanin receptor, as well as methods of determining binding of compounds to mammalian galanin receptors.

32 Claims, 29 Drawing Sheets

OTHER PUBLICATIONS

GenBank Accession No. AF 031522, Wang, S., et al., "Cloning and expressional characterization of a novel galanin receptor. Identification of a different pharmacophores within galanin for the three galanin receptor subtypes," published Jan. 27, 1998.

GenBank Accession No. RNU 94322, McKee, K.K., et al., "Molecular cloning and characterization of a new receptor for galanin," published Apr. 30, 1997.

GenBank Accession No. AF 008548, Fathi, Z., "Cloning, pharmacological characterization and distribution of a novel galanin receptor," published Jul. 8, 1997.

GenBank Accession No. AF 010318, Smith, K.E., et al., "Expression cloning of a rat hypothalamic galanin receptor coupled to phosphoinositide turnover," published Sep. 30, 1997.

GenBank Accession No. Z 82241, Connor, R., "Direct Submission," published Nov. 10, 1996.

Gu, Z. F., et al., Interaction of Galanin Fragments with Galanin Receptors on Isolated Smooth Muscle Cells From Guinea Pig Stomach: Identification of a Novel Galanin Receptor Subtype. *J. Pharmacol. Exp. Ther.* (1995) vol. 272, pp. 371-378.

Gustafson, E. et al., Distribution of a Rat Galanin Receptor mRNA in Rat Brain. *Neuroreport* (1996) vol. 7, pp. 953-957.

Habert-Ortoli, E., et al., Molecular Cloning of a Functional Human Galanin Receptor. *PNAS* (USA) (1994) vol. 91, pp. 9780-9783.

Heuillet, E., et al., The Human Galanin Receptor: Ligand Binding and Functional Characteristics in the Bowes Human Melanoma Cell Line. *Eur. J. Pharmacol.* (1994) vol. 269, pp. 139-147.

Iismaa, Tiina P., and John Shine, Galanin and Galanin Receptors. *Results and Problems in Cell Differentiation*, Springer-Verlag, New York, NY (1999), vol. 26, pp. 257-291.

Kahl, U., et al., Galanin Receptors. *DN&P* (1995) vol. 8, No. 7, pp. 404-410.

Kask K., et al., Delineation of the Peptide Binding Site of the Human Galanin Receptor. *EMBO Journal* (1996) vol. 15, No. 2, pp. 236-244.

Lorimer, D., et al., Cloning and Quantification of Galanin-1 Receptor Expression by Mucosal Cells Lining the Human Gastrointestinal Tract. *Biochem. Biophys. Res. Comm.* (1996) vol. 222, pp. 379-385.

Lorinet, A.M., et al., Galanin Receptors in Human Hypothalamus: Biochemical and Structural Analysis. *Eur. J. Pharmacol.* (1994) vol. 269, pp. 59-64.

Marieb, E.N., (1992), *Human Anatomy And Physiology*, 2$^{nd}$ Edition, Redwood City, CA, pp. 547-551.

O'Donnell, D., et al. Neuroanatomical Distribution of a Novel Rat Galanin Receptor Subtype. *Soc. Neurosci. Abstr.* (1996) vol. 22, No. 2, p. 1304, Abstract No. 517.9.

Parker, et al., Cloning and Characterization of the Rat GALR1 Galanin Receptor From Rin14B Insulinoma Cells. *Molecular Brain Research* (1995) vol. 34, No. 2, pp. 179-189.

Reerk, et al., 'Homology' in Proteins and Nucleic Acids: A Terminology Muddle and a Way Out of It. *Cell* (1987) vol. 50, p. 667.

Selve, Norma, et al., Galanin Receptor Antagonists Attenuate Spinal Antinociceptive Effects of DAMGO, Tramadol and Non-Opioid Drugs in Rats. *Brain Res.* (Oct. 7, 1996) vol. 735, No. 2, pp. 177-187.

Valkna, A., et al., Differential Regulation of Adenylate Cyclase Activity in Rat Ventral and Dorsal Hippocampus by Rat Galanin. *Neurosci. Lett.* (1995) vol. 187, pp. 75-78.

Wallace, et al., *Methods in Enzymology* (1987), pp. 432-442.

Walli, R., et al., Identification and Biochemical Characterization of the Human Brain Galanin Receptor. *J. Mol. Endocrinol.* (1994) vol. 13, pp. 347-356.

Wang, Suke, et al., Molecular Cloning and Pharmacological Characterization of a New Galanin Receptor Subtype. *Mol. Pharm.* (Sep. 1997) vol. 52, pp. 337-343.

Wang, Suke, et al., Cloning and Expressional Characterization of a Novel Galanin Receptor. *J. Biol. Chem.* (Dec. 19, 1997) vol. 272, No. 51, pp. 31949-31952.

Watson, et al., The G-Protein Linked Receptor Fact Book. Academic Press Limited (1994), San Diego, CA. pp. 2-6.

Wynick, D., et al., Characterization of a High-Affinity Galanin Receptor in the Rat Anterior Pituitary: Absence of Biological Effect and Reduced Membrane Binding of the Antagonist M15 Differentiate it From the Brain/Gut Receptor. *PNAS* (USA) (1993) vol. 90, pp. 4231-4235.

Xu, X.J., et al., New High Affinity Peptide Antagonists to the Spinal Galanin Receptor. *Br. J. Pharmacol.* (1995) vol. 116, pp. 2076-2080.

Xu, Zhi-Qing, et al., Expression of Galanin and a Galanin Receptor in Several Sensory Systems and Bone Anlage of Rat Embryos. *Proc. Natl. Acad. Sci. USA,* (Dec. 1996) vol. 93, pp. 14901-14905.

U.S. Appl. No. 08/899,112, filed on Jul. 23, 1997, Kelli E. Smith, et al.; and (Exhibit E).

Kelli E. Smith, et al., U.S. Appl. No. 09/011,553, filed Jun. 4, 1998.

FIGURE 1

```
   1 CAAGACCCGGACAGCTGCGGGAGCGGCGTCCACTTTGGTGATACCATGAATGGCTCCGGC      60
  61 AGCCAGGGCGCGGAGAACACGAGCCAGGAAGCGGTAGCGGTGGCGGCTGGCAGCCTGAGGCG   120
 121 GTCCTTGTACCCCTATTTTTCGCGCGGGCGCTCATCTTCCGTGGCACCGTGGCAACGCGCTG   180
 181 GTGCTGGCCGGTGCTGCTGCCCAGGCGGTCAGGCGGTCAGCACCACCAACCTGTTCATCCTC   240
 241 AACCTGGGCGTGGCCGACCTGTGTTCATCCTCCTGTGCTGCCTTTCCAGGCCACCATC      300
 301 TACACCCTGACGACTGGGGTTCGGCTGGTGTTCGGCTGCTCTGCAAGGCTGTTCATTTCCTCATC   360
 361 TTTCTCACTATGCACGCCAGCAGCTTCACGCTCTCCCTGGACACAGGTATCTG            420
 421 GCCATCGCCTACCCCGTCGGGGGCTAGCACTCCGAGAGTTGCGCACACCTCGAAACGCGCTGGCCGCC   480
 481 ATCGGGCTCATCTGGGGGCTAGCACTGCTCTTCCCGGGCCCTACCTGAGCTACTACCGT      540
 541 CAGTCGCAGCTGGCCAACCTGCACCTTGCGCTACCCTCTGCCGCACCAGTGCACCTGAGCGCGTCGA   600
 601 GCCATGGACCTCTGCGTACCCTTGCCGCTACCCTCTGCCGCAGTCGACTCCTCAGTCTG      660
 661 ACCTATGCGCGTAACCCCTGCCGCCAAACGCAAGTCGACACAGTGATGATCATCGTGCAGGCTCA   720
 721 GGTTCCCCAGCCGCCGCCGGATGCCCCACCAGGCCTTATCCTCTGCGTGTGGTTTGGTCGTTTCCCG   780
 781 TGCCTCTGTTGGACCTGCCACTTACGCGTTGCGCATCTCTGGTCTCCAAGCATTTCCACACCTTCCG   840
 841 CTCACGCGTGCCACTTACGCGTTGCGCATCTCTGGTCTCCGAGGCGAGTTTCCTATGCCAACTCC   900
 901 TGTGTCAACCCGTGGGCCTGCTGCGCCCCTGCCCCCGAGGCGAGCTTCGGGCCGAGTGAGCATCCTG   960
 961 ATCTGCGCGGGCCTGGAACCATAGTGCAGCATGCAGAACAGGAATCCACAGACCTGACACAGTG  1020
1021 GCGCCCTGGAACCATAGTGCAGCATGCAGAACAGGAATCCACAGACCTGACACAGTG        1080
1081 AGCGAGGCAGCCGGCCCCTTGTCCCACCACCCGCACTCCCAACTGCACAGCCTCGAGT      1140
1141 AGAACCCTGGATCCGGCTTGTTAAAGGACCAAAGGGCATCTAACAGCTTCTAG            1193
```

FIGURE 2

[Protein sequence, 372 residues, displayed in 19 blocks of 20 residues (last block 12 residues); positions numbered 1, 21, 41, 61, 81, 101, 121, 141, 161, 181, 201, 221, 241, 261, 281, 301, 321, 341, 361 (start) through 20, 40, 60, 80, 100, 120, 140, 160, 180, 200, 220, 240, 260, 280, 300, 320, 340, 360, 372 (end).]

FIGURE 3C

```
 414  GTGAGTGAACATCGGAGAACTATTGTATCTGAGATAGGGGCTTGGGCTGGAGTCACTACA   473
 474  CAGGGGATCCAGAAGGCATGAGCAGAGAACACTGAAATTACAAAGTGGCCTG           533
 534  AGGCCGTGAAACGCAAGGGGAGGAGATTAAGACTCAGTGACTGAGAGTGTCTAAGTCG     593
 594  ATGGGAGAAATCGGGTCTCTCTCGGGGTCCTCGCATTATTACTGCTTGAGTTAAATGTCTCTG 653
 654  TGAAACATTGCAGTTCTGCAGGCCAGAGTTGGCAGGAAAAGTAACTCGCCAGTGTTCAGAT  713
 714  GCTGTTTGAGAGCTGCAGAGAAGCATCTGCTTCTTAGCACCAAGCTCAGCACCTGGGGCG   763
 774  TTGTCCGGCGCCTTAGGCTTAGGACTGGGCTGTGTGCTGTTAAGACCCTCCAAGTCC      833
 834  AACGGAGTGTAAGCGAGGGCTCCTAGCTGACACCCAGAGCCCTCCAGGCCAAGGCTCCCC  893
 894  TCACCGAGATGCCCAGCTGGTTTTATGCTCCTTCCATAGGTAAAGGACCCTGGTGACCCTTAGT 953
 954  CCAGTATGCCCGGAGGGATCTTGACTGGACATTCCCACAGAAGACTGAATCCTGGTCTGAAGAGAGCGGTGGTC 1013
1014  TCCCTGCCCTTTCACATCACTTGGACATTCCCACAGAAGACTGAATCCTGGTCTGAAGAGAGCGGTGGTC  1073
1074  CTTATTCCTCTGGTTTCCACTGAGTGCAACATGTGCGTCCTGAGTACGCTGGAGGAC     1133
1134  TCACAAAATTTCAGCTTTCTTTAGGAGTTTCCTTGCTGTAGTTTGACCCAAGTCTTCTCC  1193
1194  AGTTTCTGTCAGAACCTCAGGCATGAGGGGATCTGCCTCCCCTGGTTGTCACCAGAGGAT  1253
1254  AACAATCACTGCCCCCAGAAATCCAGACAGATTCTACAACTTTTAGTCTTCGGTGTTTTG  1313
1314  GGGGTGCCCCTTCACGTGGAGTAGGTCGGTGGCCACATTCCCAGGAGTGACAATAGCCTA  1373
1374  GCAGTGAATCCTCTCGCTTAGCTGATGCCCCCCACTGTCCCCACAG                1420
```

FIGURE 10

| | | |
|---|---|---|
| -100 | AGTCGCACTAGGAGTTGCAGCGGCCCGCAGCCCCGGGAGCTTCCCGCTCGCGGAGACCCAG | -41 |
| -40 | ACGGCTGCAGGAGCCCGGGCAGCCTCGGGGTCAGCGGCACCATGAACGTCTCGGGCTGCC | 19 |
| 20 | CAGGGGCCGGGAACGCGGAGCCAGGGCGGGGGAGGCTGGCACCCCGAGGCGGTCA | 79 |
| 80 | TCGTGCCCCTGCTCTTCGCGCTCATCTTCCTGGGCACCGTGGGCAACACGCTGGTGC | 139 |
| 140 | TGGCGGTGCTGCTGCGCGGCCACCTGTGTTTCATCCTGTGCTGCCCCTTCCAGGCCACCATCTACA | 199 |
| 200 | TGGGCGTGGCCGACTGGGTGTTCGGCTCGCTGGCACTTCCTGCAAGGCGTGCACTTCCTCATCTTCC | 259 |
| 260 | CCCTGGACGGCTGGGTTCTCCTGCTCGTGTGCAAGGCGTGCACTTCTGGACAGGTATCTGGCCA | 319 |
| 320 | TCACCATGCACGCCAGCTTCCCGCTGCTCCCGAAACGCGCTGGCAGCTACTACCGCCAGT | 379 |
| 380 | TCCGCTACCCGCTGCACTCCCGCTGTCGCCTCTGCTCCCGAGCCTGACCCTGGAGCGCCCA | 439 |
| 440 | GGCTCATCTGGGGCTGTGCGTCGCCATCCCGCGTGTTCCTGCTACCTGTGTGTCTCGCCCTGACCT | 499 |
| 500 | CGCAGCTGGCCAACCTGCACCTTCGTCTTCAGCTACCTTGCGCTACCTGGCCCGGGCTCGGGTG | 559 |
| 560 | TGGACATCTGCACGCTTTACGCGTCTTCCTCAGCTGCTTCCTGACCCCGGTGCCGGGCTCGGGGTG | 619 |
| 620 | ACGCGCGCACCTTGCGCAAGCGCACCAAGGTGACACGCATGATCCTCGTGGCCGCGCTCTTCTGCC | 679 |
| 680 | CCCGCCGCCAAGCGCCCCACCACGCGCTCATCCTCTGCGTGGTTCGGCCAGTTCCCGCTCA | 739 |
| 740 | TCTGCTGGATGCCCCACTTATGCGCCGCGCTCATCCTGGTCTCTCGCACCTGTTCCGCAACTCCTGCG | 799 |
| 800 | CGCGGCCACTTAGCGCGCTATGCGCGCTTCGCTCACCTGTCTCCAAGCACTTCCGCAAGGCTTCCTGCACGATCT | 859 |
| 860 | TCAACCCCATCGTTTACGCGTCTTGGGCCGTGTCCCAGGCCGAGCCTGTTGGAGCGCGAGCATGAGCG | 919 |
| 920 | GCGCGGCCTGCTGTGCTGGGCCGTGGAGCGCGTGTGAGCGCGAGTCGCCCGGCGCGCGC | 979 |
| 980 | GGGGCACCCACAGTGGGGGCCCTTCGTCCCTGCCCAGGCCCATGGCTTCCAGGCCGACCTGTTGCACATGAGCG | 1039 |
| 1040 | AGGCGGGGCCCGCCCCGTCCTGGCCAGGGCCAAAGGCCTGGGATGTCACAGAGTTCACAGAGTTGAGTCATTGTGG | 1099 |
| 1100 | GTCCTGCCCCGGCCCCTGGCCAGGGCGCGCTGGGATGTCACAGAGTTCACAGAGTTGAGTCATTGTGG | 1159 |
| 1160 | CCTGAAAGCACTTAGCGGGCGCGCTGTGTTAATAAACGCACAAACCATTTCA | 1219 |
| 1220 | CGTGGGAGAGCTTTGCCTGTGTTAATAAACGCACAAACCATTTCA | 1264 |

```
 369 GTGAGCCAGCGCCTTGGCCTCCCTGGGAGATGGGCATCCACGCGGGGATGGAGCGGGAG  428
 429 GCGGGACTGGGACCAAGAAGGACGCGCAGAGTGGGACAGGAGACACTAAGAAGGCAGTGG  488
 489 AAGACAAGCGGGCGGAGGAGGAAAAAGAGGAATAAGAATGGGGACCGTGGTGTCCCT     548
 549 CGGTTAGATGCGTCCTGGGCCTGGAAGCCTGGAGAATGTGGCTCTCCAGCGCCGCCCGT   608
 609 GCCTGACAACGCGCAGCGTTTCCCAGTACGACGCGTTTGTGCGTTCATCTCGCTTGAG    668
 669 CTTAATGCCCTCCGTGAGGGTGGGATAGGACAAAGTGCCAATATACAGAAGAGTTGAGT   728
 729 TCCTAAGTAACTCGCTCAGAGTCGCCAGCCAGGGATCGGGTGCGTGAAGTGACCGTCTGT 788
 789 CTCCTGCAGCCAACTTCAGGCGTCCAGCGCCCTCGCTCCAGCCGGTCCTTGCAAGGATCCACTCC 848
 849 TTGGTGCAGCTGGCTCAGTCAGGCCGTGTGGATCTTGGGTCCCTAGTCCAGTCCTGCCTCTCG 908
 909 GGAGTCCCAGCGAGCCGAGCGTGCCTAAAGTCCCTAGTCAAGAGTTCCAAAACAAGTCGGGCCGGGAGAGAGCGT 968
 969 CCTCCAAACAAAAACAAAATCAAAAATCCAAGAGAGCGAGAGAGACGCACATTCGGGAGAGCGC 1028
1029 GCCCTGGGGTTCTTCCTCCCCAGCGTGGAGGATGGTTCCTGGGAGGAGACACTCCGGTAT 1088
1089 GGACTCAGTGGAGCTTGAAAGGACACTGGGAAGGCCAGACTGCCCCCACACCTCCT    1148
1149 TTCCCTCCTCAGTCCTCCATCCCTGAGCGCGAAGTGCGTTGGTTCCGAGCGCGTGGGATCCACAAAGCTCG 1208
1209 GTAGCCACTGAGCGCCAGGAATCCCCGAGAAATTAACTGTCCCTGCCAACATGTCTTCTCCAGG 1268
1269 CATTCTCTCAGGAATCCCGAGAAATTAACTGTCCCTGCCAACATGTCTTCTCCAGG     1328
1329 CTGTCTGCTAGAGCCTCAGGCCTCCGCGCCCCCTCCCCGCCACCGTCACCAGTGGGT    1388
1389 AGTCACAGCCCTCCGGAGCCCATAGCCGGTTCTGCAGTGTTCTCCAACCTTTAGTCTTCAGTGGCTTTGG 1448
1449 GGTGCCCTCTCAGTGGAGACTGTGGTTGCAGTGCCCCCATTCCCGGGCAGCGGGAGAATGGCTTGA 1508
1509 AGGCACACCTTTCCTGCTGCCGGCCCCTCACCGCCGAGCCTGAGTGTCCGCTGAGTGTCTGGGA 1568
1569 CACGCTGGAGCCCCCACCATGAATGCGCTAAGGACCTTCCTCCACCCCTCTGTGT      1628
1629 GCGGTGTAACCATGAATGCGCTAAGGACCTTCCTCGAGAGCAGCCTTGGGACCGAGGTGCAGGG 1688
1689 GTCGCGGCCCTCCAGCAGCATGAATGTGCCCGCTCAGCGACGTCCCTTCCCGGTCTGACC 1748
1749 GCAG                                                         1752
```

Figure 15A

```
rGALR2   . . . . . . M N G S G S Q G A E N T S Q E G G S G           19
hGALR2   . . . . . . M N V S G C P G A G N A S Q A G G G G           19
rGALR1   . . M E L A P V N L S E G N G S D P E P P A E P R P L       25 rGALR2   . G W Q P E A V L V P L F F A L I F L V G T V G N           43
hGALR2   . G W H P E A V I V P L L F A L I F L V G T V G N           43
rGALR1   F G I G V E N F I T L V V F G L I F A M G V L G N           50 rGALR2   A L V L A V L L R G . . G Q A V S T T N L F I L N           66
hGALR2   T L V L A V L L R G . . G Q A V S T T N L F I L N           66
rGALR1   S L V I T V L A R S K P G K P R S T T N L F I L N           75 rGALR2   L G V A D L C F I L C C V P F Q A T I Y T L D D W           91
hGALR2   L G V A D L C F I L C C V P F Q A T I Y T L D G W           91
rGALR1   L S I A D L A Y L L F C I P F Q A T V Y A L P T W          100
```

Figure 15B

```
                              III
rGALR2  V F G S L L C K A V H F L I F L T M H A S S F T L   116
hGALR2  V F G S L L C K A V H F L I F L T M H A S S F T L   116
rGALR1  V L G A F I C K F I H Y F F T V S M L V S I F T L   125 rGALR2  A A V S L D R Y L A I R Y P L H S R E L R T P R N   141
hGALR2  A A V S L D R Y L A I R Y P L H S R E L R T P R N   141
rGALR1  A A M S V D R Y V A I V H S R R S S S L R V S R N   150
              IV
rGALR2  A L A A I G L I W G L A L L F S G P Y L S Y Y R Q   166
hGALR2  A L A A I G L I W G L S L L F S G P Y L S Y Y R Q   166
rGALR1  A L L G V G F I W A L S I A M A S P V A Y Y Q R L   175 rGALR2  S Q L · A N L T V C H P A W S A P · R R R A M D L   189
hGALR2  S Q L · A N L T V C H P A W S A P · R R R A M D I   189
rGALR1  F H R D S N Q T F C W E H W P N Q L H K K A Y V V   200
```

Figure 15C

```
                           V
rGALR2    C T F V F S Y L L P V L V L S L T Y A R T L R Y L    214
hGALR2    C T F V F S Y L L P V L V L G L T Y A R T L R Y L    214
rGALR1    C T F V F G Y L L P L L L I C F C Y A K V L N H L    225 rGALR2    W R T V D P V T A G S G S Q R A K R K V T R M I I    239
hGALR2    W R A V D P V A A G S G A R R A K R K V T R M I L    239
rGALR1    H K K L K N M S K K S E A · S K K T A Q T V L        248

VI
rGALR2    I V A V L F C L C W M P H H A L I L C V W F G R F    264
hGALR2    I V A A L F C L C W M P H H A L I L C V W F G Q F    264
rGALR1    V V V V F G I S W L P H H V I H L W A E F G A F      273

VII
rGALR2    P L T R A T Y A L R I L S H L V S Y A N S C V N P    289
hGALR2    P L T R A T Y A L R I L S H L V S Y A N S C V N P    289
rGALR1    P L T P A S F F F R I T A H C L A Y S N S S V N P    298
```

Figure 15D

```
rGALR2   I V Y A L V S K H F R K G F R K I C A G L L R P A   314
hGALR2   I V Y A L V S K H F R K G F R T I C A G L L G R A   314
rGALR1   I I Y A F L S E N F R K A Y K Q V F K C R V C N E   223 rGALR2   P R R A S G R V S I L A P G N H S G S M L E Q E S   339
hGALR2   P G R A S G R V C A A A A R G T H S G V L E R E S   339
rGALR1   S P H G D A K . . . . . . . E K N R I D T P P S   340 rGALR2   T D L T Q V S E A A A G P L V P P P A . . . . L   358
hGALR2   S D L L H M S E A A A G A L R P C P G A S Q P C I L   364
rGALR1   T N C T H V . . . . . . . . . . . . . . . . .   346 rGALR2   P N C T A S S R . . . . T L D P A C   372
hGALR2   E P C P G P S W Q G P K A G D S I L T V D V A   387
```

USES OF GALANIN GALR2 RECEPTORS

This application is a continuation of U.S. Ser. No. 08/899,112, filed on Jul. 23, 1997, now U.S. Pat. No. 6,586,191, which is a continuation-in-part of PCT International Application No. PCT/US97/01301, filed Jan. 24, 1997, which claims priority and is a continuation-in-part both of U.S. Ser. No. 08/721,837, filed Sep. 27, 1996, now abandoned, which was a continuation-in-part of U.S. Ser. No. 08/626,685, filed Apr. 1, 1996, now U.S. Pat. No. 5,972,624, issued Oct. 26, 1999, a continuation-in-part of U.S. Ser. No. 08/590,494, filed Jan. 24, 1996, now abandoned, and of U.S. Ser. No. 08/626,046, filed Apr. 1, 1996, now abandoned, a continuation-in-part of U.S. Ser. No. 08/590,494, filed Jan. 24, 1996, now abandoned, the contents of all of which are hereby incorporated by reference.

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

The neuropeptide galanin and its receptors hold great promise as targets for the development of novel therapeutic agents. Galanin is widely distributed throughout the peripheral and central nervous systems and is associated with the regulation of processes such as somatosensory transmission, smooth muscle contractility, hormone release, and feeding (for review, see Bartfai et al., 1993). In the periphery galanin is found in the adrenal medulla, uterus, gastrointestinal tract, dorsal root ganglia (DRG), and sympathetic neurons. Galanin released from sympathetic nerve terminals in the pancreas is a potent regulator of insulin release in several species (Ahren and Lindskog, 1992; Boyle et al., 1994), suggesting a potential role for galanin in the etiology or treatment of diabetes. High levels of galanin are observed in human and rat anterior pituitary where galanin mRNA levels are potently upregulated by estrogen (Vrontakis et al., 1987; Kaplan et al., 1988). The presence of galanin in the hypothalamic-pituitary-adrenal axis coupled with its potent hormonal effects has led to the suggestion that galanin may play an integral role in the hormonal response to stress (Bartfai et al., 1993).

Within the CNS galanin-containing cell bodies are found in the hypothalamus, hippocampus, amygdala, basal forebrain, brainstem nuclei, and spinal cord, with highest concentrations of galanin in the hypothalamus and pituitary (Skofitsch and Jacobowitz, 1985; Bennet et al., 1991; Merchenthaler et al., 1993). The distribution of galanin receptors in the CNS generally complements that of galanin peptide, with high levels of galanin binding observed in the hypothalamus, amygdala, hippocampus, brainstem and dorsal spinal cord (Skofitsch et al., 1986; Merchenthaler et al., 1993; see Bartfai et al., 1993) Accordingly, agents modulating the activity of galanin receptors would have multiple potential therapeutic applications in the CNS. One of the most important of these is the regulation of food intake. Galanin injected into the paraventricular nucleus (PVN) of the hypothalamus stimulates feeding in satiated rats (Kyrkouli et al., 1990), an effect which is blocked by the peptide galanin antagonist M40 (Crawley et al., 1993). In freely feeding rats, PVN injection of galanin preferentially stimulates fat-preferring feeding (Tempel et al., 1988); importantly, the galanin antagonist M40 administered alone decreases overall fat intake (Leibowitz and Kim, 1992). These data indicate that specific receptors in the hypothalamus mediate the effects of galanin on feeding behavior, and further suggest that agents acting at hypothalamic galanin receptors may be therapeutically useful in the treatment of human eating disorders.

Galanin receptors elsewhere in the CNS may also serve as therapeutic targets. In the spinal cord galanin is released from the terminals of sensory neurons as well as spinal interneurons and appears to play a role in the regulation of pain threshold (Wiesenfeld-Hallin et al., 1992). Intrathecal galanin potentiates the anti-nociceptive effects of morphine in rats and produces analgesia when administered alone (Wiesenfeld-Hallin et al., 1993; Post et al., 1988); galanin receptor agonists may therefore be useful as analgesic agents in the spinal cord. Galanin may also play a role in the development of Alzheimer's disease. In the hippocampus galanin inhibits both the release (Fisone et al., 1987) and efficacy (Palazzi et al., 1988) of acetylcholine, causing an impairment of cognitive functions (Sundström et al., 1988). Autopsy samples from humans afflicted with Alzheimer's disease reveal a galaninergic hyperinnervation of the nucleus basalis (Chan-Palay, 1988), suggesting a role for galanin in the impaired cognition characterizing Alzheimer's disease. Together these data suggest that a galanin antagonist may be effective in ameliorating the symptoms of Alzheimer's disease (see Crawley, 1993). This hypothesis is supported by the report that intraventricular administration of the peptide galanin antagonist M35 improves cognitive performance in rats (Ögren et al., 1992). Human galanin receptors thus provide targets for therapeutic intervention in multiple CNS disorders.

High-affinity galanin binding sites have been characterized in brain, spinal cord, pancreatic islets and cell lines, and gastrointestinal smooth muscle in several mammalian species, and all show similar affinity for $^{125}$I-porcine galanin (~0.5–1 nM). Nevertheless, recent in vitro and in vivo pharmacological studies in which fragments and analogues of galanin were used suggest the existence of multiple galanin receptor subtypes. For example, a galanin binding site in guinea pig stomach has been reported that exhibits high affinity for porcine galanin (3–29) (Gu, et al. 1995), which is inactive at CNS galanin receptors. The chimeric galanin analogue M15 (galantide) acts as antagonist at CNS galanin receptors (Bartfai et al., 1991) but as a full agonist in gastrointestinal smooth muscle (Gu et al., 1993). Similarly, the galanin-receptor ligand M40 acts as a weak agonist in RINm5F insulinoma cells and a full antagonist in brain (Bartfai et al, 1993a). The pharmacological profile of galanin receptors in RINm5F cells can be further distinguished from those in brain by the differential affinities of [D-Tyr$^2$]- and [D-Phe$^2$]-galanin analogues (Lagny-Pourmir et al., 1989). The chimeric galanin analogue M35 displaces $^{125}$I-galanin binding to RINm5F membranes in a biphasic manner, suggesting the presence of multiple galanin receptor subtypes, in this cell line (Gregersen et al., 1993).

Multiple galanin receptor subtypes may also co-exist within the CNS. Galanin receptors in the dorsal hippocampus exhibit high affinity for Gal (1–15) but not for Gal (1–29) (Hedlund et al., 1992), suggesting that endogenous proteolytic processing may release bioactive fragments of galanin to act at distinct receptors. The rat pituitary exhibits high-affinity binding for $^{125}$I-Bolton and Hunter (N-terminus)-labeled galanin (1–29) but not for [$^{125}$I]Tyr$^{26}$-porcine galanin (Wynick et al., 1993), suggesting that the pituitary galanin receptor is a C-terminus-preferring subtype. Spinal cord galanin binding sites, while similar to those in brain, show an affinity for the chimeric peptide antagonist M35 intermediate between the brain and smooth muscle (Bartfai et al., 1991), raising the possibility of further heterogeneity.

A galanin receptor cDNA was recently isolated by expression cloning from a human Bowes melanoma cell line (Habert-Ortoli et al., 1994). The pharmacological profile exhibited by this receptor is similar to that observed in brain and pancreas, and on that basis the receptor has been termed GALR1. The cloned human GALR1 receptor binds native human, porcine and rat galanin with ~1 nM affinity ($K_i$ vs. $^{125}$I-galanin) and porcine galanin 1–16 at a slightly lower affinity (~5nM). Porcine galanin, 3–29 does not bind to the receptor. The GALR1 receptor appears to couple to inhibition of adenylate cyclase, with half-maximal inhibition of forskolin-stimulated cAMP production by 1 nM galanin, and maximal inhibition occurring at about 1 µM.

Recently the rat homologue of GALR1 was cloned from the RIN14B pancreatic cell line (Burgevin, et al., 1995; Parker et al., 1995; Smith et al., in preparation). The pharmacological data reported to date do not suggest substantial differences between the pharmacologic properties of the rat and human GALR1 receptors. Localization studies reveal GALR1 mRNA in rat hypothalamus, ventral hippocampus, brainstem, and spinal cord (Gustafson et al., 1996), regions consistent with roles for galanin in feeding, cognition, and pain transmission. However, GALR1 appears to be distinct from the pituitary and hippocampal receptor subtypes described above.

The indication of multiple galanin receptor subtypes within the brain underscores the importance of defining galanin receptor heterogeneity at the molecular level in order to develop specific therapeutic agents for CNS disorders. Pharmacological tools capable of distinguishing galanin receptor subtypes in tissue preparations are only beginning to appear. Several high-affinity peptide-based galanin antagonists have been developed and are proving useful in probing the functions of galanin receptors (see Bartfai et al., 1993), but their peptide character precludes practical use as therapeutic agents. In light of galanin's multiple neuroendocrine roles, therapeutic agents targeting a specific disorder must be selective for the appropriate receptor subtype to minimize side effects.

Accordingly, the cloning of the entire family of galanin receptors for use in target-based drug design programs has been endeavored. The identification of non-peptide agents acting selectively only at specific galanin receptors will be greatly facilitated by the cloning, expression, and characterization of the galanin receptor family.

The isolation by expression cloning of a novel galanin receptor from a rat hypothalamic cDNA library, as well as its pharmacological characterization in a heterologous expression system is now reported. The data provided demonstrate for the first time the existence of a new galanin receptor subtype, from now on referred to as the GALR2 subtype, or simply, "GALR2." The cloning of the human homolog of the rat GALR2 receptor is also reported. This discovery provides a novel approach, through the use of heterologous expression systems, to develop subtype selective, high-affinity non-peptide compounds that could serve as therapeutic agents for eating disorders, diabetes, pain, depression, ischemia, and Alzheimer's disease. The presence of both GALR1 and GALR2 in rat hypothalamus suggests that multiple galanin receptors may be involved in the regulation of feeding. Pathophysiological disorders proposed to be linked to galanin receptor activation include eating disorders, diabetes, pain, depression, ischemia, Alzheimer's disease and reproductive disorders. Accordingly, treatment of such disorders may be effected by the administration of GALR2 receptor-selective compounds. The localization of GALR2 receptors in other parts of the rat brain suggests that GALR2 receptors may play a role in cognition, analgesia, sensory processing (olfactory, visual), processing of visceral information, motor coordination, modulation of dopaminergic activity, neuroendocrine function, sleep disorders, migraine, and anxiety.

SUMMARY OF THE INVENTION

This invention provides an isolated nucleic acid encoding a mammalian GALR2 galanin receptor. This invention further provides a recombinant nucleic acid encoding a mammalian GALR2 galanin receptor.

This invention further provides an isolated nucleic acid encoding a modified GALR2 receptor, which differs from a GALR2 receptor by having an amino acid(s) deletion, replacement or addition in the third intracellular domain.

This invention also provides a purified GALR2 receptor protein.

This invention further provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid K985.

This invention further provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid K1045.

This invention also provides a nucleic acid probe comprising at least 15 nucleotides, which probe specifically hybridizes with a nucleic acid encoding a GALR2 receptor, wherein the probe has a unique sequence corresponding to a sequence present within (a) the nucleic acid sequence shown in FIG. 1 or (b) the reverse complement of the nucleic acid sequence shown in FIG. 1.

This invention also provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid BO29.

This invention further provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid BO39.

This invention provides a nucleic acid probe comprising at least 15 nucleotides, which probe specifically hybridizes with a nucleic acid encoding a GALR2 receptor, wherein the probe has a unique sequence corresponding to a sequence present within (a) the nucleic acid sequence shown in FIG. 10 or (b) the reverse complement of the nucleic acid sequence shown in FIG. 10.

This invention also provides a nucleic acid probe comprising a nucleic acid molecule of at least 15 nucleotides which is complementary to a unique fragment of the sequence of a nucleic acid molecule encoding a GALR2 receptor.

This invention further provides a nucleic acid probe comprising a nucleic acid molecule of at least 15 nucleotides which is complementary to the antisense sequence of a unique fragment of the sequence of a nucleic acid molecule encoding a GALR2 receptor.

This invention provides a transgenic nonhuman mammal comprising a homologous recombination knockout of the native GALR2 receptor.

This invention also provides a process for identifying a chemical compound which specifically binds to a GALR2 receptor which comprises contacting cells containing DNA encoding and expressing on their cell surface the GALR2 receptor, wherein such cells do not normally express the GALR2 receptor, with the compound under conditions suitable for binding, and detecting specific binding of the chemical compound to the GALR2 receptor.

This invention further provides a process for identifying a chemical compound which specifically binds to a GALR2 receptor which comprises contacting a membrane fraction from a cell extract of cells containing DNA encoding and expressing on their cell surface the GALR2 receptor, wherein such cells do not normally express the GALR2 receptor, with the compound under conditions suitable for binding, and detecting specific binding of the chemical compound to the GALR2 receptor.

This invention additionally provides a process for determining whether a chemical compound is a GALR2 receptor agonist which comprises contacting cells transfected with and expressing DNA encoding the GALR2 receptor with the compound under conditions permitting the activation of the GALR2 receptor, and detecting an increase in GALR2 receptor activity, so as to thereby determine whether the compound is a GALR2 receptor agonist.

This invention also provides a process for determining whether a chemical compound is a GALR2 receptor agonist which comprises preparing a cell extract from cells transfected with and expressing DNA encoding the GALR2 receptor, isolating a membrane fraction from the cell extract, contacting the membrane fraction with the compound under conditions permitting the activation of the GALR2 receptor, and detecting an increase in GALR2 receptor activity, so as to thereby determine whether the compound is a GALR2 receptor agonist.

This invention further provides a process for determining whether a chemical compound is a GALR2 receptor agonist which comprises preparing a cell extract from cells transfected with and expressing DNA encoding the GALR2 receptor, isolating a membrane fraction from the cell extract, separately contacting the membrane fraction with both the chemical compound and GTPγS, and with only GTPγS, under conditions permitting the activation of the GALR2 receptor, and detecting GTPγS binding to the membrane fraction, an increase in GTPγS binding in the presence of the compound indicating that the chemical compound activates the GALR2 receptor.

This invention provides a process for determining whether a chemical compound is a GALR2 receptor antagonist which comprises contacting cells transfected with and expressing DNA encoding the GALR2 receptor with the compound in the presence of a known GALR2 receptor agonist, under conditions permitting the activation of the GALR2 receptor, and detecting a decrease in GALR2 receptor activity, so as to thereby determine whether the compound is a GALR2 receptor antagonist.

This invention also provides a process for determining whether a chemical compound is a GALR2 receptor antagonist which comprises preparing a cell extract from cells transfected with and expressing DNA encoding the GALR2 receptor, isolating a membrane fraction from the cell extract, contacting the membrane fraction with the ligand in the presence of a known GALR2 receptor agonist, under conditions permitting the activation of the GALR2 receptor, and detecting a decrease in GALR2 receptor activity, so as to thereby determine whether the compound is a GALR2 receptor antagonist.

This invention further provides a process involving competitive binding for identifying a chemical compound which specifically binds to a GALR2 receptor which comprises separately contacting cells expressing on their cell surface the GALR2 receptor, wherein such cells do not normally express the GALR2 receptor, with both the chemical compound and a second chemical compound known to bind to the receptor, and with only the second chemical compound, under conditions suitable for binding of both compounds, and detecting specific binding of the chemical compound to the GALR2 receptor, a decrease in the binding of the second chemical compound to the GALR2 receptor in the presence of the chemical compound indicating that the chemical compound binds to the GALR2 receptor.

This invention provides a process involving competitive binding for identifying a chemical compound which specifically binds to a human GALR2 receptor which comprises separately contacting a membrane fraction from a cell extract of cells expressing on their cell surface the GALR2 receptor, wherein such cells do not normally express the GALR2 receptor, with both the chemical compound and a second chemical compound known to bind to the receptor, and with only the second chemical compound, under conditions suitable for binding of both compounds, and detecting specific binding of the chemical compound to the GALR2 receptor, a decrease in the binding of the second chemical compound to the GALR2 receptor in the presence of the chemical compound indicating that the chemical compound binds to the GALR2 receptor.

This invention also provides a process for determining whether a chemical compound specifically binds to and activates a GALR2 receptor, which comprises contacting cells producing a second messenger response and expressing on their cell surface the GALR2 receptor, wherein such cells do not normally express the GALR2 receptor, with the chemical compound under conditions suitable for activation of the GALR2 receptor, and measuring the second messenger response in the presence and in the absence of the chemical compound, a change in the second messenger response in the presence of the chemical compound indicating that the compound activates the GALR2 receptor.

This invention further provides a process for determining whether a chemical compound specifically binds to and activates a GALR2 receptor, which comprises contacting a membrane fraction isolated from a cell extract of cells producing a second messenger response and expressing on their cell surface the GALR2 receptor, wherein such cells do not normally express the GALR2 receptor, with the chemical compound under conditions suitable for activation of the GALR2 receptor, and measuring the second messenger response in the presence and in the absence of the chemical compound, a change in the second messenger response in the presence of the chemical compound indicating that the compound activates the GALR2 receptor.

This invention also provides a process for determining whether a chemical compound specifically binds to and inhibits activation of a GALR2 receptor, which comprises separately contacting cells producing a second messenger response and expressing on their cell surface the GALR2 receptor, wherein such cells do not normally express the GALR2 receptor, with both the chemical compound and a second chemical compound known to activate the GALR2 receptor, and with only the second chemical compound, under conditions suitable for activation of the GALR2 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the GALR2 receptor.

This invention further provides a process for determining whether a chemical compound specifically binds to and inhibits activation of a GALR2 receptor, which comprises separately contacting a membrane fraction from a cell extract of cells producing a second messenger response and expressing on their cell surface the GALR2 receptor, wherein such cells do not normally express the GALR2 receptor, with both the chemical compound and a second chemical compound known to activate the GALR2 receptor, and with only the second chemical compound, under conditions suitable for activation of the GALR2 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the GALR2 receptor.

This invention also provides a method of screening a plurality of chemical compounds not known to bind to a GALR2 receptor to identify a compound which specifically binds to the GALR2 receptor, which comprises (a) contacting cells transfected with and expressing DNA encoding the GALR2 receptor with a compound known to bind specifically to the GALR2 receptor;

(b) contacting the preparation of step (a) with the plurality of compounds not known to bind specifically to the GALR2 receptor, under conditions permitting binding of compounds known to bind the GALR2 receptor;

(c) determining whether the binding of the compound known to bind to the GALR2 receptor is reduced in the presence of the compounds, relative to the binding of the compound in the absence of the plurality of compounds; and if so (d) separately determining the binding to the GALR2 receptor of each compound included in the plurality of compounds, so as to thereby identify the compound which specifically binds to the GALR2 receptor.

This invention provides a method of screening a plurality of chemical compounds not known to bind to a GALR2 receptor to identify a compound which specifically binds to the GALR2 receptor, which comprises (a) preparing a cell extract from cells transfected with and expressing DNA encoding the GALR2 receptor, isolating a membrane fraction from the cell extract, contacting the membrane fraction with a compound known to bind specifically to the GALR2 receptor;

(b) contacting the preparation of step (a) with the plurality of compounds not known to bind specifically to the GALR2 receptor, under conditions permitting binding of compounds known to bind the GALR2 receptor;

(c) determining whether the binding of the compound known to bind to the GALR2 receptor is reduced in the presence of the compounds, relative to the binding of the compound in the absence of the plurality of compounds; and if so (d) separately determining the binding to the GALR2 receptor of each compound included in the plurality of compounds, so as to thereby identify the compound which specifically binds to the GALR2 receptor.

This invention further provides a method of screening a plurality of chemical compounds not known to activate a GALR2 receptor to identify a compound which activates the GALR2 receptor which comprises (a) contacting cells transfected with and expressing the GALR2 receptor with the plurality of compounds not known to activate the GALR2 receptor, under conditions permitting activation of the GALR2 receptor;

(b) determining whether the activity of the GALR2 receptor is increased in the presence of the compounds; and if so (c) separately determining whether the activation of the GALR2 receptor is increased by each compound included in the plurality of compounds, so as to thereby identify the compound which activates the GALR2 receptor.

This invention further provides a method of screening a plurality of chemical compounds not known to activate a GALR2 receptor to identify a compound which activates the GALR2 receptor which comprises (a) preparing a cell extract from cells transfected with and expressing DNA encoding the GALR2 receptor, isolating a membrane fraction from the cell extract, contacting the membrane fraction with the plurality of compounds not known to activate the GALR2 receptor, under conditions permitting activation of the GALR2 receptor;

(b) determining whether the activity of the GALR2 receptor is increased in the presence of the compounds; and if so (c) separately determining whether the activation of the GALR2 receptor is increased, by each compound included in the plurality of compounds, so as to thereby identify the compound which activates the GALR2 receptor.

This invention also provides a method of screening a plurality of chemical compounds not known to inhibit the activation of a GALR2 receptor to identify a compound which inhibits the activation of the GALR2 receptor, which comprises (a) contacting cells transfected with and expressing the GALR2 receptor with the plurality of compounds in the presence of a known GALR2 receptor agonist, under conditions permitting activation of the GALR2 receptor;

(b) determining whether the activation of the GALR2 receptor is reduced in the presence of the plurality of compounds, relative to the activation of the GALR2 receptor in the absence of the plurality of compounds; and if so (c) separately determining the inhibition of activation of the GALR2 receptor for each compound included in the plurality of compounds, so as to thereby identify the compound which inhibits the activation of the GALR2 receptor.

This invention further provides a method of screening a plurality of chemical compounds not known to inhibit the activation of a GALR2 receptor to identify a compound which inhibits the activation of the GALR2 receptor, which comprises
(a) preparing a cell extract from cells transfected with and expressing DNA encoding the GALR2 receptor, isolating a membrane fraction from the cell extract, contacting the membrane fraction with the plurality of compounds in the presence of a known GALR2 receptor agonist, under conditions permitting activation of the GALR2 receptor;
(b) determining whether the activation of the GALR2 receptor is reduced in the presence of the plurality of compounds, relative to the activation of the GALR2 receptor in the absence of the plurality of compounds; and if so
(c) separately determining the inhibition of activation of the GALR2 receptor for each compound included in the plurality of compounds, so as to thereby identify the compound which inhibits the activation of the GALR2 receptor.

This invention also provides a method of modifying feeding behavior of a subject which comprises administering to the subject an amount of a compound which is a GALR2 receptor agonist or antagonist effective to increase or decrease the consumption of food by the subject so as to thereby modify feeding behavior of the subject.

This invention provides a method for determining whether a compound is a GALR2 antagonist which comprises:
(a) administering to an animal a GALR2 agonist and measuring the amount of food intake in the animal;
(b) administering to a second animal both the GALR2 agonist and the compound, and measuring the amount of food intake in the second animal; and
(c) determining whether the amount of food intake is reduced in the presence of the compound relative to the amount of food intake in the absence of the compound, so as to thereby determine whether the compound is a GALR2 antagonist.

This invention further provides a method of decreasing feeding behavior of a subject which comprises administering a compound which is a GALR2 receptor antagonist and a compound which is a Y5 receptor antagonist, the amount of such antagonists being effective to decrease the feeding behavior of the subject.

This invention further provides a method of decreasing nociception in a subject which comprises administering to the subject an amount of a compound which is a GALR2 receptor agonist effective to decrease nociception in the subject.

This invention provides a method of treating pain in a subject which comprises administering to the subject an amount of a compound which is a GALR2 receptor agonist effective to treat pain in the subject.

This invention further provides a method of treating Alzheimer's disease in a subject which comprises administering to the subject an amount of a compound which is a GALR2 receptor antagonist effective to treat Alzheimer's disease in the subject.

BRIEF DESCRIPTION OF THE FIGURES

FIGS. 3A–3C 3A. Diagram of the intron-exon arrangement of the rat GALR2 receptor cDNA contained in plasmid K985. Untranslated regions are indicated by dark hatched segments, and coding region is unmarked except for light gray hatched segments indicating the location of the transmembrane domains of the rat GALR2 receptor. The black segment indicates the location of the intron. 3B. Splice junction sequences of the rat GALR2 receptor. Nucleotide number 1 is located 45 nucleotides upstream of the start codon (SEQ ID NO: 9). 3C. Intron sequence of rat GALR2 receptor cDNA contained in plasmid K985. Nucleotide number 1 is located 45 nucleotides upstream of the start codon (SEQ ID NO: 9).

FIGS. 4A-1 and 4A-4: Distribution of total [$^{125}$I]galanin binding in coronal sections through the hypothalamus and amygdala. FIGS. 4A-2 and 4A-5: Binding which remains in these areas following incubation with 60 nM [D-Trp$^2$]galanin$_{(1-29)}$. FIGS. 4A-3 and 4A-6: Binding obtained after incubation with 5 μM porcine galanin, which represents the non-specific binding condition. FIG. 4B: FIGS. 4B-1 to 4B-8: Higher magnification photomicrographs of the [$^{125}$I]galanin binding sites in the hypothalamus and amygdala. FIG. 4B-1: Total binding in the paraventricular hypothalamic nucleus (PVN), virtually all of which is removed by 60 nM [D-Trp$^2$]galanin$_{(1-29)}$ (panel 3B). FIGS. 4B-3 and 4B-4: Binding in the ventromedial hypothalamus (VMH), lateral hypothalamus (LH), and zona incerta (ZI). In these regions, some [$^{125}$I]galanin binding remains after incubation with 60 nM [D-Trp$^2$]galanin$_{(1-29)}$ (FIG. 4B-4) FIGS. 4B-5 and 4B-7: Total binding in the amygdala. After incubation with 60 nM [D-Trp$^2$]galanin$_{(1-29)}$ (panels 5B and 6B), the binding is markedly reduced in the piriform cortex (Pir), and to a lesser extent in the medial nucleus (Me), and central nucleus (Ce). However, the binding in the nucleus of the lateral olfactory tract (LOT) is largely unaffected. FIG. 4C: FIGS. 4C-1 to 4C-6: Distribution of [$^{125}$I]galanin binding sites in the anterior forebrain (FIGS. 4C-1 and 4C-2) and in the midbrain (FIGS. 4C-4 and 4C-5). FIGS. 4C-1 and 4C-2: In the lateral septum (LS) and insular cortex (CTX), much of the total binding (FIG. 4C-1) is removed by 60 nM [D-Trp$^2$]galanin$_{(1-29)}$ (FIG. 4C-2). FIGS. 4C-4 and 4C-5: Similarly, the total binding observed in the superior colliculus (SC), central gray (CG), and pontine reticular nucleus (PnO) (FIG. 4C-4) is markedly diminished by 60 nM [D-Trp$^2$]galanin$_{(1-29)}$ (FIG. 4C-5). FIGS. 4C-3 and 4C-6: Nonspecific binding observed in adjacent sections through the septum and midbrain. Arc, arcuate nucleus; Ce, central amygdaloid nucleus; CL, centrolateral thalamic nucleus; LOT, nucleus of the lateral olfactory tract; Me, medial amygdaloid nucleus; Pir, piriform cortex; PVN, paraventricular hypothalamic nucleus; SO, supraoptic nucleus; st, stria terminalis; VMH, ventromedial hypothalamic nucleus; ZI, zona incerta.

FIG. 5. Reverse transcriptase PCR (RT-PCR) of rat GALR2 receptor mRNA from various brain regions. The blot was hybridized at high stringency with an oligonucleotide probe corresponding to a portion of the predicted V/VI loop of GALR2. Positive controls are indicated by +'s and represent plasmids containing the indicated inserts. Size standards are indicated at the left in kilobases. Note the additional hybridizing bands intermediate in size between the intron-containing and the intronless product.

8B: Nonspecific binding of 6 nM $^{125}$I-[D-Trp$^2$]Galanin$_{(1-29)}$ in the presence of 300 nM porcine galanin$_{(1-29)}$ to COS-7 cells transiently transfected with GALR2.

8C: Binding of 6 nM $^{125}$I-[D-Trp$^2$]Galanin$_{(1-29)}$ to COS-7 cells transiently transfected with GALR1. Note absence of binding to cell profiles; small accumulations of, silver grains represent nonspecific nuclear association.

8D: Nonspecific binding of 6 nM [$^{125}$I]-[D-Trp$^2$]Galanin$_{(1-29)}$ in the presence of 600 nM porcine galanin$_{(1-29)}$ to COS-7 cells transiently transfected with GALR1.

Figure 9A:
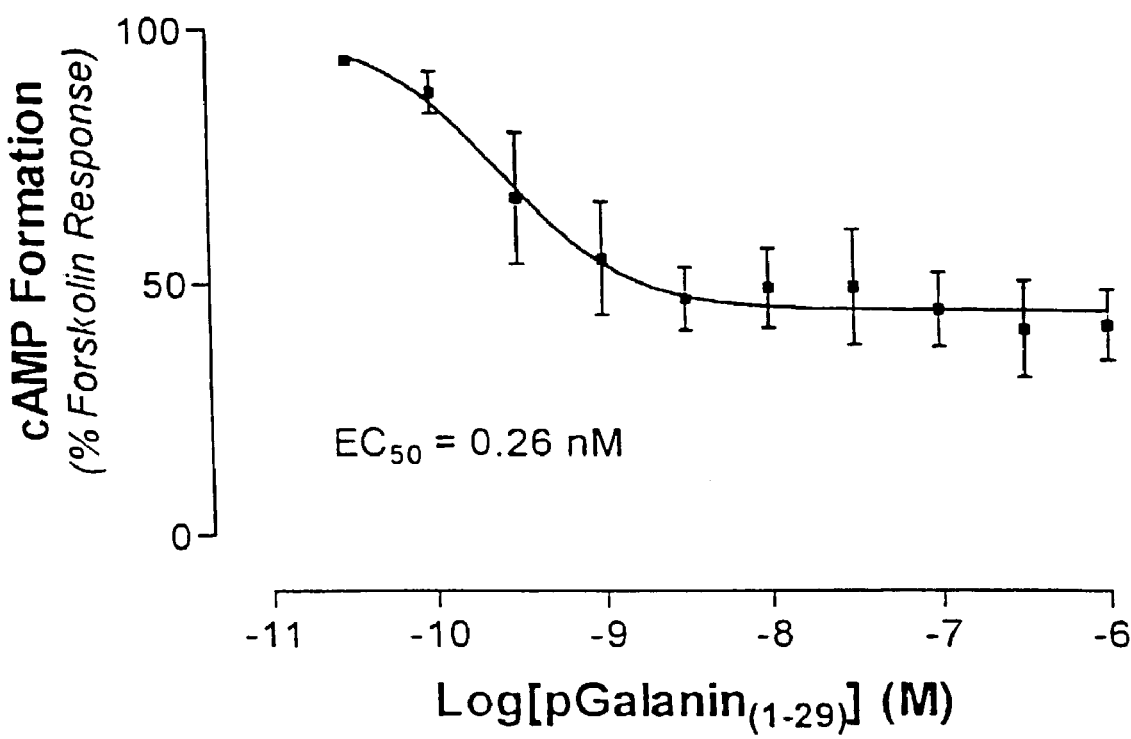
Figure 9B:
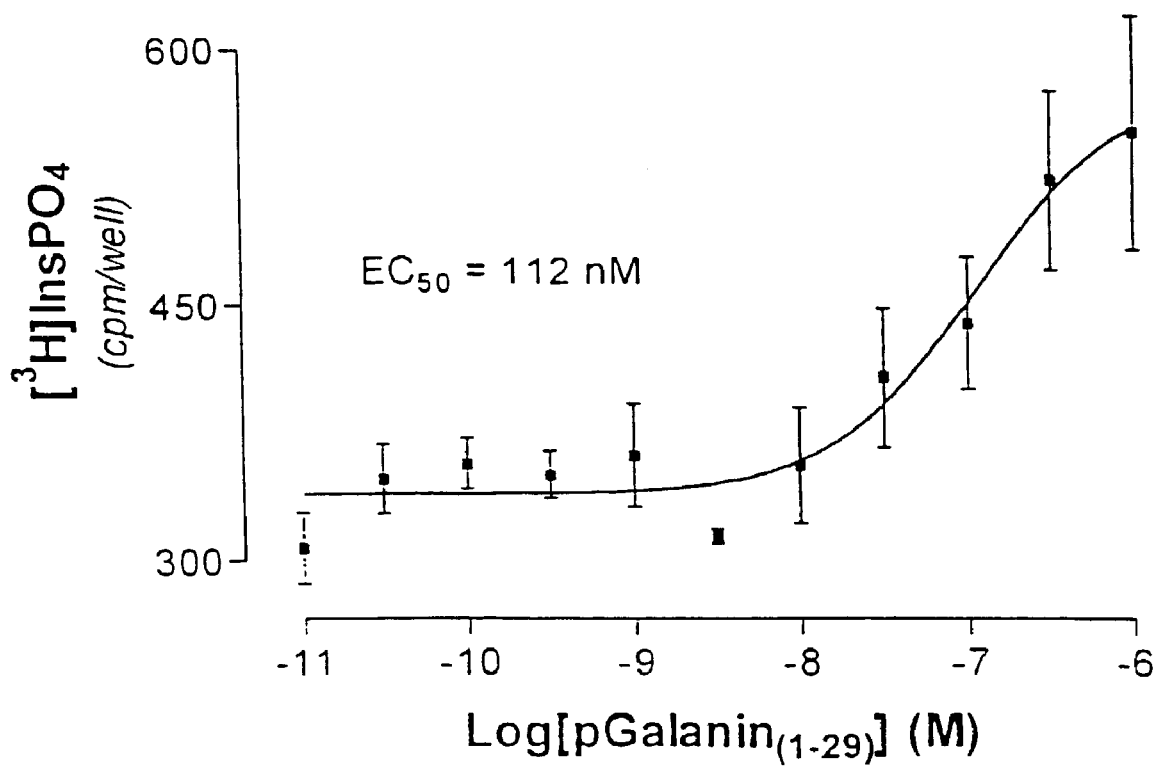

FIGS. 9A–9B. Functional response mediated by LM(tk-) cells stably transfected with the cDNA encoding the rat GALR2 receptor. 9A: Inhibition of cyclic AMP formation: cells were incubated with varying concentrations of porcine galanin$_{(1-29)}$ and 10 μM forskolin for 15 min. at 37° C. Data was normalized taking as 0% the basal levels of cyclic AMP (0.06±0.02 pmol/ml) and 100% the cAMP levels produced by forskolin in the absence of agonist (0.26±0.03 pmol/ml). Data is shown as mean±standard error of the mean of four independent experiments. 9B: Phosphoinositide metabolism: cells were incubated for 18 hours in the presence of 0.5 μCi [$^3$H]myo-inositol. Eleven different concentrations of porcine galanin$_{(1-29)}$ were added in the presence on 10mM LiCl. Cells were incubated for 1 hour at 37° C., and [$^3$H]inositol phosphates were isolated and measured.

FIG. 10. Nucleotide coding sequence of the human galanin GALR2 receptor (SEQ ID NO: 27), with partial 5' and 3' untranslated sequences. Start (ATG) and stop (TGA) codons are underlined.

FIG. 11. Deduced amino acid sequence of the human galanin GALR2 receptor encoded by the nucleotide sequence shown in FIG. 10 (SEQ ID NO: 28)

Figure 12A:
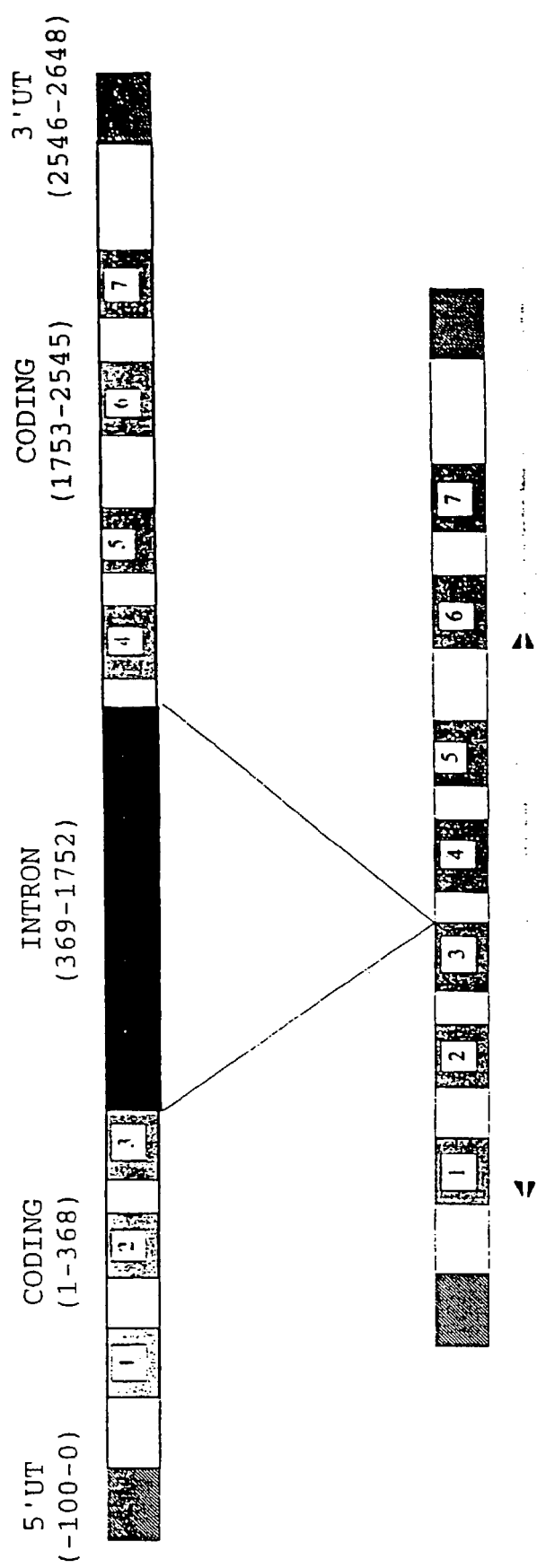
Figure 12B:
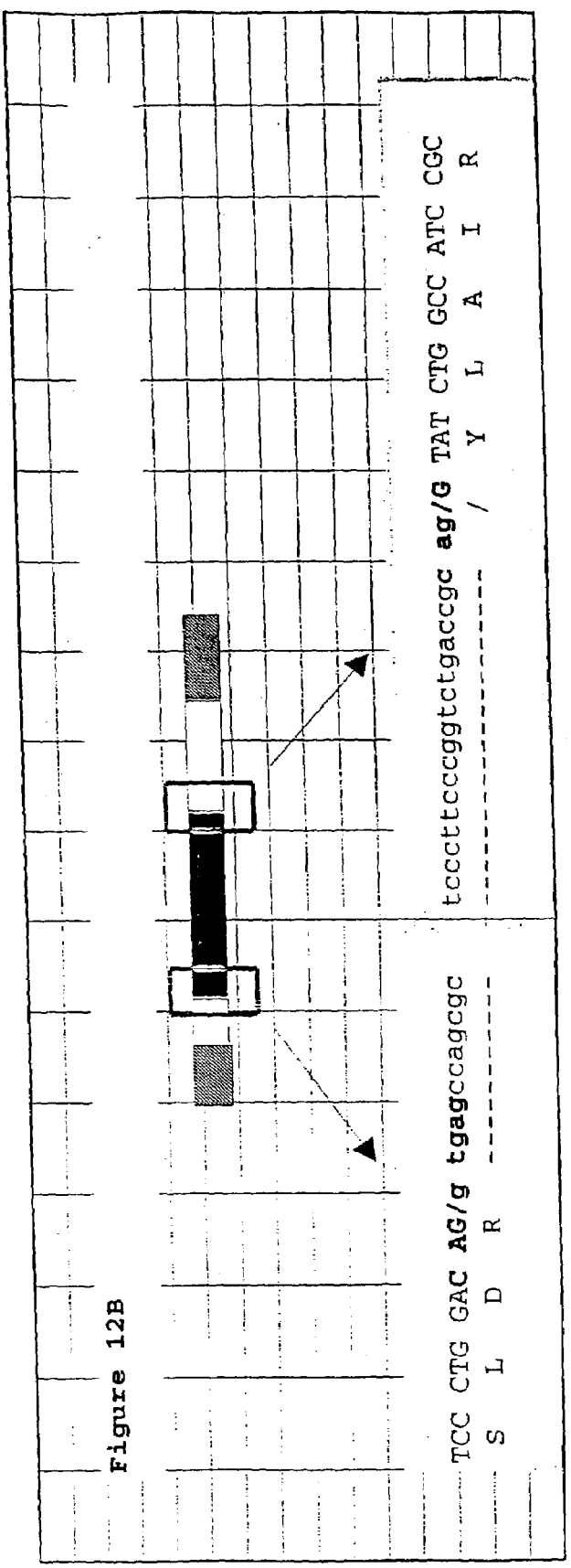

FIGS. 12A–12C. 12A. Diagram of the intron-exon arrangement of the human GALR2 receptor cDNA contained in plasmid BO29. Untranslated regions are indicated by dark hatched segments, and coding region is unmarked except for light gray hatched segments indicating the location of the transmembrane domains of the human GALR2 receptor. The black segment indicates the location of the intron. 12B. Splice junction sequences of the human GALR2 receptor. 12C. Intron sequence of human GALR2 receptor cDNA contained in plasmid BO29 (SEQ ID NO: 29)

Figure 13:
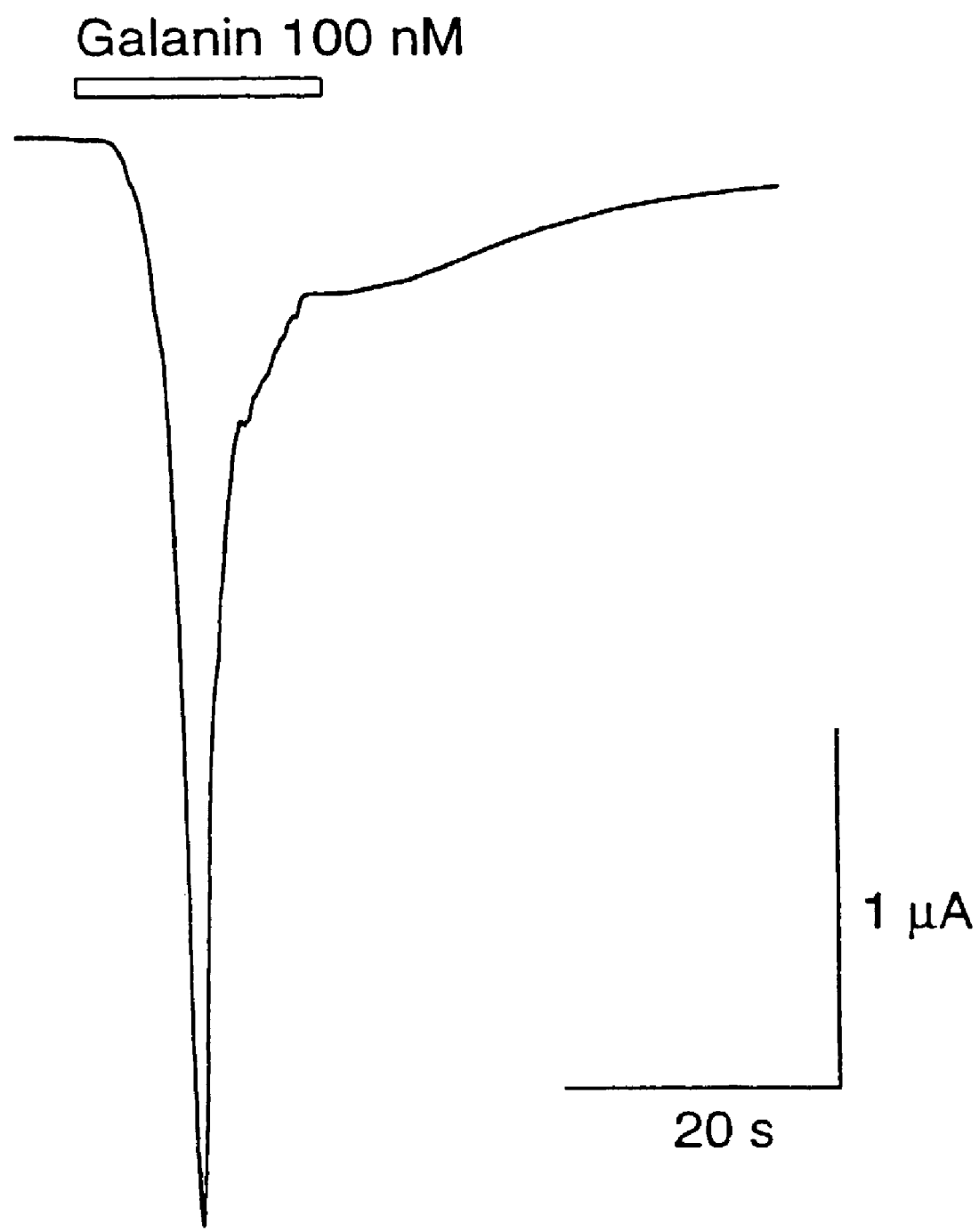

FIG. 13. Current response in an oocyte injected with 50 pg of GALR2 mRNA. Holding potential was −80 mV.

Figure 14:
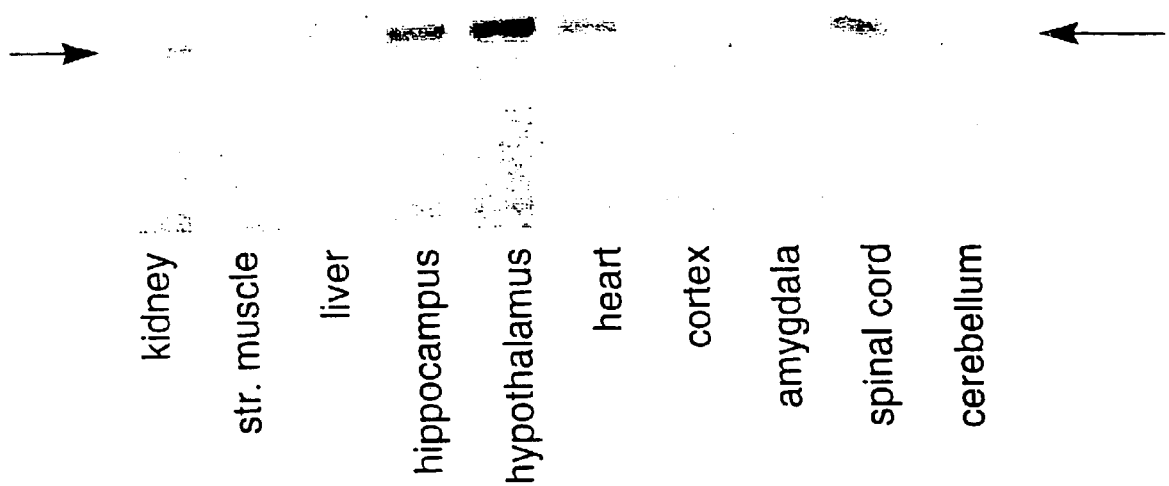
Figure 16A:
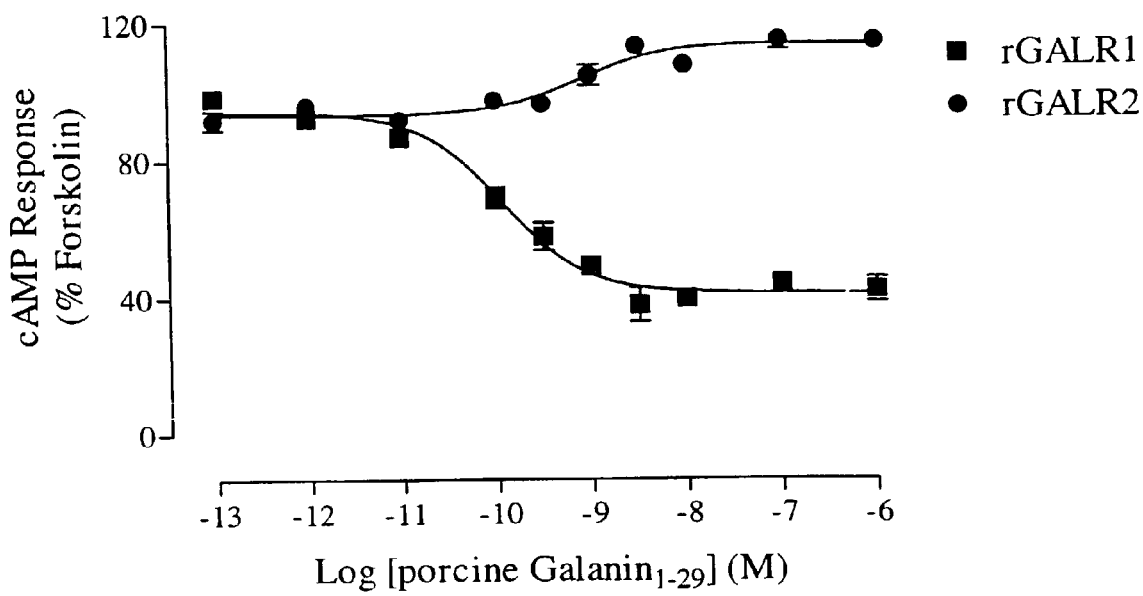
Figure 16B:
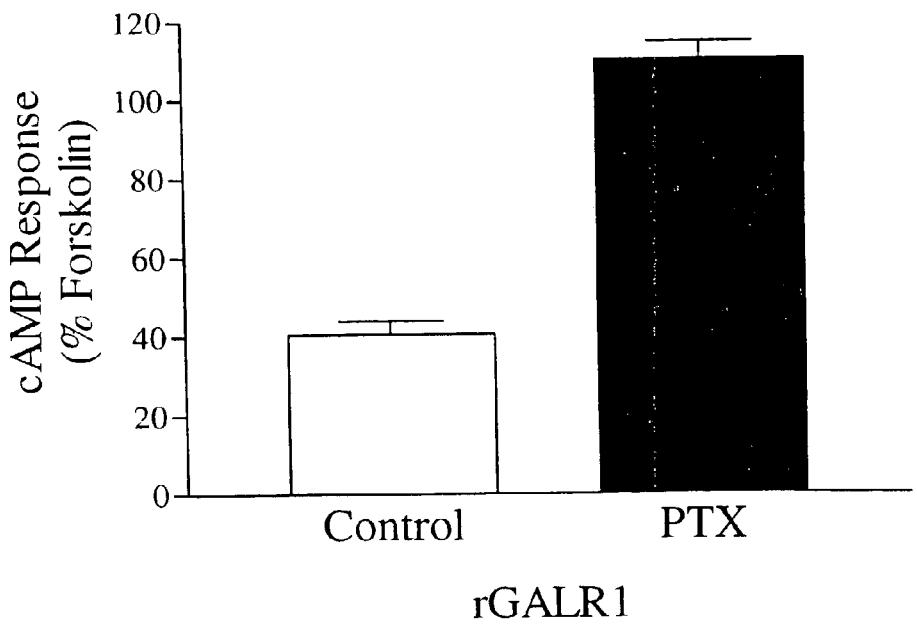
Figure 16C:
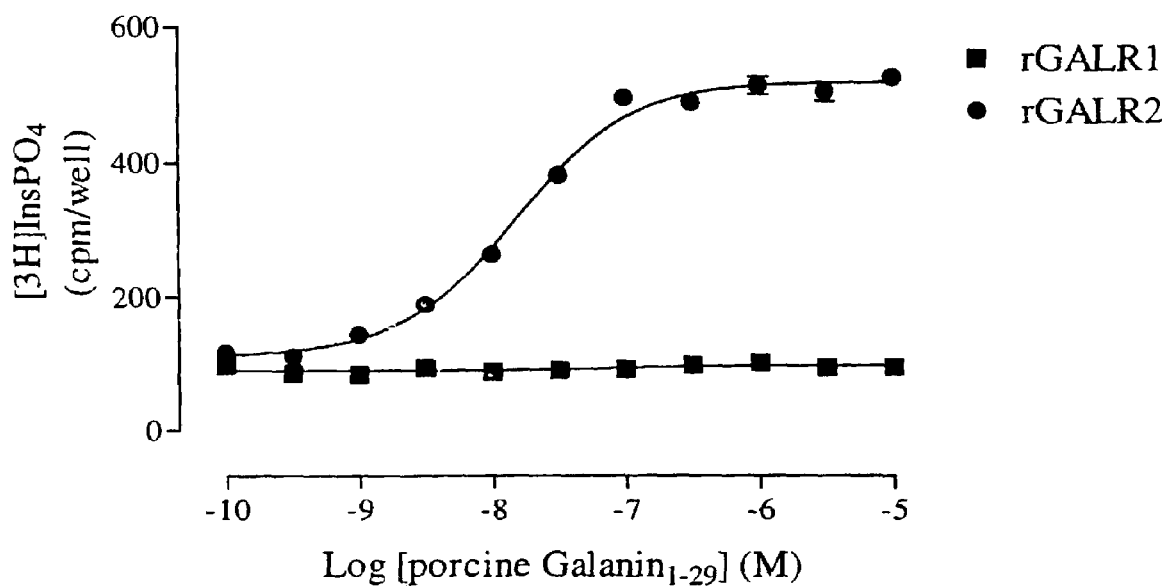
Figure 16D:
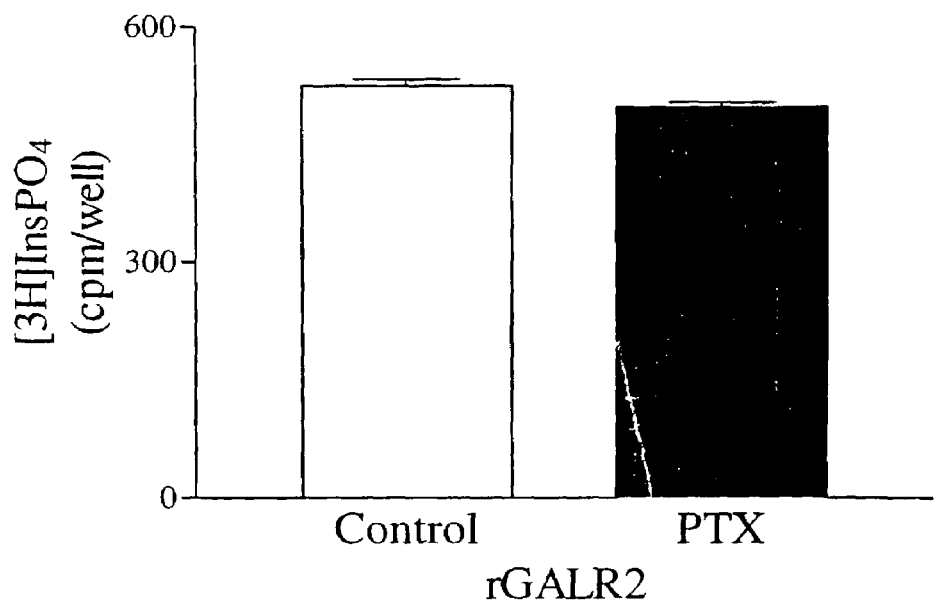

FIG. 14. Autoradiograph demonstrating hybridization of radiolabeled rGalR2 probe to RNA extracted from rat. The lower band (arrow) represents mRNA coding for the rat GALR2 extracted from tissue indicated at the bottom of the gel. RNA coding for the rat GALR2 is present in: the heart, kidney, hypothalamus, hippocampus, amygdala, spinal cord, and cerebellum. mRNA coding for the rat GALR2 was not detected in RNA extracted from striated muscle or liver.

FIGS. 15A–15D. Amino acid sequence alignment of the rat GALR2 receptor (top row) (SEQ ID NO: 8), human GALR2 receptor (middle row) (SEQ ID NO: 28) and rat GALR1 receptor (bottom row) (SEQ ID NO: 30). Transmembrane domains (TM 1–7) are indicated by brackets above the sequence.

FIGS. 16A–16D. Galanin-mediated stimulation of phosphatidylinositol turnover and cyclic AMP inhibition in CHO cells expressing the rat GALR1 and GALR2 receptors. 16A. CHO cell lines expressing the rat GALR1 (24 pmol/mg protein, ■) or the rat GALR2 (0.5 pmol/mg protein, ●) receptors were evaluated for galanin-dependent inhibition of forskolin-stimulated cAMP accumulation by radioimmunoassay. 16B. The effect of 1 μM porcine galanin on forskolin-stimulated cAMP accumulation was measured in CHO cells expressing the rat GALR1 receptor. Cells were incubated for 18 hrs in the presence (PTX) or absence (Control) of 100 ng/ml pertussis toxin. 16C. The same CHO cell lines expressing rat GALR1 (■) or rat GALR2 (●) receptors were evaluated for galanin-dependent stimulation of inositol phosphate accumulation after an 18 hr incubation with [$^3$H]myoinositol. 16D. The effect of 1 μM porcine galanin on the release of [$^3$H]inositol phosphates was measured in CHO cells expressing the rat GALR2 receptor incubated for 18 hrs in the presence —(PTX), or absence (Control) of 100 ng/ml pertussis toxin. Values represent the mean±SEM from three determinations. Data shown are representative of three or more independent experiments.

DETAILED DESCRIPTION OF THE INVENTION

Throughout this application, the following standard abbreviations are used to indicate specific nucleotide bases:

| C = cytosine | A = adenine |
|---|---|
| T = thymine | G = guanine |

Furthermore, the term "agonist" is used throughout this application to indicate any peptide or non-peptidyl compound which increases the activity of any of the receptors of the subject invention. The term "antagonist" is used throughout this application to indicate any peptide or non-peptidyl compound which decreases the activity of any of the receptors of the subject invention.

The activity of a G-protein coupled receptor such as a galanin receptor may be measured using any of a variety of functional assays in which activation of the receptor in question results in an observable change in the level of some second messenger system, including but not limited to adenylate cyclase, calcium mobilization, arachidonic acid release, ion channel activity, inositol phospholipid hydrolysis or guanylyl cyclase. Heterologous expression systems utilizing appropriate host cells to express the nucleic acid of the subject invention are used to obtain the desired second messenger coupling. Receptor activity may also be assayed in an oocyte expression system.

This invention provides an isolated nucleic acid encoding a vertebrate GALR2 receptor. In a separate embodiment, the nucleic acid encodes a mammalian GALR2 receptor. In another embodiment, the nucleic acid encodes a rat GALR2 receptor. In still another embodiment, the nucleic acid encodes a human GALR2 receptor.

This invention further provides nucleic acid which is degenerate with respect to the DNA comprising the coding sequence of the plasmid K985. This invention also provides nucleic acid which is degenerate with respect to the DNA comprising the coding sequence of the plasmid K1045. This invention further provides nucleic acid which is degenerate with respect to any DNA encoding a GALR2 receptor. In one embodiment, the nucleic acid comprises a nucleotide sequence which is degenerate with respect to the nucleotide sequence described in FIG. 1 (SEQ ID NO: 7), that is, a nucleotide sequence which is translated into the sane amino acid sequence. In another embodiment, the nucleic acid comprises a nucleotide sequence which is degenerate with respect to the nucleotide sequence described in SEQ ID NO: 9.

In yet another embodiment, this invention further provides nucleic acid which is degenerate with respect to the DNA comprising the coding sequence of plasmid BO29. In an emnbodiment, the nucleic acid comprises a nucleotide sequence which is degenerate with respect to the nucleotide sequence described in FIG. 10 (SEQ ID NO: 27), that is, a nucleotide sequence which is translated into the same amino acid sequence. This invention also provides nucleic acid which is degenerate with respect to the DNA comprising the coding sequence of the plasmid BO39.

The observation that both the human and rat GALR2 cDNAs contain at least one intron raises the possibility that additional introns could exist in coding or non-coding regions. In addition, spliced form(s) of mRNA may encode additional amino acids either upstream of the currently defined starting methionine or within the coding region. Further, the existence and use of alternative exons is possible, whereby the mRNA may encode different amino acids within the region comprising the exon. In addition, single amino acid substitutions may arise via the mechanism of RNA editing such that the amino acid sequence of the expressed protein is different than that encoded by the original gene (Burns et al., 1996; Chu et al., 1996). Such variants may exhibit pharmacologic properties differing from the receptor encoded by the original gene.

This invention provides a splice variant of the GALR2 receptors disclosed herein. This invention further provides for alternate translation initiation sites and alternately spliced or edited variants of nucleic acids encoding rat and human GALR2 receptors.

This invention also encompasses DNAs and cDNAs which encode amino acid sequences which differ from those of the GALR2 galanin receptor, but which should not produce phenotypic changes. Alternatively, this invention also encompasses DNAs, cDNAs, and RNAs which hybridize to the DNA, cDNA, and RNA of the subject invention. Hybridization methods are well known to those of skill in the art.

The nucleic acids of the subject invention also include nucleic acid molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

G-protein coupled receptors such as the GALR2 receptors of the present invention are characterized by the ability of an agonist to promote the formation of a high-affinity ternary complex between the agonist, the receptor, and an intracellular G-protein. This complex is formed in the presence of physiological concentrations of GTP, and results in the dissociation of the alpha subunit of the G protein from the beta and gamma subunits of the G protein, which further results in a functional response, i.e., activation of downstream effectors such as adenylyl cyclase or phospholipase C. This high-affinity complex is transient even in the presence of GTP, so that if the complex is destabilized, the affinity of the receptor for agonists is reduced. Thus, if a receptor is not optimally coupled to G protein under the conditions of an assay, an agonist will bind to the receptor with low affinity. In contrast, the affinity of the receptor for an antagonist is normally not significantly affected by the presence or absence of G protein. Functional assays may be used to determine whether a compound binds to the receptor, but may be more time-consuming or difficult to perform than a binding assay. Therefore, it may desirable to produce a receptor which will bind to agonists with high affinity in a binding assay. Examples of modified receptors which bind agonists with high affinity are disclosed in WO 96/14331, which describes neuropeptide Y receptors modified in the third intracellular domain. The modifications may include deletions of 6–13 amino acids in the third intracellular loop. Such deletions preferably end immediately before the polar or charged residue at the beginning of helix six. In one embodiment, the deleted amino acids are at the carboxy terminal portion of the third intracellular domain. Such modified receptors may be produced using methods well-known in the art such as site-directed mutagenesis or recombinant techniques using restriction enzymes.

The modified receptors of this invention may be transfected into cells either transiently or stably using methods well-known in the art, examples of which are disclosed herein. This invention also provides for binding assays using the modified receptors, in which the receptor is expressed either transiently or in stable cell lines. This invention further provides for a compound identified using a modified receptor in a binding assay such as the binding assays described herein.

The nucleic acids described and claimed herein are useful for the information which they provide concerning the amino acid sequence of the polypeptide and as products for the large scale synthesis of the polypeptide by a variety of recombinant techniques. The nucleic acid molecule is useful for generating new cloning and expression vectors, transformed and transfected prokaryotic and eukaryotic host cells, and new and useful methods for cultured growth of such host cells capable of expression of the polypeptide and related products.

This invention provides an isolated nucleic acid encoding a GALR2 galanin receptor. This invention further provides a recombinant nucleic acid encoding a GALR2 galanin receptor.

In one embodiment of this invention the isolated nucleic acid is DNA. In an embodiment, the DNA is cDNA. In another embodiment, the DNA is genomic DNA. In still another embodiment, the nucleic acid molecule is RNA. In yet another embodiment of the present invention the nucleic acid molecule is mRNA. Methods for production and manipulation of nucleic acid molecules are well known in the art.

In an embodiment, the galanin receptor is a vertebrate or a mammalian GALR2 receptor. In another embodiment, the galanin receptor is a rat GALR2 receptor. In another embodiment, the galanin receptor is a human GALR2 receptor. In an embodiment, the isolated nucleic acid encodes a receptor characterized by an amino acid sequence in the transmembrane region, which has a homology of 60% or higher to the amino acid sequence in the transmembrane region of the rat galanin GALR2 receptor and a homology of less than 60% to the amino acid sequence in the transmembrane region of any GALR1 receptor. In one embodiment, the GALR2 receptor is a rat GALR2 receptor. In another embodiment, the GALR2 receptor is a human GALR2 receptor.

In one embodiment, the GALR2 receptor has substantially the same amino acid sequence as the amino acid sequence encoded by plasmid K985 (ATCC Accession No. 97426). In another embodiment, the GALR2 receptor has the amino acid sequence encoded by the plasmid K985. In still another embodiment, the GALR2 receptor has substantially the same amino acid sequence as the amino acid sequence encoded by the plasmid K1045 (ATCC Accession No. 97778). In yet another embodiment, the GALR2 receptor has the amino acid sequence encoded by the plasmid K1045S. Plasmid K1045 comprises an intronless cDNA encoding the rat GALR2 receptor. Plasmid K1045 is further characterized by its lack of native 5' or 3' untranslated sequences, such that the plasmid contains only the regulatory elements necessary for expression in mammalian cells (e.g., Kozak consensus sequence) and the coding sequence of the GALR2 receptor.

Figure 3A:
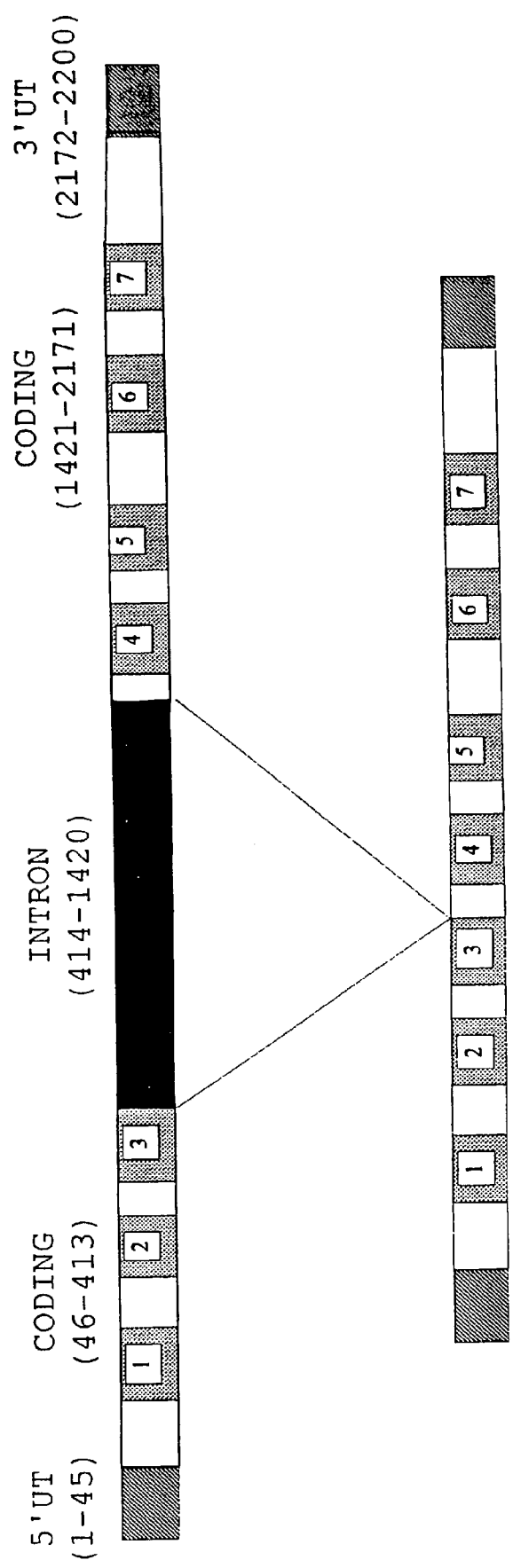
Figures 1, 4A:
FIG. 1 Nucleotide coding sequence of the rat hypothalamic galanin GALR2 receptor (SEQ ID NO: 7), with partial 5' and 3' untranslated sequences. Start (ATG) and stop (TAA) codons are underlined.
FIGS. 4A–4C Localization of [$^{125}$I] galanin binding sites in rat CNS.
Figures 2, 4A:
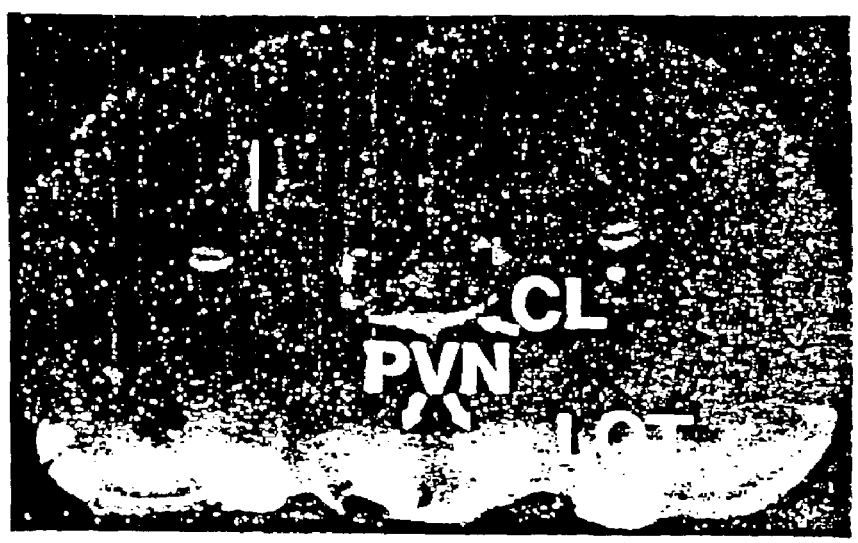
FIG. 2 Deduced amino acid sequence of the rat hypothalamic galanin GALR2 receptor encoded by the nucleotide sequence shown in FIG. 1 (SEQ ID NO: 8).

This invention provides an isolated nucleic acid encoding a GALR2 receptor having substantially the same amino acid sequence as shown in FIG. 2. In one embodiment, the nucleic acid is DNA. This invention further provides an isolated nucleic acid encoding a rat GALR2 receptor having the amino acid sequence shown in FIG. 2. In another embodiment, the nucleic acid comprises at least an intron. In yet another embodiment, the intron comprises a fragment of the intron sequence shown in FIG. 3C (SEQ ID NO: 9). In still another embodiment, the nucleic acid comprises alternately spliced nucleic acid transcribed from the nucleic acid contained in plasmid K985. In one embodiment, the alternately spliced nucleic acid is mRNA transcribed from DNA encoding a galanin receptor.

In one embodiment, the human GALR2 receptor has substantially the same amino acid sequence as the amino acid sequence encoded by plasmid BO29 (ATCC Accession No. 97735). In yet another embodiment, the human GALR2 receptor has the amino acid sequence encoded by the plasmid BO29. In another embodiment, the nucleic acid encoding the human GALR2 receptor comprises an intron. In still another embodimant, the nucleic acid encoding the human GALR2 receptor comprises alternately spliced nucleic acid transcribed from the nucleic acid contained in plasmid BO29. In still another embodiment, the human GALR2 receptor has substantially the same amino acid sequence as the amino acid sequence encoded by plasmid BO39 (ATCC Accession No. 97851). Tn another embodimant, the human GALR2 receptor has the amino acid sequence encoded by the plasmid BO39. Plasmid BO39 comprises an intronless cDNA encoding the human GALR2 receptor. This invention provides an isolated nucleic acid encoding a GALR2 receptor having substantially the same amino acid sequence as shown in FIG. 11 (SEQ ID NO: 28). In one embodiment, the nucleic acid is DNA. This invention further provides an isolated nucleic acid encoding a human GALR2 receptor having the amino acid sequence shown in FIG. 11.

This invention provides an isolated nucleic acid encoding a modified GALR2 receptor, which differs from a GALR2 receptor by having an amino acid(s) deletion, replacement or addition in the third intracellular domain. In one embodiment, the modified GALR2 receptor differs by having a deletion in the third intracellular domain. In another embodiment, the modified GALR2 receptor differs by having an amino acid replacement or addition to the third intracellular domain.

This invention also provides an isolated galanin GALR2 receptor protein. In one embodiment, the GALR2 receptor protein has the same or substantially the same amino acid sequence as the amino acid sequence encoded by plasmid K985. In another embodiment, the GALR2 receptor protein has the same or substantially the same amino acid sequence as the amino acid sequence encoded by plasmid K1045. In one embodiment, the GALR2 receptor protein has the same or substantially the same amino acid sequence as shown in FIG. 2. In another embodiment, the GALR2 receptor has the amino acid sequence shown in FIG. 2. In still another embodiment, the GALR2 receptor protein has the same or substantially the same amino acid sequence as the amino acid sequence encoded by plasmid BO29. In still another embodiment, the GALR2 receptor protein has the same or substantially the same amino acid sequence as the amino acid sequence encoded by plasmid BO39. In an embodiment, the GALR2 receptor protein has the same or substantially the same amino acid sequence as shown in FIG. 11. In another embodiment, the GALR2 receptor has the amino acid sequence shown in FIG. 11.

This invention provides a vector comprising the above-described nucleic acid molecule. In one embodiment of the present invention the nucleic acid encodes a rat GALR2 receptor. In a further embodiment of the present invention the nucleic acid encodes a human GALR2 receptor.

Vectors which comprise the isolated nucleic acid molecule described hereinabove also are provided. Suitable vectors comprise, but are not limited to, a plasmid or a virus. These vectors may be transformed into a suitable host cell to form a host cell expression system for the production of a polypeptide having the biological activity of a galanin GALR2 receptor. Suitable host cells include, for example, neuronal cells such as the glial cell line C6, a Xenopus cell such as an oocyte or melanophore cell, as well as numerous mammalian cells and non-neuronal cells.

This invention provides the above-described vector adapted for expression in a bacterial cell which further comprises the regulatory elements necessary for expression of the nucleic acid in the bacterial cell operatively linked to the nucleic acid encoding the GALR2 receptor as to permit expression thereof.

This invention provides the above-described vector adapted for expression in a yeast cell which comprises the regulatory elements necessary for expression of the nucleic acid in the yeast cell operatively linked to the nucleic acid encoding the GALR2 receptor as to permit expression thereof.

This invention provides the above-described vector adapted for expression in an insect cell which comprises the regulatory elements necessary for expression of the nucleic acid in the insect cell operatively linked to the nucleic acid encoding the GALR2 receptor as to permit expression thereof. In a still further embodiment, the vector is a baculovirus.

In one embodiment, the vector is adapted for expression in a mammalian cell which comprises the regulatory elements necessary for expression of the nucleic acid in the mammalian cell operatively linked to the nucleic acid encoding the mammalian GALR2 receptor as to permit expression thereof.

In a further embodiment, the vector is adapted for expression in a mammalian cell which comprises the regulatory elements necessary for expression of the nucleic acid in the mammalian cell operatively linked to the nucleic acid encoding the rat GALR2 receptor as to permit expression thereof.

In a still further embodiment, the vector is a plasmid.

In another embodiment, the plasmid is adapted for expression in a mammalian cell which comprises the regulatory elements necessary for expression of the nucleic acid in the mammalian cell operatively linked to the nucleic acid encoding the human GALR2 receptor as to permit expression thereof.

This invention provides the above-described plasmid adapted for expression in a mammalian cell which comprises the regulatory elements necessary for expression of nucleic acid in a mammalian cell operatively linked to the nucleic acid encoding the mammalian GALR2 receptor as to permit expression thereof.

This invention provides a plasmid designated K985 (ATCC Accession No. 97426) which comprises the regulatory elements necessary for expression of DNA in a mammalian cell operatively linked to DNA encoding the GALR2 galanin receptor so as to permit expression thereof.

The plasmid designated K985 was deposited on Jan. 24, 1996, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 97426.

This invention provides a plasmid designated K1045 (ATCC Accession No. 97778) which comprises the regulatory elements necessary for expression of DNA in a mammalian cell operatively linked to DNA encoding the GALR2 galanin receptor so as to permit expression thereof.

The plasmid designated K1045 was deposited on Oct. 30, 1996, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 97426.

This invention provides a plasmid designated BO29 (ATCC Accession No. 97735) which comprises the regulatory elements necessary for expression of DNA in a mammalian cell operatively linked to DNA encoding the GALR2 galanin receptor as to permit expression thereof.

The plasmid designated BO29 was deposited on Sep. 25, 1996, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 97735.

This invention provides a plasmid designated BO39 (ATCC Accession No. 97851) which comprises the regulatory elements necessary for expression of DNA in a mammalian cell operatively linked to DNA encoding the GALR2 galanin receptor as to permit expression thereof.

The plasmid designated BO39 was deposited on Jan. 15, 1997, with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure and was accorded ATCC Accession No. 97851.

This invention further provides for any vector or plasmid which comprises modified untranslated sequences, which are beneficial for expression in desired host cells or for use in binding or functional assays. For example, a vector or plasmid with untranslated sequences of varying lengths may express differing amounts of the receptor depending upon the host cell used. In an embodiment, the vector or plasmid comprises the coding sequence of the GALR2 receptor and the regulatory elements necessary for expression in the host cell.

This invention provides a cell comprising the above-identified plasmid or vector. This invention provides a eukaryotic cell comprising the above-described plasmid or vector. This invention provides a non-mammalian cell comprising the above-described plasmid or vector. This invention also provides a mammalian cell comprising the above-described plasmid or vector. In an embodiment the cell is a Xenopus oocyte or melanophore cell. In an embodiment, the cell is a neuronal cell such as the glial cell line C6. In an embodiment, the mammalian cell is non-neuronal in origin. In an embodiment, the mammalian cell is a COS-7 cell. In another embodiment the mammalian cell is a Chinese hamster ovary (CHO) cell. In another embodiment, the cell is a mouse Y1 cell.

In still another embodiment, the mammalian cell is a 293 human embryonic kidney cell. In still another embodiment, the mammalian cell is a NIH-3T3 cell. In another embodiment, the mammalian cell is an LM(tk-) cell. In still another embodiment, the mammalian cell is the LM(tk-) cell designated L-rGALR2-8. This cell line was deposited with the ATCC on Mar. 28, 1996, under the provisions of the Budapest Treaty for the International Recognition of the Deposit of Microorganisms for the Purposes of Patent Procedure, and was accorded ATCC Accession No. CRL-12074. In yet another embodiment, the mammalian cell is the LM(tk-) cell designated L-rGALR2I-4 (which comprises the intronless plasmid K1045). This cell line was deposited with the ATCC on Oct. 30, 1996, under the provisions of the Budapest Treaty for the International Recognition of the Deposit of Microorganisms for the Purposes of Patent Procedure, and was accorded ATCC Accession No. CRL-12223.

In another embodiment, the mammalian cell is the Chinese hamster ovary (CHO) cell designated C-rGalR2-79. C-rGalR2-79 expresses the rat GALR2 receptor and comprises a plasmid containing the intron within the coding region. This cell line was deposited with the ATCC on Jan. 15, 1997, under the provisions of the Budapest Treaty for the International Recognition of the Deposit of Microorganisms for the Purposes of Patent Procedure, and was accorded ATCC Accession No. CRL-12262.

In another embodiment, the mammalian cell is the Chinese hamster ovary (CHO) cell designated CHO-hGALR2-264. CHO-hGALR2-264 expresses the human GALR2 receptor and comprises the plasmid BO39. This cell line was deposited with the ATCC on Jul. 22, 1997, under the provisions of the Budapest Treaty for the International Recognition of the Deposit of Microorganisms for the Purposes of Patent Procedure, and was accorded ATCC Accession No. CRL-12379.

This invention also provides an insect cell comprising the above-described vector. In an embodiment, the insect cell is an Sf9 cell. In another embodiment, the insect cell is an Sf21 cell.

This invention provides a membrane preparation isolated from any of the above-described cells.

This invention provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid K985.

This invention further provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid K1045.

This invention still further provides a nucleic acid probe comprising at least 15 nucleotides, which probe specifically hybridizes with a nucleic acid encoding a GALR2 receptor, wherein the probe has a unique sequence corresponding to a sequence present within (a) the nucleic acid sequence described in FIG. 1 or (b) the reverse complement thereto. This invention also provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid BO29. This invention also provides a nucleic acid probe comprising at least 15 nucleotides, which probe specifically hybridizes with a nucleic acid encoding a GALR2 receptor, wherein the probe has a unique sequence corresponding to a sequence present within one of the two strands of the nucleic acid encoding the GALR2 receptor contained in plasmid BO39.

This invention provides a nucleic acid probe comprising at least 15 nucleotides, which probe specifically hybridizes with a nucleic acid encoding a GALR2 receptor, wherein the probe has a unique sequence corresponding to a sequence present within (a) the nucleic acid sequence shown in FIG. 10 (SEQ ID NO: 27) or (b) the reverse complement to the nucleic acid sequence shown in FIG. 10.

Figures 3, 4A:
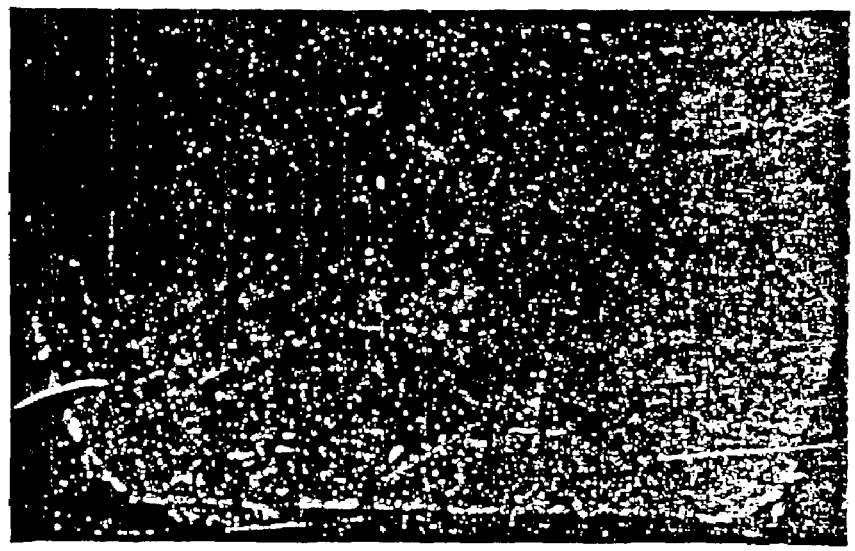
Figures 4, 4A:

This invention provides a nucleic acid probe comprising at least 15 nucleotides, which probe specifically hybridizes with a nucleic acid encoding a GALR2 receptor, wherein the probe has a unique sequence corresponding to a sequence present within a the nucleic acid sequence shown in FIG. 1 (SEQ ID NO: 7) or (b) the reverse complement to the nucleic acid sequence shown in FIG. 1 (SEQ ID NO: 7). In one embodinent, the nucleic acid encoding a GALR2 receptor comprises an intron, the sequence of which intron is described in FIG. 3 (SEQ ID NO: 9). In another embodiment, the nucleic acid encoding a GALR2 receptor comprises an intron, the sequence of which intron is described in FIG. 12C (SEQ ID NO: 29).

This invention further provides a nucleic acid probe comprising a nucleic acid molecule of at least 15 nucleotides which is complementary to a unique fragment of the sequence of a nucleic acid molecule encoding a GALR2 receptor. This invention also provides a nucleic acid probe comprising a nucleic acid molecule of at least 15 nucleotides which is complementary to the antisense sequence of a unique fragment of the sequence of a nucleic acid molecule encoding a GALR2 receptor.

In one embodiment, the nucleic acid probe is DNA. In another embodiment the nucleic acid probe is RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid of at least 15 nucleotides capable of specifically hybridizing with a sequence of a nucleic acid encoding the GALR2 galanin receptors can be used as a probe. In a further embodiment of the present invention the nucleic acid probe comprises a nucleic acid molecule of at least 15 nucleotides which is complementary to the antisense sequence of a unique fragment of the sequence of a nucleic acid molecule encoding a GALR2 receptor. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the GALR2 receptor into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers. RNA probes may be generated by inserting the DNA molecule which encodes the GALR2 galanin receptor downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention provides an antisense oligonucleotide having a sequence capable of specifically hybridizing to mRNA encoding a GALR2 galanin receptor, so as to prevent translation of the mRNA.

This invention provides an antisense oligonucleotide having a sequence capable of specifically hybridizing to the genomic DNA molecule encoding a GALR2 receptor.

This invention provides an antisense oligonucleotide comprising chemical analogues of nucleotides or chemically modified nucleotides.

This invention provides an antibody capable of binding to a GALR2 receptor. This invention also provides an antibody capable of binding to a rat GALR2 receptor. This invention also provides an antibody capable of binding to a human GALR2 receptor. In an embodiment, the human GALR2 has an amino acid sequence the same or substantially the same as an amino acid sequence encoded by plasmid K985 or an amino acid sequence encoded by plasmid BO29. In another embodiment, the human GALR2 has an amino acid sequence the same or substantially the same as an amino acid sequence encoded by plasmid BO39.

This invention provides an antibody capable of competitively inhibiting the binding of the antibody to a GALR2 receptor. In one embodiment of the present invention the antibody is a monoclonal antibody.

This invention provides a monoclonal antibody directed to an epitope of a GALR2 receptor, which epitope is present on the surface of a cell expressing a GALR2 receptor.

This invention provides a pharmaceutical composition comprising an amount of the oligonucleotide effective to reduce activity of a GALR2 receptor by passing through a cell membrane and binding specifically with mRNA encoding a GALR2 receptor in the cell so as to prevent its translation and a pharmaceutically acceptable carrier capable of passing through a cell membrane. In one embodiment, the oligonucleotide is coupled to a substance which inactivates mRNA. In another embodiment, the substance which inactivates mRNA is a ribozyme.

This invention provides the above-described pharmaceutical composition, wherein the pharmaceutically acceptable carrier capable of passing through a cell membrane comprises a structure which binds to a receptor specific for a selected cell type and is thereby taken up by cells of the selected cell type.

This invention provides a pharmaceutical composition comprising an amount of an antagonist effective to reduce the activity of a GALR2 receptor and a pharmaceutically acceptable carrier.

This invention provides a pharmaceutical composition comprising an amount of an agonist effective to increase activity of a GALR2 receptor and a pharmaceutically acceptable carrier.

This invention provides the above-described pharmaceutical composition which comprises an amount of the antibody effective to block binding of a ligand to the GALR2 receptor and a pharmaceutically acceptable carrier.

As used herein, "pharmaceutically acceptable carriers" means any of the standard pharmaceutically acceptable carriers. Examples include, but are not limited to, phosphate buffered saline, physiological saline, water and emulsions, such as oil/water emulsions.

This invention provides a transgenic nonhuman mammal, expressing DNA encoding a GALR2 receptor.

This invention provides a transgenic nonhuman mammal comprising a homologous recombination knockout of the native GALR2 receptor.

This invention provides a transgenic nonhuman mammal whose genome comprises antisense DNA complementary to DNA encoding a GALR2 receptor so placed as to be transcribed into antisense mRNA which is complementary to mRNA encoding a GALR2 receptor and which hybridizes to mRNA encoding a GALR2 receptor thereby reducing its translation.

This invention provides the above-described transgenic nonhuman mammal, wherein the DNA encoding a GALR2 receptor additionally comprises an inducible promoter.

This invention provides the transgenic nonhuman mammal, wherein the DNA encoding a GALR2 receptor additionally comprises tissue specific regulatory elements.

In an embodiment, the transgenic nonhuman mammal is a mouse.

Animal model systems which elucidate the physiological and behavioral roles of GALR2 receptor are produced by creating transgenic animals in which the activity of the GALR2 receptor is either increased or decreased, or the amino acid sequence of the expressed GALR2 receptor is altered, by a variety of techniques. Examples of these techniques include, but are not limited to: 1) Insertion of normal or mutant versions of DNA encoding a GALR2 receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these GALR2 receptor sequences. The technique of homologous recombination is well known in the art. It replaces the native gene with the inserted gene and so is useful for producing an animal that cannot express native GALR2 receptors but does express, for example, an inserted mutant GALR2 receptor, which has replaced the native GALR2 receptor in the animal's genome by recombination, resulting in underexpression of the transporter. Microinjection adds genes to the genome, but does not remove them, and so is useful for producing an animal which expresses its own and added GALR2 receptors, resulting in overexpression of the GALR2 receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a GALR2 receptor is purified from a vector by methods well known in the art. Inducible promoters may be fused with the coding region of the DNA to provide an experimental means to regulate expression of the trans-gene. Alternatively, or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

This invention provides a process for identifying a chemical compound which specifically binds to a GALR2 receptor which comprises contacting cells containing DNA encoding and expressing on their cell surface the GALR2 receptor, wherein such cells do not normally express the GALR2 receptor, with the compound under conditions suitable for binding, and detecting specific binding of the chemical compound to the GALR2 receptor.

This invention further provides a process for identifying a chemical compound which specifically binds to a GALR2 receptor which comprises contacting a membrane fraction from a cell extract of cells containing DNA encoding and expressing on their cell surface the GALR2 receptor, wherein such cells do not normally express the GALR2 receptor, with the compound under conditions suitable for binding, and detecting specific binding of the chemical compound to the GALR2 receptor.

This invention also provides a method for determining whether a chemical compound can specifically bind to a GALR2 receptor which comprises contacting cells transfected with and expressing DNA encoding the GALR2 receptor with the compound under conditions permitting binding of compounds to such receptor, and detecting the presence of any such compound specifically bound to the GALR2 receptor, so as to thereby determine whether the compound specifically binds to the GALR2 receptor.

This invention provides a method for determining whether a chemical compound can specifically bind to a GALR2 receptor which comprises preparing a cell extract from cells transfected with and expressing DNA encoding the GALR2 receptor, isolating a membrane fraction from the cell extract, contacting the membrane fraction with the compound under conditions permitting binding of compounds to such receptor, and detecting the presence of the compound specifically bound to the GALR2 receptor, so as to thereby determine whether the compound specifically binds to the GALR2 receptor.

In one embodiment, the GALR2 receptor is a mammalian GALR2 receptor. In another embodiment, the GALR2 receptor is a rat GALR2 receptor. In still another embodiment, the GALR2 receptor has the same or substantially the sane amino acid sequence as that encoded by plasmid K985, or plasmid K1045. In still another embodiment, the GALR2 receptor has the same or substantially the same amino acid sequence as the amino acid sequence shown in FIG. 2 (SEQ ID NO: 8). In yet another embodiment, the GALR2 receptor has the amino acid sequence shown in FIG. 2 (SEQ ID NO: 8).

In another embodiment, the GALR2 receptor is a human GALR2 receptor. In still another embodiment, the human GALR2 receptor has the same or substantially the same amino acid sequence as the amino acid sequence encoded by plasmid BO29 or plasmid BO39. In yet another embodiment, the GALR2 receptor has the same or substantially the same amino acid sequence as the amino acid sequence shown in FIG. 11 (SEQ ID NO: 28). In another embodiment, the GALR2 receptor has the amino acid sequence shown in FIG. 11 (SEQ ID NO: 28).

This invention provides a process for determining whether a chemical compound is a GALR2 receptor agonist which comprises contacting cells transfected with and expressing DNA encoding the GALR2 receptor with the compound under conditions permitting the activation of the GALR2 receptor, and detecting an increase in GALR2 receptor activity, so as to thereby determine whether the compound is a GALR2 receptor agonist.

This invention provides a process for determining whether a chemical compound is a GALR2 receptor agonist which comprises preparing a cell extract from cells transfected with and expressing DNA encoding the GALR2 receptor, isolating a membrane fraction from the cell extract, contacting the membrane fraction with the compound under conditions permitting the activation of the GALR2 receptor, and detecting an increase in GALR2 receptor activity, so as to thereby determine whether the compound is a GALR2 receptor agonist.

This invention provides a process for determining whether a chemical compound is a GALR2 receptor agonist which comprises preparing a cell extract from cells transfected with and expressing DNA encoding the GALR2 receptor, isolating a membrane fraction from the cell extract, separately contacting the membrane fraction with both the chemical compound and GTPγS, and with only GTPγS, under conditions permitting the activation of the GALR2 receptor, and detecting GTPγS binding to the membrane fraction, an increase in GTPγS binding in the presence of the compound indicating that the chemical compound activates the GALR2 receptor.

In one embodiment, the GALR2 receptor is a mammalian GALR2 receptor. In another embodiment, the GALR2 receptor is a rat GALR2 receptor. In still another embodiment, the GALR2 receptor has the same or substantially the same amino acid sequence as that encoded by plasmid K985, or plasmid K1045. In still another embodiment, the GALR2 receptor has the same or substantially the same amino acid sequence as the amino acid sequence shown in FIG. 2 (SEQ ID NO: 8). In yet another embodiment, the GALR2 receptor has the amino acid sequence shown in FIG. 2 (SEQ ID NO: 8).

In another embodiment, the GALR2 receptor is a human GALR2 receptor. In still another embodiment, the human GALR2 receptor has the same or substantially the same amino acid sequence as the amino acid sequence encoded by plasmid BO29 or plasmid BO39. In yet another embodiment, the GALR2 receptor has the same or substantially the same amino acid sequence as the amino acid sequence shown In FIG. 11 (SEQ ID NO: 28). In another embodiment, the GALR2 receptor has the amino acid sequence shown in FIG. 11 (SEQ ID NO: 28)

This invention provides a process for determining whether a chemical compound is a GALR2 receptor antagonist which comprises contacting cells transfected with and expressing DNA encoding the GALR2 receptor with the compound in the presence of a known GALR2 receptor agonist, such as galanin, under conditions permitting the activation of the GALR2 receptor, and detecting a decrease in GALR2 receptor activity, so as to thereby determine whether the compound is a GALR2 receptor antagonist.

This invention provides a process for determining whether a chemical compound is a GALR2 receptor antagonist which comprises preparing a cell extract from cells transfected with and expressing DNA encoding the GALR2 receptor, isolating a membrane fraction from the cell extract, contacting the membrane fraction with the ligand in the presence of a known GALR2 receptor agonist, such as galanin, under conditions permitting the activation of the GALR2 receptor, and detecting a decrease in GALR2 receptor activity, so as to thereby determine whether the compound is a GALR2 receptor antagonist.

In one embodiment, the GALR2 receptor is a mammalian GALR2 receptor. In another embodiment, the GALR2 receptor is a rat GALR2 receptor. In still another embodiment, the GALR2 receptor has the same or substantially the same amino acid sequence as that encoded by plasmid K985, or plasmid K1045. In still another embodiment, the GALR2 receptor has the same or substantially the same amino acid sequence as the amino acid sequence shown in FIG. 2 (SEQ ID NO: 8). In yet another embodiment, the GALR2 receptor has the amino acid sequence shown in FIG. 2 (SEQ ID NO: 8).

In another embodiment, the GALR2 receptor is a human GALR2 receptor. In still another embodiment, the human GALR2 receptor has the same or substantially the same amino acid sequence as the amino acid sequence encoded by plasmid BO29 or plasmid BO39. In yet another embodiment, the GALR2 receptor has the same or substantially the same amino acid sequence as the amino acid sequence shown in FIG. 11 (SEQ ID NO: 28). In another embodiment, the GALR2 receptor has the amino acid sequence shown in FIG. 11 (SEQ ID NO: 28).

In an embodiment of the above-described methods, the cell is an insect cell. In another embodiment, the cell is a mammalian cell. In a further embodiment, the cell is non-neuronal in origin. In still further embodiments, the non-neuronal cell is a COS-7 cell, 293 human embryonic kidney cell, NIH-3T3 cell, a CHO cell, or LM(tk-) cell. In yet another embodiment of any of the processes of this invention the cell is the LM (tk-) cell L-rGALR2-8 ATCC Accession No. CRL-12074, the LM(tk-) cell L-rGALR2I-4 (ATOC Accession No. CRL-12223, or the CHO cell C-rGalR2-79 (ATCC Accession No. CRL-12262). In another embodiment of this invention the cell is the CHO cell CHO-hGALR2-264 (ATCC Accession No. CRL-12379).

In any of the above-described processes, receptor activity may be measured by assaying the binding of GTP gamma S (GTPγS) to membranes. GTPγS binding precedes the second messenger response of a G-protein coupled receptor such as the GALR2 receptors of the present invention, providing a means of measuring activation of a receptor which is independent of second messenger responses.

This invention provides a compound determined by the above-described processes. In one embodiment of the above-described processes, the compound is not previously known to bind to a GALR2 receptor.

This invention provides a GALR2 agonist determined by the above-described processes. This invention also provides a GALR2 antagonist determined by the above-described processes.

This invention provides a pharmaceutical composition which comprises an amount of a GALR2 receptor agonist effective to increase activity of a GALR2 receptor and a pharmaceutically acceptable carrier.

This invention provides a pharmaceutical composition which comprises an amount of a GALR2 receptor antagonist effective to reduce activity of a GALR2 receptor and a pharmaceutically acceptable carrier.

In further embodiments of the above-described processes, the agonist or antagonist is not previously known to bind to a GALR2 receptor.

This invention provides a process involving competitive binding for identifying a chemical compound which specifically binds to a GALR2 receptor, which comprises separately contacting cells expressing on their cell surface the GALR2 receptor, wherein such cells do not normally express the GALR2 receptor, with both the chemical compound and a second chemical compound known to bind to the receptor, and with only the second chemical compound, under conditions suitable for binding of both compounds, and detecting specific binding of the chemical compound to the GALR2 receptor, a decrease in the binding of the second chemical compound to the GALR2 receptor in the presence of the chemical compound indicating that the chemical compound binds to the GALR2 receptor.

This invention further provides a process involving competitive binding for identifying a chemical compound which specifically binds to a human GALR2 receptor, which comprises separately contacting a membrane fraction from a cell extract of cells expressing on their cell surface the GALR2 receptor, wherein such cells do not normally express the GALR2 receptor, with both the chemical compound and a second chemical compound known to bind to the receptor, and with only the second chemical compound, under conditions suitable for binding of both compounds, and detecting specific binding of the chemical compound to the GALR2 receptor, a decrease in the binding of the second chemical compound to the GALR2 receptor in the presence of the chemical compound indicating that the chemical compound binds to the GALR2 receptor.

This invention further provides a process for determining whether a chemical compound specifically binds to and activates a GALR2 receptor, which comprises contacting cells producing a second messenger response and expressing on their cell surface the GALR2 receptor, wherein such cells do not normally express the GALR2 receptor, with the chemical compound under conditions suitable for activation of the GALR2 receptor, and measuring the second messenger response in the presence and in the absence of the chemical compound, a change in the second messenger response in the presence of the chemical compound indicating that the compound activates the GALR2 receptor.

This invention further provides a process for determining whether a chemical compound specifically binds to and activates a GALR2 receptor, which comprises contacting a membrane fraction from a cell extract of cells producing a second messenger response and expressing on their cell surface the GALR2 receptor, wherein such cells do not normally express the GALR2 receptor, with the chemical compound under conditions suitable for activation of the GALR2 receptor, and measuring the second messenger response in the presence and in the absence of the chemical compound, a change in the second messenger response in the presence of the chemical compound indicating that the compound activates the GALR2 receptor.

In one embodiment of the above processes, the second messenger response comprises adenylate cyclase activity and the change in second messenger response is a decrease in adenylate cyclase activity. In one embodiment, adenylate cyclase activity is determined by measurement of cyclic AMP levels.

In another embodiment of the above processes, the second messenger response comprises arachidonic acid release and the change in second messenger response is an increase in arachidonic acid levels.

In another embodiment of the above processes, the second messenger response comprises intracellular calcium levels and the change in second messenger response is an increase in intracellular calcium levels.

In a still further embodiment of the above processes, the second messenger response comprises inositol phospholipid hydrolysis and the change in second messenger response is an increase in inositol phospholipid hydrolysis.

This invention further provides a process for determining whether a chemical compound specifically binds to and inhibits activation of a GALR2 receptor, which comprises separately contacting cells producing a second messenger response and expressing on their cell surface the GALR2 receptor, wherein such cells do not normally express the GALR2 receptor, with both the chemical compound and a second chemical compound known to activate the GALR2 receptor, and with only the second compound, under conditions suitable for activation of the GALR2 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the GALR2 receptor.

This invention further provides a process for determining whether a chemical compound specifically binds to and inhibits activation of a GALR2 receptor, which comprises separately contacting a membrane fraction from a cell extract of cells producing a second messenger response and expressing on their cell surface the GALR2 receptor, wherein such cells do not normally express the GALR2 receptor, with both the chemical compound and a second chemical compound known to activate the GALR2 receptor, and with only the second chemical compound, under conditions suitable for activation of the GALR2 receptor, and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the GALR2 receptor.

In one embodiment of the above processes, the second messenger response comprises adenylate cyclase activity and the change in second messenger response is a smaller decrease in the level of adenylate cyclase activity in the presence of both the chemical compound and the second chemical compound than in the presence of only the second chemical compound. In one embodiment, adenylate cyclase activity is determined by measurement of cyclic AMP levels.

In another embodiment of the above processes the second messenger response comprises arachidonic acid release, and the change in second messenger response is a smaller increase in arachidonic acid levels in the presence of both the chemical compound and the second chemical compound than in the presence of only the second chemical compound.

In another embodiment of the above processes the second messenger response comprises intracellular calcium levels, and the change in second messenger response is a smaller increase in intracellular calcium levels in the presence of both the chemical compound and the second chemical compound than in the presence of only the second chemical compound.

In yet another embodiment of the above processes, the second messenger response comprises inositol phospholipid hydrolysis, and the change in second messenger response is a smaller increase in inositol phospholipid hydrolysis in the presence of both the chemical compound and the second chemical compound than in the presence of only the second chemical compound.

In an embodiment of any of the above processes, the GALR2 receptor is a mammalian GALR2 receptor. In another embodiment of the above processes, the GALR2 receptor is a rat GALR2 receptor or a human GALR2 receptor. In still another embodiment of the above processes, the GALR2 receptor has the same or substantially the same amino acid sequence as encoded by the plasmid K985 ATCC Accession No. 97426), or plasmid K1045 (ATCC Accession No. 97778). In a still further embodiment of the above processes, the GALR2 receptor has the same or substantially the same amino acid sequence as that shown in FIG. 2 (SEQ ID NO: 8). In another embodiment of the above processes, the GALR2 receptor has the same or substantially the same amino acid sequence as the amino acid sequence encoded by the plasmid BO29(ATCC Accession No. 97735) or the plasmid BO39(ATCC Accession No. 97851). In a still further embodiment of the above processes, the GALR2 receptor has the same or substantially the same amino acid sequence as that shown in FIG. 11 (SEQ ID NO: 28).

In an embodiment of any of the above processes, the cell is an insect cell. In another embodiment of any of the above processes, the cell is a mammalian cell. In still further embodiments, the cell is nonneuronal in origin.

In another embodiment of the above processes, the nonneuronal cell is a COS-7 cell, Chinese hamster ovary (CHO) cell, 293 human embryonic kidney cell, NIH-3T3 cell, a mouse Y1 cell or LM(tk-) cell. In still further embodiments, nonneuronal cell is the LM(tk-) cell designated L-rGALR2-8 (ATCC Accession No. CRL-12074), the LM(tk-) cell L-rGALR2I4 (ATCC Accession No. CRL-12223,or the CHO cell C-rGalR2-79 (ATCC Accession No. CRL-12262). In another embodiment, the cell is the CHO cell CHO-hGALR2-264 (ATCC Accession No. CRL-12379).

This invention further provides a compound determined by any of the above processes. In another embodiment, the compound is not previously known to bind to a GALR2 receptor.

This invention provides a method of screening a plurality of chemical compounds not known to bind to a GALR2 receptor to identify a compound which specifically binds to the GALR2 receptor, which comprises (a) contacting cells transfected with and expressing DNA encoding the GALR2 receptor with a compound known to bind specifically to the GALR2 receptor; (b) contacting the preparation of step (a) with the plurality of compounds not known to bind specifically to the GALR2 receptor, under conditions permitting binding of compounds known to bind the GALR2 receptor; (c) determining whether the binding of the compound known to bind to the GALR2 receptor is reduced in the presence of the compounds, relative to the binding of the compound in the absence of the plurality of compounds; and if so (d) separately determining the binding to the GALR2 receptor of each compound included in the plurality of compounds, so as to thereby identify the compound which specifically binds to the GALR2 receptor.

This invention provides a method of screening a plurality of chemical compounds not known to bind to a GALR2 receptor to identify a compound which specifically binds to the GALR2 receptor, which comprises (a) preparing a cell extract from cells transfected with and expressing DNA encoding the GALR2 receptor, isolating a membrane fraction from the cell extract, contacting the membrane fraction with a compound known to bind specifically to the GALR2 receptor; (b) contacting the preparation of step (a) with the plurality of compounds not known to bind specifically to the GALR2 receptor, under conditions permitting binding of compounds known to bind the GALR2 receptor; (c) determining whether the binding of the compound known to bind to the GALR2 receptor is reduced in the presence of the compounds, relative to the binding of the compound in the absence of the plurality of compounds; and if so (d) separately determining the binding to the GALR2 receptor of each compound included in the plurality of compounds, so as to thereby identify the compound which specifically binds to the GALR2 receptor.

In an embodiment of the present invention the GALR2 receptor is a mammalian GALR2 receptor. In one embodiment of the above-described methods, the GALR2 receptor is a rat GALR2 receptor. In another embodiment, the GALR2 receptor has the same or substantially the same amino acid sequence as the amino acid sequence shown in FIG. 2 (SEQ ID NO: 8). In yet another embodiment, the GALR2 receptor has the amino acid sequence shown in FIG. 2 (SEQ ID NO: 8). In another embodiment, the GALR2 receptor is a human GALR2 receptor. In still another embodiment, the GALR2 receptor has the same or substantially the same amino acid sequence as the amino acid sequence encoded by plasmid BO29 or plasmid BO39. In another embodiment, the GALR2 receptor has the same or substantially the same amino acid sequence as the amino acid sequence shown in FIG. 11 (SEQ ID NO: 28). In yet another embodiment, the GALR2 receptor has the amino acid sequence shown in FIG. 11 (SEQ ID NO: 28).

This invention provides a method of screening a plurality of chemical compounds not known to activate a GALR2 receptor to identify a compound which activates the GALR2 receptor which comprises (a) contacting cells transfected with and expressing the GALR2 receptor with the plurality of compounds not known to activate the GALR2 receptor, under conditions permitting activation of the GALR2 receptor; (b) determining whether the activity of the GALR2 receptor is increased in the presence of the compounds; and if so (c) separately determining whether the activation of the GALR2 receptor is increased by each compound included in the plurality of compounds, so as to thereby identify the compound which activates the GALR2 receptor.

This invention provides a method of screening a plurality of chemical compounds not known to activate a GALR2 receptor to identify a compound which activates the GALR2 receptor which comprises (a) preparing a cell extract from cells transfected with and expressing DNA encoding the GALR2 receptor, isolating a membrane fraction from the cell extract, contacting the membrane fraction with the plurality of compounds not known to activate the GALR2 receptor, under conditions permitting activation of the GALR2 receptor; (b) determining whether the activity of the GALR2 receptor is increased in the presence of the compounds; and if so (c) separately determining whether the activation of the GALR2 receptor is increased by each compound included in the plurality of compounds, so as to thereby identify the compound which activates the GALR2 receptor.

In an embodiment of the above-described methods, the GALR2 receptor is a rat GALR2 receptor. In still another embodiment, the GALR2 receptor has the same or substantially the same amino acid sequence as the amino acid sequence shown in FIG. 2 (SEQ ID NO: 8). In yet another embodiment, the GALR2 receptor has the amino acid sequence shown in FIG. 2 (SEQ ID NO: 8). In another embodiment, the GALR2 receptor is a human GALR2 receptor. In still another embodiment, the GALR2 receptor has the same or substantially the same amino acid sequence as the amino acid sequence encoded by plasmid BO29 or plasmid BO39. In another embodiment, the GALR2 receptor has the same or substantially the same amino acid sequence as the amino acid sequence shown in FIG. 11 (SEQ ID NO: 28). In yet another embodiment, the GALR2 receptor has the amino acid sequence shown in FIG. 11 (SEQ ID NO: 28).

This invention provides a method of screening a plurality of chemical compounds not known to inhibit the activation of a GALR2 receptor to identify a compound which inhibits the activation of the GALR2 receptor, which comprises (a) contacting cells transfected with and expressing the GALR2 receptor with the plurality of compounds in the presence of a known GALR2 receptor agonist, under conditions permitting activation of the GALR2 receptor; (b) determining whether the activation of the GALR2 receptor is reduced in the presence of the plurality of compounds, relative to the activation of the GALR2 receptor in the absence of the plurality of compounds; and if so (c) separately determining the inhibition of activation of the GALR2 receptor for each compound included in the plurality of compounds, so as to thereby identify the compound which inhibits the activation of the GALR2 receptor.

This invention provides a method of screening a plurality of chemical compounds not known to inhibit the activation of a GALR2 receptor to identify a compound which inhibits the activation of the GALR2 receptor, which comprises (a) preparing a cell extract from cells transfected with and expressing DNA encoding the GALR2 receptor, isolating a membrane fraction from the cell extract, contacting the membrane fraction with the plurality of compounds in the presence of a known GALR2 receptor agonist, under conditions permitting activation of the GALR2 receptor; (b) determining whether the activation of the GALR2 receptor is reduced in the presence of the plurality of compounds, relative to the activation of the GALR2 receptor in the absence of the plurality of compounds; and if so (c) separately determining the inhibition of activation of the GALR2 receptor for each compound included in the plurality of compounds, so as to thereby identify the compound which inhibits the activation of the GALR2 receptor.

In an embodiment of the above-described methods, the GALR2 receptor is a rat GALR2 receptor. In another embodiment, the GALR2 receptor has the same or substantially the same amino acid sequence as the amino acid sequence shown in FIG. 2 (SEQ ID NO: 8). In yet another embodiment, the GALR2 receptor has the amino acid sequence shown in FIG. 2 (SEQ ID NO: 8). In another embodiment, the GALR2 receptor is a human GALR2 receptor. In still another embodiment, the GALR2 receptor has the same or substantially the same amino acid sequence as the amino acid sequence encoded by plasmid BO29 or plasmid BO39. In another embodiment, the GALR2 receptor has the same or substantially the same amino acid sequence as the amino acid sequence shown in FIG. 11 (SEQ ID NO: 28). In yet another embodiment, the GALR2 receptor has the amino acid sequence shown in FIG. 11 (SEQ ID NO: 28).

In one embodiment of any of the above-described methods, the activation of the GALR2 receptor is determined by a second messenger assay. In an embodiment, the second messenger assay measures adenylate cyclase activity. In other embodiments, the second messenger is cyclic AMP, intracellular calcium, or arachidonic acid, an inositol phopholipid or phosphoinositol lipid metabolite.

In one embodiment, receptor activity may be measured by assaying the binding of GTP gamma S (GTPγS) to membranes. In another embodiment, receptor activity may be measured by assaying changes in MAP kinase phosphorylation.

This invention further provides a method of measuring GALR2 receptor activation in an oocyte expression system such as a Xenopus oocyte or melanophore. In an embodiment, receptor activation is determined by measurement of ion channel activity. In another embodiment, receptor activation is measured by aequorin luminescence.

Expression of genes in Xenopus oocytes is well known in the art (A. Coleman, *Transcription and Translation: A Practical Approach* (B. D. Hanes, S. J. Higgins, eds., pp 271–302, IRL Press, Oxford, 1984; Y. Masu et al., *Nature* 329:21583–21586, 1994) and is performed using microinjection of native mRNA or in vitro synthesized mRNA into frog oocytes. The preparation of in vitro synthesized mRNA can be performed by various standard techniques (J. Sambrook et al., *Molecular Cloning: A Laboratory Manual*, Second Edition, Cold Spring Harbor Laboratory, Cold Spring Harbor, N.Y., 1989) including using T7 polymerase with the mCAP RNA capping kit (Stratagene).

In a further embodiment of the invention, the cell is a mammalian cell. In another embodiment of the invention, the mammalian cell is non-neuronal in origin. In still further embodiments of the invention, the non-neuronal cell is a COS-7 cell, a 293 human embryonic kidney cell, a mouse Y1 cell, a LM(tk-) cell, a CHO cell, or an NIH-3T3 cell. In an embodiment of the invention, the non-neuronal cell is the LM(tk-) cell designated L-rGALR2-8 (ATCC Accession No. CRL-12074), the LM(tk-) cell L-rGALR2I-4 (ATCC Accession No. CRL-12223, or the CHO cell C-rGalR2-79 (ATCC Accession No. CRL-12262). In another embodiment, the cell is the CHO cell CHO-hGALR2-264 (ATCC Accession No. CRL-12379).

This invention provides a pharmaceutical composition comprising a compound identified by the above-described methods and a pharmaceutically acceptable carrier.

In an embodiment of the above-described methods, the cell is non-neuronal in origin. In a further embodiment, the non-neuronal cell is a COS-7 cell, CHO cell, 293 human embryonic kidney cell, NIH-3T3 cell, a mouse Y1 cell or LM(tk-) cell.

In one embodiment of the above-described methods, the compound is not previously known.

This invention provides a GALR2 receptor agonist detected by the above-described methods. This invention provides a GALR2 receptor antagonist detected by the above-described methods. In an embodiment the cell is a non-mammalian cell, for example, a Xenopus oocyte or melanophore. In another embodiment the cell is a neuronal cell, for example, a glial cell line such as C6. In an embodiment, the cell is non-neuronal in origin. In a further embodiment, the cell is a Cos-7 or a CHO cell, a 293 human embryonic kidney cell, an LM(tk-) cell or an NIH-3T3 cell. In an embodiment of the invention, the LM(tk-) cell is the cell designated L-rGALR2-8 (ATCC Accession No. CRL-12074), the LM(tk-) cell L-rGALR2I-4 (ATCC Accession No. CRL-12223, or the CHO cell C-rGalR2-79 (ATCC Accession No. CRL-12262). In another embodiment, the cell is the CHO cell CHO-hGALR2-264 (ATCC Accession No. CRL-12379).

This invention provides a pharmaceutical composition comprising a drug candidate identified by the above-described methods and a pharmaceutically acceptable carrier.

This invention provides a method of detecting expression of a GALR2 receptor by detecting the presence of mRNA coding for the GALR2 receptor which comprises obtaining total mRNA from a cell or tissue sample and contacting the mRNA so obtained with the above-described nucleic acid probe under hybridizing conditions, detecting the presence of mRNA hybridized to the probe, and thereby detecting the expression of the GALR2 receptor by the cell or in the tissue.

This invention provides a method of treating an abnormality in a subject, wherein the abnormality is alleviated by administering to the subject an amount of a GALR2 selective compound, effective to treat the abnormality. Abnormalities which may be treated include cognitive disorder, pain, sensory disorder (olfactory, visual), motor coordination abnormality, motion sickness, neuroendocrine disorders, sleep disorders, migraine, Parkinson's disease, hypertension, heart failure, convulsion/epilepsy, traumatic brain injury, diabetes, glaucoma, electrolyte imbalances, respiratory disorders (asthma, emphysema), depression, reproductive disorders, gastric and intestinal ulcers, gastroesophageal reflux disorder, gastric hypersecretion, gastrointestinal motility disorders (diarrhea), inflammation, immune disorders, and anxiety. In one embodiment the compound is an agonist. In another embodiment the compound is an antagonist.

This invention provides a method of treating an abnormality in a subject, wherein the abnormality is alleviated by the inhibition of a GALR2 receptor which comprises administering to a subject an effective amount of the above-described pharmaceutical composition effective to decrease the activity of the GALR2 receptor in the subject, thereby treating the abnormality in the subject. In an embodiment, the abnormality is obesity. In another embodiment, the abnormality is bulimia.

This invention provides a method of treating an abnormality in a subject wherein the abnormality is alleviated by the activation of a GALR2 receptor which comprises administering to a subject an effective amount of the above-described pharmaceutical composition effective to activate the GALR2 receptor in the subject. In an embodiment, the abnormal condition is anorexia.

In another embodiment, the compound binds selectively to a GALR2 receptor. In yet another embodiment, the compound binds to the GALR2 receptor with an affinity greater than ten-fold higher than the affinity with which the compound binds to a GALR1 receptor. In a still further embodiment, the compound binds to the GALR2 receptor with an affinity greater than ten-fold higher than the affinity with which the compound binds to a GALR3 receptor.

This invention provides a method of detecting the presence of a GALR2 receptor on the surface of a cell which comprises contacting the cell with the above-described antibody under conditions permitting binding of the antibody to the receptor, detecting the presence of the antibody bound to the cell, and thereby detecting the presence of a GALR2 receptor on the surface of the cell.

This invention provides a method of determining the physiological effects of varying levels of activity of GALR2 receptors which comprises producing a transgenic nonhuman mammal whose levels of GALR2 receptor activity are varied by use of an inducible promoter which regulates GALR2 receptor expression.

This invention provides a method of determining the physiological effects of varying levels of activity of GALR2 receptors which comprises producing a panel of transgenic nonhuman mammals each expressing a different amount of GALR2 receptor.

This invention provides a method for identifying an antagonist capable of alleviating an abnormality wherein the abnormality is alleviated by decreasing the activity of a GALR2 receptor comprising administering a compound to the above-described transgenic nonhuman mammal and determining whether the compound alleviates the physical and behavioral abnormalities displayed by the transgenic nonhuman mammal as a result of overactivity of a GALR2 receptor, the alleviation of the abnormality identifying the compound as an antagonist.

This invention provides an antagonist identified by the above-described methods. This invention provides a pharmaceutical composition comprising an antagonist identified by the above-described methods and a pharmaceutically acceptable carrier.

This invention provides a method of treating an abnormality in a subject wherein the abnormality is alleviated by decreasing the activity of a GALR2 receptor which comprises administering to a subject an effective amount of the above-described pharmaceutical composition, thereby treating the abnormality.

This invention provides a method for identifying an agonist capable of alleviating an abnormality in a subject wherein the abnormality is alleviated by increasing the activity of a GALR2 receptor comprising administering a compound to a transgenic nonhuman mammal and determining whether the compound alleviates the physical and behavioral abnormalities displayed by the transgenic nonhuman mammal, the alleviation of the abnormality identifying the compound as an agonist.

This invention provides an agonist identified by the above-described methods.

This invention provides a pharmaceutical composition comprising an agonist identified by the above-described methods and a pharmaceutically acceptable carrier.

This invention provides a method for treating an abnormality in a subject wherein the abnormality is alleviated by increasing the activity of a GALR2 receptor which comprises administering to a subject an effective amount of the above-described pharmaceutical composition, thereby treating the abnormality.

This invention provides a method for diagnosing a predisposition to a disorder associated with the activity of a specific human GALR2 receptor allele which comprises: (a) obtaining DNA of subjects suffering from the disorder; (b) performing a restriction digest of the DNA with a panel of restriction enzymes; (c) electrophoretically separating the resulting DNA fragments on a sizing gel; (d) contacting the resulting gel with a nucleic acid probe capable of specifically hybridizing with a unique sequence included within the sequence of a nucleic acid molecule encoding a human GALR2 receptor and labelled with a detectable marker; (e) detecting labelled bands which have hybridized to DNA encoding a human GALR2 receptor labelled with a detectable marker to create a unique band pattern specific to the DNA of subjects suffering from the disorder; (f) preparing DNA obtained for diagnosis by steps a–e; and (g) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

In an embodiment, a disorder associated with the activity of a specific human GALR2 receptor allele is diagnosed. In another embodiment, the above-described method may be used to identify a population of patients having a specific GALR2 receptor allele, in which population the disorder may be alleviated by administering to the subjects a GALR2-selective compound.

This invention provides a method of preparing the purified GALR2 receptor which comprises: (a) inducing cells to express GALR2 receptor; (b) recovering the receptor from the induced cells; and (c) purifying the receptor so recovered.

This invention provides a method of preparing a purified GALR2 receptor which comprises: (a) inserting nucleic acid encoding the GALR2 receptor in a suitable vector; (b) introducing the resulting vector in a suitable host cell; (c) placing the resulting cell in suitable condition permitting the production of the isolated GALR2 receptor; (d) recovering the receptor produced by the resulting cell; and (e) purifying the receptor so recovered.

This invention provides a method of modifying feeding behavior of a subject which comprises administering to the subject an amount of a compound which is a galanin receptor agonist or antagonist effective to increase or decrease the consumption of food by the subject so as to thereby modify feeding behavior of the subject. In one embodiment, the compound is a GALR2 receptor antagonist and the amount is effective to decrease the consumption of food by the subject. In another embodiment the compound is administered in combination with food.

In yet another embodiment the compound is a GALR2 receptor agonist and the amount is effective to increase the consumption of food by the subject. In a still further embodiment, the compound is administered in combination with food. In other embodiments the subject is a vertebrate, a mammal, a human or a canine.

In one embodiment, the compound binds selectively to a GALR2 receptor. In another embodiment, the compound binds to the GALR2 receptor with an affinity greater than ten-fold higher than the affinity with which the compound binds to a GALR1 receptor. In another embodiment, the compound binds to the GALR2 receptor with an affinity greater than ten-fold higher than the affinity with which the compound binds to a GALR3 receptor. In yet another embodiment, the compound binds to the GALR2 receptor with an affinity greater than one hundred-fold higher than the affinity with which the compound binds to a GALR1 receptor. In another embodiment, the compound binds to the GALR2 receptor with an affinity greater than one hundred-fold higher than the affinity with which the compound binds to a GALR3 receptor.

This invention provides a method for determining whether a chemical compound is a GALR2 antagonist which comprises: (a) administering to an animal a GALR2 agonist and measuring the amount of food intake in the animal; (b) administering to a second animal both the GALR2 agonist and the chemical compound, and measuring the amount of food intake in the second animal; and (c) determining whether the amount of food intake is reduced in the presence of the chemical compound relative to the amount of food intake in the absence of the compound, so as to thereby determine whether the compound is a GALR2 antagonist.

This invention further provides a method of screening a plurality of chemical compounds to identify a chemical compound which is a GALR2 antagonist which comprises: (a) administering to an animal a GALR2 agonist and measuring the amount of food intake in the animal; (b) administering to a second animal the GALR2 agonist and at least one chemical compound of the plurality of compounds, and measuring the amount of food intake in the animal; (c) determining whether the amount of food intake is reduced in the presence of at least one chemical compound of the plurality of chemical compounds relative to the amount of food intake in the absence of at least one of the compounds, and if so; (d) separately determining whether each chemical compound is a GALR2 antagonist according to the method described above, so as to thereby determine if the chemical compound is a GALR2 antagonist. In one embodiment the GALR2 agonist is [D-Trp]$_2$-galanin$_{(1-29)}$. In another embodiment the animal is a non-human mammal. In a further embodiment, the animal is a rodent.

In one embodiment, the above process further comprises determining whether the compound selectively binds to the GALR2 receptor relative to another galanin receptor. In another embodiment, the determination whether the compound selectively binds to the GALR2 receptor comprises: (a) determining the binding affinity of the compound for the GALR2 receptor and for such other galanin receptor; and (b) comparing the binding affinities so determined, the presence of a higher binding affinity for the GALR2 receptor than for such other galanin receptor indicating that the compound selectively binds to the GALR2 receptor. In an embodiment, the other galanin receptor is a GALR1 receptor. In another embodiment, the other galanin receptor is a GALR3 receptor.

This invention provides a process for determining whether a compound selectively activates the GALR2 receptor relative to another galanin receptor.

This invention provides a process for determining whether a compound selectively activates the GALR2 receptor relative to another galanin receptor, wherein the determination whether the compound selectively activates the GALR2 receptor comprises: (a) determining the potency of the compound for the GALR2 receptor and for such other galanin receptor; and (b) comparing the potencies so determined, the presence of a higher potency for the GALR2 receptor than for such other galanin receptor indicating that the compound selectively activates the GALR2 receptor. In an embodiment, such other galanin receptor is a GALR1 receptor. In another embodiment, such other galanin receptor is a GALR3 receptor.

This invention provides a process for determining whether a compound selectively inhibits the activation of the GALR2 receptor relative to another galanin receptor.

This invention provides a process for determining whether a compound selectively inhibits the activation of the GALR2 receptor relative to another galanin recpetor, wherein the determination whether the compound selectively inhibits the activation of the GALR2 receptor comprises: (a) determining the decrease in the potency of a known galanin receptor agonist for the GALR2 receptor in the presence of the compound, relative to the potency of the agonist in the absence of the compound; (b) determining the decrease in the potency of the agonist for such other galanin receptor in the presence of the compound, relative to the potency of the agonist in the absence of the compound; and (c) comparing the decrease in potencies so determined, the presence of a greater decrease in potency for the GALR2 receptor than for such other galanin receptor indicating that the compound selectively inhibits the activation of the GALR2 receptor. In an embodiment, such other galanin receptor is a GALR1 receptor. In another embodiment, such other galanin receptor is a GALR3 receptor.

This invention provides a method of decreasing feeding behavior of a subject which comprises administering a compound which is a GALR2 receptor antagonist and a compound which is a Y5 receptor antagonist, the amount of such antagonists being effective to decrease the feeding behavior of the subject. In one embodiment, the GALR2 antagonist and the Y5 antagonist are administered in combination. In another embodiment, the GALR2 antagonist and the Y5 antagonist are administered once. In another embodiment, the GALR2 antagonist and the Y5 antagonist are administered separately. In still another embodiment, the GALR2 antagonist and the Y5 antagonist are administered once. In another embodiment, the galanin receptor antagonist is administered for about 1 week to 2 weeks. In another embodiment, the Y5 receptor antagonist is administered for about 1 week to 2 weeks.

In yet another embodiment, the GALR2 antagonist and the Y5 antagonist are administered alternately. In another embodiment, the GALR2 antagonist and the Y5 antagonist are administered repeatedly. In a still further embodiment, the galanin receptor antagonist is administered for about 1 week to 2 weeks. In another embodiment, the Y5 receptor antagonist is administered for about 1 week to 2 weeks.

This invention also provides a method as described above, wherein the compound is administered in a pharmaceutical composition comprising a sustained release formulation.

This invention provides a method of decreasing nociception in a subject which comprises administering to the subject an amount of a compound which is a GALR2 receptor agonist effective to decrease nociception in the subject.

This invention provides a method of treating pain in a subject which comprises administering to the subject an amount of a compound which is a GALR2 receptor agonist effective to treat pain in the subject.

This invention provides a method of treating Alzheimer's disease in a subject which comprises administering to the subject an amount of a compound which is a galanin receptor antagonist effective to treat the subject's Alzheimer's disease. In one embodiment, the galanin receptor antagonist is a GALR2 receptor antagonist and the amount of the compound is effective to treat the subject's Alzheimer's disease.

This invention provides a method of producing analgesia in a subject which comprises administering to the subject an amount of a compound which is a galanin receptor agonist effective to produce analgesia in the subject.

In another embodiment, the galanin receptor agonist is a GALR2 receptor agonist and the amount of the compound is effective to produce analgesia in the subject.

This invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Construction and Screening of a Rat Hypothalamus cDNA Library

Total RNA was prepared from rat hypothalami by a modification of the guanidine thiocyanate method (Chirgwin, 1979). Poly A$^+$ RNA was purified using a FastTrack kit (Invitrogen Corp., San Diego, Calif.). Double stranded (ds) cDNA was synthesized from 4.6 µg of poly A$^+$ RNA according to Gubler and Hoffman (1983) with minor modifications. The resulting cDNA was ligated to BstXI/EcoRI adaptors (Invitrogen Corp.) and the excess adaptors removed by exclusion column chromatography. High molecular weight fractions of size-selected ds-cDNA were ligated in pEXJ.T7 (an Okayama and Berg expression vector modified from pcEXV (Miller & Germain, 1986) to contain BstXI and other additional restriction sites and a T7 promoter (Stratagene) and electroporated in E. coli MC 1061 (Gene Pulser, Biorad). A total of 3×10$^6$ independent clones with a mean insert size of 2.2 kb were generated. The library was plated on agar plates (Ampicillin selection) in 584 primary pools of ~5,000 independent clones. After 18 hours amplification, the bacteria from each pool were scraped, resuspended in 4 mL of LB media and 0.75 mL processed for plasmid purification (QIAwell-96 ultra, Qiagen, Inc., Chatsworth, Calif.). Aliquots of each bacterial pool were stored at −85° C. in 20% glycerol.

To screen the library, COS-7 cells were plated in slide chambers (Lab-Tek) in Dulbecco's modified Eagle medium (DMEM) supplemented with 10% calf serum, 100 U/mL of penicillin, 100 ug/mL streptomycin, 2 mM L-glutamine (DMEM-C) and grown at 37° C. in a humidified 5% $CO_2$ atmosphere for 24 hours before transfection. Cells were transfected with miniprep DNA prepared from the primary pools (~4,500 cfu/pool) of the rat hypothalamus cDNA library using a modification of the DEAE-dextran method (Warden & Thorne, 1968). Pools containing GALR1 were identified by PCR prior to screening and were omitted from the primary screen. The galanin binding assay was carried out after 48 hours. Cells were rinsed twice with phosphate-buffered saline (PBS) then incubated with 1 nM $^{125}$I-porcine galanin (NEN; specific activity ~2200 Ci/mmol) in 20 mM HEPES-NaOH, pH 7.4, containing 1.26 mM $CaCl_2$, 0.81 mM MgSO$_4$, 0.44 mM KH$_2$PO$_4$, 5.4 mM KCl, 10 mM NaCl, 0.1% BSA, and 0.1% bacitracin for one hour at room temperature. After rinsing and fixation in 2.5% glutaraldehyde, slides were rinsed in PBS, air-dried, and dipped in photoemulsion (Kodak, NTB-2). After a 3–4 day exposure slides were developed in Kodak D19 developer, fixed, and coverslipped (Aqua-Mount, Lerner Laboratories), then inspected for positive cells by brightfield microscopy (Leitz Laborlux, 25× magnification). One pool with positive cells, (J126) was subdivided and rescreened repeatedly until a single colony was isolated that conferred galanin binding. The 3.8 kb cDNA is preferably sequenced on both strands using Sequenase (US Biochemical, Cleveland, Ohio) according to the manufacturer. Nucleotide and peptide sequence analyses are performed using the Wisconsin Package (GCG, Genetics Computer group, Madison, Wis.) or PC/GENE (Intelligenetics, Mountain View, Calif.).

PCR Methodology

PCR reactions were carried out in 20 μL volumes using Taq Polymerase (Boehringer Mannheim, Indianapolis, Ind.) in a buffer containing 10 mM Tris-HCl, pH 8.3, 50 mM KCl, 1.5 mM MgCl$_2$ 0.01% gelatin, 0.2 mM each dNTP, and 1 μM each PCR primer. To prescreen library pools for GALR1, two GALR1 primer sets were used (KS-1177/1178 and KS-1311/1313, see below) to determine whether GALR1 was present in original bacterial stocks of each library pool. PCR was carried out for 40 cycles of 94° C./2 min, 68 ° C./2 min, 72° C./3 min. Pools positive for GALR1 by PCR were eliminated from the library screen.

To confirm that the purified cDNA conferring galanin binding was distinct from GALR1, the isolated clone representing pool J126-10-334 (K985) was subjected to PCR analysis using three GALR1 primer sets representing different regions of GALR1. The nucleotide sequences of the primer sets are shown below:

KS-1177: 5'-TGG GCA ACA CCC TAG TGA TCA CCG-3'S (SEQ ID NO: 1) Nucleotides 146–169 of human GALR1 coding region, forward primer.

KS-1178: 5'-CTG CTC CCA GCA GAA GGT CTG GTT-3' (SEQ ID NO: 2) Nucleotides 547–570 of human GALR1 coding region, reverse primer.

KS-1311: 5'-CCT CAG TGA AGG GAA TGG GAG CGA-3' (SEQ ID NO: 3) Nucleotides 21–44 of rat GALR1 coding region, forward primer.

KS-1313: 5'-CTC ATT GCA AAC ACG GCA CIT GAA CA-3' (SEQ ID NO: 4) Nucleotides 944–969 of rat GALR1 coding region, reverse primer.

KS-1447: 5'-CTT GCT TGT ACG CCT TCC GGA AGT-3' (SEQ ID NO: 5) Nucleotides 920–943 of rat GALR1 coding region, reverse primer.

KS-1448: 5'-GAG AAC TTC ATC ACG CTG GTG GTG-3' (SEQ ID NO: 6). Nucleotides 91–114 of rat GALR1 coding region, forward primer.

Generation of Human GALR2 PCR Product

Human genomic DNA (1 μg; 12 different lots from Promega and Clontech) were amplified in 50 μl PCR reaction mixtures using the Expand Long Template PCR System (as supplied and described by the manufacturer, Boehringer Mannheim) and 1 μM of primers, using a program consisting of 40 cycles of 94° C. for 2 min, 60° C. for 2 min, and 68° C. for 3 min, with a pre- and post-incubation of 95° C. for 5 min and 68° C. for 10 min, respectively. PCR primers for hGALR2 were designed against rGALR2 sequence: forward primer NS525 in the fourth transmembrane domain, and reverse primer NS526 in the sixth transmembrane domain. The PCR products were run on a 0.8% low-melting agarose gel. The single ≃300 bp fragment from 3 different lots were isolated, purified by phenol extraction and subjected to sequencing using the T7 Sequenase PCR product sequencing kit (Amersham). Sequence was analyzed using the Wisconsin Package (GCG, Genetics Computer Group, Madison, Wis.).

5' and 3' RACE Analysis of Human GALR2

5' and 3' RACE (rapid analysis of cDNA ends) were performed on human brain and human lung RNAs (Clontech), respectively, using a Marathon cDNA Amplification Kit (Clontech). Total RNA was poly A+ selected using a FastTrack mRNA Isolation Kit (Invitrogen Corp., San Diego, Calif.). For 5' RACE, double stranded (ds) cDNA was synthesized from 1 μg Poly A+ RNA using BB 153, a reverse primer from the 5' end of the sixth transmembrane domain of hGALR2 from the PCR fragment described above. Adaptor ligation and nested PCR were performed according to the Marathon cDNA Amplification protocol using Advantage KlenTaq Polymerase (Clontech). The initial PCR reaction was performed on 1 μl of a 50 fold dilution of the ligated cDNA using the supplier's Adaptor Primer 1 and BB 154, a reverse primer from the fifth transmembrane domain of the hGALR2 PCR product above. One μl of this initial PCR reaction was re-amplified using the Adaptor Primer 2 and NS 563, a reverse primer just upstream from BB154. The conditions for PCR were 30 sec at 94° C., 4 min at 72° C. for 5 cycles, 30 sec at 94° C., 4 min at 70° C. for 5 cycles, 20 sec at 94° C., 4 min at 68° C. for 25 cycles, with a pre- and post-incubation of 1 min at 94° C. and 7 min at 68° C. respectively. A 600 base pair fragment from the nested PCR was isolated from a 1% TAE gel using a GENECLEAN III kit (BIO 101, Vista, Calif.) and sequenced using AmpliTaq DNA Polymerase, FS (Perkin Elmer). The sequence was run on an ABI PRISM 377 DNA Sequencer and analyzed using the Wisconsin Package (GCG, Genetics Computer Group, Madison, Wis.). For 3' RACE, double stranded (ds) cDNA was synthesized from 1 μg Poly A+ RNA using the cDNA synthesis primer CDS supplied with the Marathon cDNA Amplification Kit (Clontech). PCR conditions for 3' RACE were similar to 5' RACE except that BB166 and BB167, forward primers from the fifth transmembrane domain of the hGALR2 PCR fragment described above, were used in place of BB154 and NS563, respectively. A 500 base pair fragment from the nested PCR was isolated from a 1% TAE gel using a GENECLEAN III kit (BIO 101, Vista, Calif.) and sequenced as above.

Construction and Screeninq of a Human Heart cDNA Library

Poly A+ RNA was purified from human heart RNA (Clontech) using a FastTrack kit (Invitrogen, Corp.). DS~cDNA was synthesized from 8 μg of poly A+ RNA according to Gubler and Hoffman (1983) with minor modifications. The resulting cDNA was ligated to BstXI adaptors (Invitrogen, Corp.) and the excess adaptors removed by exclusion column chromatography. High molecular weight fractions of size-selected ds~cDNA were ligated in pEXJ.BS, an Okayama and Berg expression vector modified from pcEXV (Miller and Germain, 1986) to contain BstXI and other additional restriction sites. A total of 4.45×10$^6$ independent clones with a mean insert size of 2.5 kb were generated. The library was plated on agar plates (Ampicillin selection) in 127 primary pools; 50 pools with 37,500 independent clones, 51 pools with 25,000 clones and 26 pools with 50,000 clones. Glycerol stocks of the primary pools were combined in 16 superpools of 8 and screened for hGALR2 by PCR using primers BB153 and BB169, a forward primer from the second intracellular domain of hGALR2 identified in the 5' RACE fragment above. PCR was performed with the Expand Long Template PCR System (Boehringer Mannheim) under the following conditions: 1 min at 94° C., 4 min at 68° C. for 40 cycles, with a pre- and post-incubation of 5 min at 95° C. and 7 min at 68° C., respectively. Primary pools from positive superpools were screened by PCR and then primary pool 169 was subdivided and screened by PCR. One positive subpool, 69-11, was subdivided into 20 pools of 1200 clones plated on agar plates (ampicillin selection) Colonies were transferred to nitrocellulose membranes (Schleicher and Schuell, Keene, N.H.), denatured in 0.4 N NaOH, 1.5 M NaCl, renatured in 1M Tris, 1.5 M NaCl, and UV cross-linked. Filters were hybridized overnight at 40° C. in a buffer containing 50% formamide, 5×SSC, 7 mM TRIS, 1×Denhardt's solution and 25 µg/ml salmon sperm DNA (Sigma Chemical Co.) and $10^6$ cpm/ml of KS1567, an oligonucleotide probe from the 3' end of the fifth transmembrane domain of hGALR2, labeled with γ-32P[ATP] (6000 Ci/mmol, NEN) using polynucleotide kinase (Boehringer Mannheim). Filters were washed 2×15 minutes at room temperature in 2×SSC, 0.1% SDS, 2×15 minutes at 50° C. in 0.1×SSC, 0.1% SDS, and exposed to XAR X-ray film (Kodak) for 3 days. Colonies which appeared to hybridize were re-screened by PCR using primers BB167 and BB170, a reverse primer from the COOH terminus of hGlR2 identified by the 3' RACE fragment above. PCR was performed with the Expand Long Template PCR System (Boehringer Mannheim) under the following conditions: 1 min at 94° C., 2 min at 58° C., 2 min at 68° C. for 28 cycles, with a pre- and post-incubation of 5 min at 95° C. and 7 min at 68° C. respectively. One positive colony, 69-11-5 was amplified overnight in 10 ml LB media and processed for plasmid purification using a standard alkaline lysis miniprep procedure followed by a PEG precipitation. To ensure that 69-11-5 was a single colony, it was amplified for 3 hours in 3 ml of LB media and then 1 µl of a 1:100 dilution was plated on an agar plate. Twenty colonies were screened by PCR using primers BB167 and BB170 using the same conditions as above, except that 25 cycles were used instead of 28. One positive single colony, 69-11-5-3, designated BO29, was amplified overnight in 10 ml of TB media and processed for plasmid purification. Vector-anchored PCR was performed on BO29 using the Expand Long Template PCR System (Boehringer Mannheim) to determine the orientation and size of the insert. BB173 and BB172, forward and reverse vector primers, respectively, were used with primers BB169 and BB153. The conditions for PCR were 1 min at 94° C., 4 min at 68° C. for 36 cycles, with a pre- and post-incubation of 5 min at 95° C. and 7 min at 68° C. respectively. BO29 is preferably sequenced on both strands using AmpliTaq DNA Polymerase, FS (Perkin Elmer). The sequence is run on an ABI PRISM 377 DNA Sequencer and analyzed using the Wisconsin Package (GCG, Genetics Computer Group, Madison, Wis.).

To test the ability of 69-11-5 to confer galanin binding, COS-7 cells were plated in slide chambers (Lab-Tek) in Dulbecco's modified Eagle medium (DMEM) supplemented with 10% calf serum, 100 U/ml of penicillin, 100 µg/ml streptomycin, 2 mM L-glutamine (DMEM-c) and grown at 37° C. in a humidified 5% $CO_2$ atmosphere for 24 hours before transfection. Cells were transfected with 1 µg of miniprep DNA from 69-11-5 or vector control using a modification of the DEAE-dextran method (Warden and Thorne, 1968). 48 hours after transfection, cells were rinsed with phosphate-buffered saline (PBS) then incubated with 1 nM $^{125}$I-rat galanin (NEN; specific activity ~2200 Ci/mmol) and 2 nM $^{125}$I-porcine galanin (NEN; specific activity ~2200 Ci/mmol) in 20 mM HEPES-NaOH, pH 7.4, containing 1.26 mM $CaCl_2$, 0.81 mM $MgSO_4$, 0.44 mM $KH_2PO_4$, 5.4 mM KCl, 10 mM NaCl, 0.1% BSA, and 0.1% bacitracin for one hour at room temperature. After rinsing and fixation in 2.5% glutaraldehyde, slides were rinsed in PBS, air-dried, and dipped in photoemulsion (Kodak, NTB-2). After a 4-day exposure, slides were developed in Kodak D19 developer, fixed, and coverslipped (Aqua-Mount, Lerner Laboratories), then inspected for positive cells by brightfield microscopy (Leitz Laborlux, 25× magnification). To test the ability of the single clone BO29 to confer galanin binding, BO29 or control vector were transfected into COS-7 cells for testing of $^{125}$I galanin as described above, with the exception that after fixation, binding of $^{125}$I galanin to cells on the slide was detected using an $^{125}$I probe (Mini-Instruments, Ltd., Essex, England). The signal from BO29 transfected cells was compared with the signal from control vector transfected cells.

Primers and Probes Used

| | | |
|---|---|---|
| NS525: | 5' CCCTACCTGAGCTACTACCGTCA 3'; | (SEQ ID NO:13) |
| NS526: | 5' ACCAAACCACACGCAGAGGATAAG 3'; | (SEQ ID NO:14) |
| BB153: | 5'-CCACGATGAGGATCATGCGTGTCACC-3'; | (SEQ ID NO:15) |
| BB154: | 5'-TAGGTCAGGCCGAGAACCAGCACAGG-3'; | (SEQ ID NO:16) |
| NS563: | 5'-CAGGTAGCTGAAGACGAAGGTGCA-3'; | (SEQ ID NO:17) |
| BB166: | 5'-CTGCACCTTCGTCTTCAGCTACCTG-3'; | (SEQ ID NO:18) |
| BE167: | 5'-CCTGTGCTGGTTCTCGGCCTGACCTA-3'; | (SEQ ID NO:19) |
| BB169: | 5'-TATCTGGCCATCCGCTACCCGCTGCA-3'; | (SEQ ID NO:20) |
| KS1567: | 5'-TTGCGCTACCTCTGGCGCGCCGTCGACCCGGTGGCCGCGGGCTCG-3'; | (SEQ ID NO:21) |
| BB170: | 5'-CCAACAATGACTCCAACTCTGTGAC-3'; | (SEQ ID NO:22) |
| BB173: | 5'-AGGCGCAGAACTGGTAGGTATGGAA-3'; and | (SEQ ID NO:23) |
| BB172: | 5'-AAGCTTCTAGAGATCCCTCGACCTC-3'. | (SEQ ID NO:24) |

Generation of an Intronless Human GALR2 Receptor

Human tissues may be screened by-PCR, using primers that cross the intron, to identify cDNA sources that express the intronless form. An intronless hGALR2 clone may be obtained using an approach similar to that used to obtain an intronless rGALR2 clone (infra). Alternatively, one may use restriction enzymes to remove the intron and some adjacent coding region from BO29, and then replace the removed coding region by inserting a restriction enzyme-digested PCR fragment amplified from a tissue shown to express the intronless form of the receptor.

Human hippocampus and human hypothalamus were each shown to express the intronless form. A full-length, intronless human GALR2 PCR product was amplified from human hippocampus, but was found to contain a single point mutation downstream from the intron splice site. Therefore, an EcoRI/StyI restriction digest fragment, containing 11 bp of 5'UT and the first 557 bp of hGalR2 coding region, was ligated to a StyI restriction digest fragment, containing bp 558–1164 of the coding region and 182 bp of 3' UT, which was isolated from the intron-containing hGALR2 clone (BO29). The ligation product, comprising the entire intronless form of the human GALR2 receptor, was subcloned into the vector pEXJ and designated BO39 (ATCC Accession No. 97851).

RT PCR of rat brain tissues was carried out using total or poly A$^+$ RNA (1.5 μg or 0.5 μg, respectively) isolated from various rat brain regions and converted to cDNA using Superscript II (BRL, Gaithersburg, Md.) reverse transcriptase with random priming. The cDNAs were used as templates for PCR amplification of GALR2 using specific GALR2 primers. PCR products were separated on an agarose gel by electrophoresis and blotted to a charged nylon membrane.

RT-PCR of human tissues was carried out using cDNAs prepared from total RNA as described above (using hippocampal, hypothalamic, heart, kidney, liver, lung and retinal RNAs purchased from Clontech, Palo Alto, Calif.) or using cDNAs purchased from Clontech (for cerebral cortex, adrenal gland, lymph node, small intestine, spleen and stomach tissues). The primers used were BB182 (reverse primer from hGALR2 stop codon) and BB183 (forward primer from hGALR2 start codon). The PCR products were Southern blotted and hybridized with a $^{32}$P-labeled oligonucleotide probe, BB247.

Primers and Probe Sequences:

```
BB182: 5'-TCGTAATAGAAGCTTGGCCACATCAACCGTCAGGATGCTG-3'           (SEQ ID NO:31)

BB183: 5'-TATCGATAGGAATTCAGCGGCACCATGAACGTCTCGGGCT-3'; and      (SEQ ID NO:32)

BB247: 5'-ATCGTTTACGCGCTGGTCTCCAACCACTTCCGCAAAGGCTTCCGCACGAT-3'.  (SEQ ID NO:33)
```

Northern Blots

Human brain multiple tissue northern blots (MTN blots II and III, Clontech, Palo Alto, Calif.) carrying mRNA purified from various human brain areas may be hybridized according to the manufacturers' specifications.

Rat multiple tissue northern blots including multiple brain tissue blots (rat MTN blot, Clontech, Palo Alto, Calif.) carrying mRNA purified from various rat tissues also may be hybridized at high stringency according to the manufacturer's specifications.

RT-PCR Analyses of GALR2 mRNA

Tissues may be homogenized and total RNA extracted using the guanidine isothiocyanate/CsCl cushion method. RNA may then be treated with DNase to remove any contaminating genomic DNA. cDNA may be prepared from total RNA with random hexanucleotide primers using the reverse transcriptase Superscript II (BRL, Gaithersburg, Md.). First strand cDNA (about 250 ng of total RNA) may be amplified for example, in a 50 μL PCR reaction mixture (200 μM dNTPs final concentration) and 1 AM appropriate primers, using an appropriate thermal cycling program.

The PCR products may be run on a 1.5% agarose gel and transferred to charged nylon membranes (Zetaprobe GT, BioRad), and analyzed as Southern blots. GALR2 primers will be screened for the absence of cross-reactivity with the other galanin receptors. Filters may be hybridized with radiolabeled probes and washed under high stringency. Labeled PCR products may be visualized on X-ray film. Similar PCR and Southern blot analyses may be conducted with primers and probes, e.g., 1B15, directed to the housekeeping gene, glyceraldehyde phosphate dehydrogenase (Clontech, Palo Alto, Calif.), to normalize the amount of cDNA used from the different tissues.

Isolation of the Intronless Rat GALR2 RT-PCR analysis of various rat brain regions (FIG. 5) was carried out using primers representing N- and C-termnini of rat GALR2 (supra). The forward and reverse primers cognrised nucleotides 1–23 and 1087–1110, respectively, of the intronless rat GALR2 segnence (SEQ ID NO: 7). The BCR products were separated by agarose gel electrophoresis, blotted, and hybridized with an oligonucleotide probe designed to the predicted 5/6 loop of GALR2 (nucleotides 651–695, SEQ ID NO: 7). This analysis indicated the presence of both introncontaining and intronless forms of rat GALR2 in brain. In order to choose an appropriate tissue source from which to isolate the intronless form, a similar POR analysis on RNA from a variety of rat tissues was carried out. Based on the size of the products determined by agarose gel electrophoresis (data not shown), rat heart was chosen as a potential source of intronfess GALR2 RNA. To isolate the intronless GALR2, PCR primers similar to those used above but containing restriction enzyme sites to facilitate subcloning and a Kozak consensus for translation initiation (KS-1550 and KS-1551, see below) were used to anplify rat GALR2 from rat heart ENA by PCR (after conversion of the RNA to first strand cDNA by standard methods). A PCR product of the correct size was isolated frcm an agarose gel and then reamplified using the same primers to increase yield. The products were digested with the appropriate restriction enzymes to produce cohesive ends (EcoRI and Xba I), ligated into the expression vector EXJ.RH and transformed into E.Coli. The resulting colonies were transferred to nitrocellulose membranes and hybridized with an oligonucleotide probe to the predicted ⅔ loop of rat GALR2 (nucleotides 259–303, SEQ ID NO: 7). A single hybridizing colony was found by subsequent analysis to contain the intronless rat GALR2 cDNA.

Primers Used:

Forward primer, KS-1550: 5'-ACGGAATTCGACAT-GAATGGCTCCGGCA (SEQ ID NO: 25)

Reverse Primer, KS-1551:
5'-GCTCTAGAGCCCCTTTGGTCCTTTAACAAGCCGG (SEQ ID NO: 26)

Production of Recombinant Baculovirus

The coding region of GALR2 may be subcloned into pBlueBacIII into existing restriction sites, or sites engineered into sequences 5' and 3' to the coding region of GALR2, for example, a 5' BamHI site and a 3' EcoRI site. To generate baculovirus, 0.5 µg of viral DNA (BaculoGold) and 3 µg of GALR2 construct may be co-transfected into $2 \times 10^6$ Spodoptera frugiperda insect Sf9 cells by the calcium phosphate co-precipitation method, as outlined in by Pharmingen (in "Baculovirus Expression Vector System: Procedures and Methods Manual"). The cells then are incubated for 5 days at 27° C.

The supernatant of the co-transfection plate may be collected by centrifugation and the recombinant virus plaque purified. The procedure to infect cells with virus, to prepare stocds of virus and to titer the virus stocks are as described in Pharmingen's manual.

Cell Culture

COS-7 cells are grown on 150 mm plates in DMEM with suppliments (Dulbecco's Modified Eagle Medium with 10% bovine calf serum, 4 mM glutamine 100 units/mL penicillin/100 µg/mL streptomycin) at 37° C., 5% $CO_2$. Stock plates of COS-7 cells are trypsinized and split 1:6 every 3–4 days. Human embryonic kidney 293 cells are grown on 150 mm plates in DMEM with supplements (10% bovine calf serum, 4 mM glutamine, 100 units/mL penicillin/100µg/mL streptomycin) at 37° C., 5% $CO_2$. Stock plates of 293 cells are trypsinized and split 1:6 every 3–4 days. Mouse fibroblast LM(tk-) cells are frown on 150 mm plates in D-MEM with supplements (Dulbecco's Modified Eagle Medium with 10% bovine calf serum, 4 mM glutamine, 100 units/mL penicillin/100 µg/mL streptomycin) at 37° C., 5% $CO_2$. Stock plates of LM(tk-) cells are trypsinized and split 1:10 every 3–4 days. Chinese hamster ovary (CHO) cells were grown on 150 mm plates in HAM's F-12 medium with supplements (10% bovine calf serum, 4 mM L-glutamine and 100 units/mL penicillin/100 ug/ml streptomycin) at 37° C., 5% CO2. Stock plates of CHO cells were trypsinized and split 1:8 every 3–4 days.

LM(tk-) cells stably transfected with the GALR2 receptor may be routinely converted from an adherent monolayer to a viable suspension. Adherent cells are harvested with trypsin at the point of confluence, resuspended in a minimal volume of complete DMEM for a cell count, and further diluted to a concentration of $10^6$ cells/mL in suspension media (10% bovine calf serum, 10% 10x Medium 199 (Gibco), 9 mM $NaHCO_3$, 25 mM glucose, 2 mM L-glutamine, 100 units/mL penicillin/100 µg/mL streptomycin, and 0.05% methyl cellulose). Cell suspensions are maintained in a shaking incubator at 37° C., 5% $CO_2$ for 24 hours. Membranes harvested from cells grown in this manner may be stored as large, uniform batches in liquid nitrogen. Alternatively, cells may be returned to adherent cell culture in complete DMEM by distribution into 96-well microtiter plates coated with poly-D-lysine (0.01 mg/mL) followed by incubation at 37° C., 5% $CO_2$ for 24 hours. Cells prepared in this manner generally yield a robust and reliable response in cAMP radio-immunoassays as further described hereinbelow.

Mouse embryonic fibroblast NIH-3T3 cells are grown on 150 mm plates in Dulbecco's Modified Eagle Medium (DMEM) with supplements (10% bovine calf serum, 4 mM glutamine, 100 units/mL penicillin/100 µg/mL streptomycin) at 37° C., 5% CO2. Stock plates of NIH-3T3 cells are trypsinized and split 1:15 every 3–4 days.

Sf9 and Sf21 cells are grown in monolayers on 150 mm tissue culture dishes in TMN-FH media supplemented with 10% fetal calf serum, at 27° C., no $CO_2$. High Five insect cells are grown on 150 mm tissue culture dishes in Ex-Cell 400™ medium supplemented with L-Glutamine, also at 27° C., no $CO_2$.

Transfection

All receptor subtypes studied may be transiently transfected into COS-7 cells by the DEAE-dextran method, using 1 µg of DNA/$10^6$ cells (Cullen, 1987). In addition, Schneider 2 Drosophila cells may be cotransfected with vectors containing the receptor gene, under control of a promoter which is active in insect cells, and a selectable resistance gene, eg., the G418 resistant neomycin gene, for expression of the galanin receptor.

Stable Transfection

The GALR2 receptor may be co-transfected with a G-418 resistant gene into the human embryonic kidney 293 cell line by a calcium phosphate transfection method (Cullen, 1987). GALR1 receptors were expressed in cells using methods well-known in the art. Stably transfected cells are selected with G-418. GALR2 receptors may be similarly transfected into mouse fibroblast LM(tk-) cells, Chinese hamster ovary (CHO) cells and NIH-3T3 cells. Transfection of LM(tk-) cells with the plasmid K985 and subsequent selection with G-418 resulted in the LM(tk-) cell line L-rGALR2-8 (ATCC Accession No. CRL-12074), which stably expresses the rat GALR2 receptor. A similar procedure was used to transfect LM(tk-) cells with plasmid K1045 (intronless rat GALR2 receptor construct) resulting in the LM(tk-) cell line L-rGALR4-I (ATCC Accession No. CRL-12223). In addition, this procedure was used to transfect CHO cells with an intron-containing plasmid to create a stably expressing rat GALR2 CHO cell line, C-rGalR2-79 (ATCC Accession No. CRL-12262). Transfection of CHO cells with the (intronless) plasmid BO39 and subsequent selection with G-418 resulted in the cell line CHO-hGALR2-264 (ATCC Accession No. CRL-12379), which stably expresses the human GALR2 receptor.

Radioligand Binding Assays

Transfected cells from culture flasks were scraped into 5 ml of Tris-HCl, 5 mM EDTA, pH 7.5, and lysed by sonication. The cell lysates were centrifuged at 1000 rpm for 5 min. at 4° C., and the supernatant was centrifuged at 30,000×g for 20 min. at 4° C. The pellet was suspended in binding buffer (50 mM Tris-HCl, 5 mM $MgSO_4$, 1 mM EDTA at pH 7.5 supplemented with 0.1% BSA, 2 µg/ml aprotinin, 0.5 mg/ml leupeptin, and 10 g/ml phosphoramidon). Optimal membrane suspension dilutions, defined as the protein concentration required to bind less than 10% of the added radioligand, were added to 96-well polpropylene microtiter plates containing $^{125}$I-labeled peptide, non-labeled peptides and binding buffer to a final volume of 250 µl. In equilibrium saturation binding assays membrane preparations were incubated in the presence of increasing concentrations (0.1 nM to 4 nM) of [$^{125}$I]porcine galanin (specific activity 2200 Ci/mmol) The binding affinities of the different galanin analogs were determined in equilibrium competition binding assays, using 0.1 nM [$^{125}$I]porcine galanin in the presence of twelve different concentrations of the displacing ligands. Binding reaction mixtures were incubated for 1 hr at 30° C., and the reaction was stopped by filtration through GF/B filters treated with 0.5% polyethyleneimine, using a cell harvester. Radioactivity was measured by scintillation counting and data were analyzed by a computerized non-linear regression program. Non-specific binding was defined as the amount of radioactivity remaining after incubation of membrane protein in the presence of 100 nM of unlabeled porcine galanin. Protein concentration was measured by the Bradford method using Bio-Rad Reagent, with bovine serum albumin as a standard.

Binding assays involving the rat GALR3 receptor are conducted at room temperature for 120 min. in binding buffer. Leupeptin, aprotonin and phosphoramidon are omitted from rat GALR3 assays while bacitracin is added to 0.1%. Nonspecific binding is defined in the presence of 1 μM porcine galanin. Cells transiently or stably expressing GALR3 receptors are produced using transfection methods which are well-known in the art, examples of which are provided herein (supra). The rat GALR3 receptor may be expressed using plasmid K1086, deposited on Oct. 8, 1996, with the ATCC, 12301 Parklawn Drive, Rockville, Md. 20852, U.S.A under the Budapest Treaty on the International Recognition of the Deposit of Microorganisms for the Purposes of Patent Procedure, and was accorded ATCC Accession No. 97747. Another plasmid expressing the rat GALR3 receptor is plasmid pEXJ-rGALR3t, deposited with the ATCC under the Budapest Treaty on Dec. 17, 1996, and accorded ATCC Accession No. 97826. The human GALR3 receptor may be expressed using plasmid pEXJ-hGALR3, also deposited with the ATCC under the Budapest Treaty on Dec. 17, 1996, and accorded ATCC Accession No. 97827. Cells stably expressing the GALR3 receptors may be used in functional assays well known in the art, examples of which are provided herein (infra).

Functional Assays

Cyclic AMP (cAMP) Formation

The receptor-mediated inhibition of cyclic AMP (cAMP) formation may be assayed in LM(tk−), CHO or 293 cells expressing the rat GALR1 and GALR2 receptors. Cells were plated in 96-well plates and incubated in Dulbecco's phosphate buffered saline (PBS) supplemented with 10 mM HEPES, 5 mM theophylline, 2 μg/ml aprotinin, 0.5 mg/ml leupeptin, and 10 μg/ml phosphoramidon for 20 min at 37° C., in 5% $CO_2$. Galanin or the test compounds were added and incubated for an additional 10 min at 37° C. The medium was aspirated and the reaction was stopped by the addition of 100 mM HCl. The plates were stored at 4° C. for 15 min, and the cAMP content in the stopping solution was measured by radioimmunoassay. Radioactivity was quantified using a gamma counter equipped with data reduction software.

Functional assay experiments were also performed using stably transfected cells seeded into 96-well microtiter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1% bovine serum albumin plus 5 mM theophylline and pre-equilibrated in the same solution for 20 min at 37° C. in 5% $CO_2$. Cells were then incubated 5 min with 10 μM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microtiter plate (Millipore, Bedford, Mass.). Filters were punched and counted for $^{125}$I in a Packard gamma counter. Functional studies of the rat GALR1 receptor in LMTK—cells were performed as previously described above except that leupeptin, aprotinin and phosphoramidon were omitted from the assay, and cells were stimulated with forskolin plus peptides for a period of 5 min.

Arachidonic Acid Release

CHO cells stably transfected with the rat GALR2 receptor were seeded into 96 well plates and grown for 3 days in HAM's F-12 with supplements. $^3$H-arachidonic acid (specific activity=0.75 uCi/ml) was delivered as a 100 ul aliquot to each well and samples were incubated at 37° C., 5% $CO_2$ for 18 hours. The labeled cells were washed three times with 200 ul HAM's F-12. The wells were then filled with medium (200 uL) and the assay was initiated with the addition of peptides or buffer (22 uL). Cells were incubated for 30 min at 37° C., 5 $CO_2$. Supernatants were transferred to a microtiter plate and evaporated to dryness at 75° C. in a vacuum oven. Samples were then dissolved and resuspended in 25 uL distilled water. Scintillant (300 uL) was added to each well and samples were counted for $^3$H in a Trilux plate reader. Data were analyzed using nonlinear regression and statistical techniques available in the GraphPAD Prism package (San Diego, Calif.).

Intracellular Calcium Mobilization

The intracellular free calcium concentration may be measured by microspectroflourometry using the fluorescent indicator dye Fura-2/AM (Bush et al. 1991). Stably transfected cells are seeded onto a 35 mm culture dish containing a glass coverslip insert. Cells are washed with HBS and loaded with 100 μL of Fura-2/AM (10 μM) for 20 to 40 min. After washing with HBS to remove the Fura-2/AM solution, cells are equilibrated in HBS for 10 to 20 min. Cells are then visualized under the 40× objective of a Leitz Fluovert FS microscope and fluorescence emission is determined at 510 nM with excitation wavelengths alternating between 340 nM and 380 nM. Raw fluorescence data are converted to calcium concentrations using standard calcium concentration curves and software analysis techniques.

Phosphoinositide Metabolism

LM(tk−) cells stably expressing the rat GALR2 receptor cDNA were plated in 96-well plates and grown to confluence. The day before the assay the growth medium was changed to 100 μl of medium containing 1% serum and 0.5 μCi [$^3$H]myo-inositol, and the plates were incubated overnight in a $CO_2$ incubator (5% $CO_2$ at 37° C.). Alternatively, arachidonic acid release may be measured if [$^3$H]arachidonic acid is substituted for the [$^3$H]myo-inositol. Immediately before the assay, the medium was removed and replaced by 200 μL of PBS containing 10 mM LiCl, and the cells were equilibrated with the new medium for 20 min. During this interval cells were also equilibrated with the antagonist, added as a 10 μL aliquot of a 20-fold concentrated solution in PBS. The [$^3$H]inositol-phosphates accumulation from inositol phospholipid metabolism was started by adding 10 μL of a solution containing the agonist. To the first well 10 μL were added to measure basal accumulation, and 11 different concentrations of agonist were assayed in the following 11 wells of each plate row. All assays were performed in duplicate by repeating the same additions in two consecutive plate rows. The plates were incubated in a $CO_2$ incubator for 1 hr. The reaction was terminated by adding 15 μl of 50% v/v trichloroacetic acid (TCA), followed by a 40 min. incubation at 4° C. After neutralizing TCA with 40 μl of 1M Tris, the content of the wells was transferred to a Multiscreen HV filter plate (Millipore) containing Dowex AG1-X8 (200–400 mesh, formate form). The filter plates were prepared adding 200 μL of Dowex AG1-X8 suspension (50% v/v, water: resin) to each well. The filter plates were placed on a vacuum manifold to wash or elute the resin bed. Each well was washed 2 times with 200 AL of water, followed by 2×200 μL of 5 mM sodium tetraborate/60 mM ammonium formate. The [$^3$H]IPs were eluted into empty 96-well plates with 200 μl of 1.2 M ammonium formate/0.1 formic acid. The content of the wells was added to 3 mls of scintillation cocktail, and the radioactivity was determined by liquid scintillation counting.

GTPγS Functional Assay

Membranes from cells transfected with the rat GalR2 receptor were suspended in assay buffer (50 mM Tris, 100 mM NaCl, 5 mM $MgCl_2$, pH 7.4) supplemented with 0.1% BSA, 0.1% bacitracin and 10 μM GDP. Membranes were incubated on ice for 20 minutes, transferred to a 96-well Millipore microtiter GF/C filter plate and mixed with GTPγ$^{35}$S (250,000 cpm/sample, specific activity ~1000 Ci/mmol) plus or minus GTPγS (final concentration=100 μM). Final membrane protein concentration=90 μg/mL. Samples were incubated in the presence or absence of porcine galanin (final concentration=1 μM) for 30 min. at room temperature, then filtered on a Millipore vacuum manifold and washed three times with cold assay buffer. Samples collected in the filter plate were treated with scintillant and counted for $^{35}$S in a Trilux (Wallac) liquid scintillation counter.

MAP Kinase Assay

CHO cells expressing either the rat GALR2 receptor or the human GALR2 receptor were plated at ~50% confluence into 6 well-plates and grown in culture with fetal bovine serum reduced to 0.5% for 2 days. Fresh medium was exchanged for old and then aspirated after 2 hrs. The assay was initiated by adding fresh medium plus or minus 1 uM human galanin for 10 minutes. Cells were washed with phosphate buffered saline and lysed in 100 uL Laemmli sample buffer (Bio-Rad) containing 5% β-mercaptoethanol. Cell lysate was scraped off the plate, transferred to a microfuge tube on ice, and sonicated for 10–15 seconds. Samples were heated at 100° C. for 3–5 minutes. Insoluble material was collected by centrifugation at 10,000×g for 5 min. Supernatant (20 μL/lane) was loaded onto a 4–20% polyacrylamide Bio-Rad Ready-Gel (10×10 cm) together with a phospho-MAP kinase protein standard (New England BioLabs) and molecular weight markers. Proteins were fractionated by SDS-PAGE (sodium dodecyl sulfate polyacrylamide gel electrophoresis) and transferred by electrophoresis to a PVDF membrane (Bio-Rad). The membrane was blocked with 5% nonfat dry milk. Phosphorylated MAP kinase was labeled with a rabbit anti-phospho-MAP kinase antibody (New England New England BioLabs) and HRP-conjugated goat anti-rabbit IgG according to standard western blot procedure. The phospho-MAP kinase complex was detected by chemiluminescence using Lumiglow reagent (New England BioLabs) and Kodak X-Omat film, with exposure times ranging from 10 to 120 seconds.

Functional assays using GALR3 receptors are performed similarly.

It is to be understood that the cell lines described herein are merely illustrative of the methods used to evaluate the binding and function of the galanin receptors of the present invention, and that other suitable cells may be used in the assays described herein.

Functional Responses in Oocytes Expressing GalR2

Female *Xenopus laevis* (Xenopus-1, Ann Arbor, Mich.) were anesthetized in 0.2% tricain (3-aminobenzoic acid ethyl ester, Sigma Chemical Corp.) and a portion of ovary was removed using aseptic technique (Quick and Lester, 1994) oocytes were defolliculated using 2 mg/ml collagenase (Worthington Biochemical Corp., Freehold, N.J.) in a solution containing 87.5 mM NaCl, 2 mM KCl, 2 mM $MgCl_2$ and 5 mM HEPES, pH 7.5. Oocytes were injected (Nanoject, Drummond Scientific, Broomall, Pa.) with 50 nL of rat GALR2 mRNA or other mRNA for use as a negative control. RNA was prepared by linearization of the plasmid (pBluescript) containing the entire coding region of the GALR2 cDNA, followed by in vitro transcription using the T7 polymerase ("MessageMachine", Ambion). Alternatively, mRNA may be translated from a template generated by PCR, incorporating a T7 promoter. Oocytes were incubated at 16° on a rotating platform for 3–8 days post-injection. Dual electrode voltage clamp ("GeneClamp", Axon Instruments Inc., Foster City, Calif.) was performed using 3 M KCl-filled glass microelectrodes having resistances of 1–3 Mohms. Unless otherwise specified, oocytes were clamped at a holding potential of −80 mV. During recordings, oocytes are bathed in continuously flowing (2–5 ml/min) medium containing 96 mM NaCl, 2 mM KCl, 2 mM $CaCl_2$, 2 mM $MgCl_2$, −5 mM HEPES, pH 7.5 (ND96). Drugs are applied by switching from a series of gravity fed perfusion lines.

Aeguorin Assays of Calcium Mobilization in Oocytes

Aequorin assays are performed by injecting oocytes with 74 ng of recombinant aequorin protein (Molecular Probes, Inc.) two or three days after the initial injection with (for example) rGALR2 mRNA. One day later the oocytes are incubated at room temperature, in the dark, in 5 μM coelenterazine (Molecular Probes) for 4 hours. Oocytes are placed individually in the well of a microtiter dish and stimulated with porcine galanin at a final concentration of 100 nM. Luminescence is measured over a two minute interval using a Dynex MLX luminometer. Values are reported in relative light units and represent a summation of the luminescence over that time period.

The human GALR2 receptor and GALR3 receptors may be studied functionally using similar methods.

For functional studies of GALR3 in *Xenopus* oocytes, oocytes were prepared as above, except that the oocytes were defolliculated using 3 mg/ml collagenase. Oocytes were injected (Nanoject, Drummond Scientific, Broomall, Pa.) 24 h later with 50–70 nL of individual mRNAs or mRNA mixtures (see below).

Genes encoding G-protein inwardly rectifying K+ channels 1 and 4 (GIRK1 and GIRK4) were obtained by PCR using the published sequences (Kubo et al., 1993; Dascal et al., 1993; Krapivinsky et al., 1995) to derive appropriate 5' and 3' primers. Human heart cDNA was used as template together with the primers 5'-CGCGGATCCATTATGTCTGCACTCCGAAGGA AATTTG-3' (SEQ ID NO: 34) and 5'-CGCGAATTCTTATGTGAAGCGATCAGAGTT CATTTTTC-3' (SEQ ID NO: 35) for GIRK1 and 5'-GCGGGATCCGCTATGGCTGGTGATTCTAGG AATG-3' (SEQ ID NO: 36) and
5'-CCGGAATTCCCCTCACACCGAGCCCCTGG-3' (SEQ ID NO: 37) for GIRK4. In each primer pair, the upstream primer contained a BamHI site and the downstream primer contained an EcoRI site to facilitate cloning of the PCR product into pcDNA1-Amp (Invitrogen). mRNAs were transcribed using the T7 polymerase ("Message Machine", Ambion). Each oocyte received 2 ng each of GIRK1 and GIRK4 mRNA in combination with 25 ng of GalR2 mRNA. After injection of mRNAs, oocytes were incubated at 17° for 3–8 days.

Dual electrode voltage clamp ("GeneClamp", Axon Instruments Inc., Foster City, Calif.) was performed using 3 M KCl-filled glass microelectrodes having resistances of 1–3 Mohms. Unless otherwise specified, oocytes were voltage clamped at a holding potential of −80 mV. During recordings, oocytes were bathed in continuously flowing (1–3 mL/min) medium containing 96 mM NaCl, 2 mM KCl, 2 mM $CaCl_2$, 2 mM $MgCl_2$, and 5 mM HEPES, pH 7.5 (ND96), or, in the case of oocytes expressing GIRKs 1 and 4, elevated $K^+$ containing 48 mM KCl, 49 mM NaCl, 2 mM $CaCl_2$, 2 mM $MgCl_2$, and 5 mM HEPES, pH 7.5 (1/2 hK). Drugs were applied either by local perfusion from a 10 μL glass capillary tube fixed at a distance of 0.5 mm from the oocyte, or for calculation of steady-state $EC_{50}$s, by switching from a series of gravity fed perfusion lines. Experiments were carried out at room temperature. All values are expressed as mean±standard error of the mean.

Galanin Receptor Autoradiography

Male Sprague-Dawley rats (Charles River, Wilmington, Mass.) were euthanized using $CO_2$, decapitated, and their brains immediately removed and frozen on dry ice. Tissue sections were cut at 20 μm using a cryostat and thaw mounted onto gelatin coated slides. Tissues were preincubated in two 10 minute changes of 50 mM Tris-HCl buffer pH 7.4, containing 5 mM $MgSO_4$ and 2 mM EGTA (Sigma). The radioligand binding was carried out in the same buffer, which also contained 0.1% bovine serum albumin, 0.02% aprotinin, 0.031% leupeptin, 0.1% phosphoramidate (Boehringer Mannheim), and 0.1 nM [$^{125}$I]porcine galanin (specific activity 2200 Ci/mmol, NEN) for 1 hour at 22° C. Nonspecific binding was determined in the presence of 5 μM porcine galanin (Bachem). As [D-Trp$^2$]galanin$_{(1-29)}$ was shown to be selective for the cloned GAlR2 receptor (infra), a 60 nM concentration of this peptide was used to displace [$^{125}$I]galanin binding from the rat brain tissue sections. The use of this concentration was based on the binding data, which showed the affinity of [D-Trp$^2$]galanin$_{(1-29)}$ to be 6 nM at the GALR2 receptor, and 3 μM at the GALR1 receptor. In general, a 10× concentration of the blocking ligand is sufficient to remove 100% of the targeted receptor, while leaving the GALR1 receptor unaffected. After incubation, tissues were dipped twice in ice-cold Tris-HCl buffer (4° C.), followed by a 5 minute wash in ice-cold Tris-HCl buffer (4° C.), then dipped twice in ice-cold deionized water to remove the salts. Sections were placed in X-ray cassettes and apposed to Dupont Cronex MRF 34 Film for 5 days. Films were developed using a Kodak M35A Processor.

Tissue Preparation for Neuroanatomical Studies

Male Sprague-Dawley rats (Charles River) are decapitated and the brains rapidly removed and frozen in isopentane. Coronal sections are cut at 11 μm on a cryostat and thaw-mounted onto poly-L-lysine coated slides and stored at −80° C. until use. Prior to hybridization, tissues are fixed in 4% paraformaldehyde, treated with 5 mM dithiothreitol, acetylated in 0.1 M triethanolamine containing 0.25% acetic anhydride, delipidated with chloroform, and dehydrated in graded ethanols.

Probes oligonucleotide probes employed to characterize the distribution of the rat GALR2 receptor mRNA may be synthesized, for example, on a Millipore Expedite 8909 Nucleic Acid Synthesis System. The probes are then lyophilized, reconstituted in sterile water, and purified on a 12% polyacrylamide denaturing gel. The purified probes are again reconstituted to a concentration of 100 ng/μL, and stored at −20° C. Probe sequences may include DNA or RNA which is complementary to the mRNA which encodes the GALR2 receptor.

Localization of GALR2 mRNA: In Situ Hybridization Animals

Timed-pregnant female Sprague-Dawley rats were puchased from Charles River. The day of birth for each litter was designated as postnatal day 0 (P0). Brains were removed from pups on P0, P3, PS, P8, P10, P15, P20, and P25. The brains from the mothers were also removed and used as the adult comparison. All brains were sectioned in the coronal plane at 11 μm and the sections thaw-mounted on to poly-1-lysine coated microscope slides. The sections were then used for in situ hybridization histochemistry as described below.

Tissue Preparation

Prior to hybridization, tissues were fixed in 4% paraformaldehyde, treated with 5 mM dithiothreitol, acetylated in 0.1 M triethanolamine containing 0.25% acetic anhydride, delipidated with chloroform, and dehydrated in graded ethanols. The sections were prehybridized for one hour at 40° C. in hybridization buffer, which consisted of 50% formamide, 4×sodium citrate buffer (1×SSC=0.15 M NaCl and 0.015 M sodium citrate), 1×Denhardt's solution (0.2% polyvinylpyrrolidine, 0.2% Ficoll, 0.2% bovine serum albumin), 50 mM dithiothreitol, 0.5 mg/ml salmon sperm DNA, 0.5 mg/ml yeast tRNA, and 10% dextran sulfate.

In Situ Hybridization

32mer oligonucleotide probes complementary to nucleotides 261–292 of the GALR2 mRNA were synthesized, purified, and 3'-end labeled with $^{35}$S-DATP (1200 Ci/mmol, New England Nuclear, Boston, Mass.) to a specific activity of $10^9$ dpm/μg using terminal deoxynucleotidyl transferase (Boehringer Mannheim; Indianapolis, Ind.). The radiolabeled probes were purified on Biospin 6 chromatography columns (Bio-Rad; Richmond, Calif.), and diluted in the hybridization buffer described above to a concentration of $1.5×10^4$ cpm/μl. One hundred μl of the radiolabeled probe was applied to each section, which was then covered with a Parafilm coverslip. Hybridization was carried out overnight in humid chambers at 40 to 55° C. The following day the sections were washed in two changes of 2×SSC for one hour at room temperature, in 2×SSC for 30 min at 50–60° C., and finally in 0.1×SSC for 30 min at room temperature. Tissues were dehydrated in graded ethanols and apposed to Kodak XAR-5 film for 2 weeks at −20° C., then dipped in Kodak NTB3 autoradiography emulsion diluted 1:1 with 0.2% glycerol water. After exposure at 4° C. for 4 weeks, the slides were developed in Kodak D-19 developer, fixed, and counterstained with hematoxylin and eosin.

Localization of GALR2 mRNA: Ribonuclease Protection Assay (RPA)

Development of Probes

A cDNA fragment encoding a 467 BP fragment of the rGAL R2 was subcloned into a pBluescript plasmid vector. This construct was linearized with Xba I or Sal I. T3 and T7 RNA polymerases were used to synthesize the sense and antisense strands of RNA respectively. Full-length RNA transcripts were obtained using a full-length cDNA construct in the same vector.

A probe coding for rat glyceraldehyde 3-phosphate dehydrogenase (GAPDH) gene, a constitutively expressed protein, was used concurrently. GAPDH is expressed at a relatively constant level in most tissue and its detection was used to compare expression levels of the rGalR2 gene in different tissues.

RNA Extraction

RNA was isolated from rat peripheral tissue as well as regions of the CNS using a LiCl precipitation protocol (Cathala et al., 1983). Tissue was homogenized in 5M guanidine isothiocyanate, 50 mM TRIS, 10 mM EDTA, using 7 ml of lysis buffer/gram tissue. 4M LiCl were added (7 ml/ml homogenate) and the mixture were stored at 4° C. for 24–48 hours. Homogenates were centrifuged and the pellets were resuspended in 3M LiCl, and centrifuged again. The pellets were resuspended in 0.1% sodium dodecyl sulfate (SDS), extracted in phenol:chloroform:isoamyl alcohol (24:24:1) and the RNA ethanol precipitated. Yield and relative purity were assessed by measuring absorbance $A_{260}/A_{280}$.

Synthesis of Probes rGALR2 and GAPDH cDNA sequences preceded by phage polymerase promoter sequences were used to synthesize radiolabeled riboprobes. Conditions for the synthesis of riboprobes were: 1–2 μl linearized template (1 μg/μl) 1 μl of ATP, GTP, UTP (10 mM each), 2 μl dithiothreitol (0.1 M), 20 units RNAsin RNAse inhibitor, 1–2 μl (15–20 units/μl) RNA polymerase, 4 μl transcription buffer (Promega Corp.), and 5 μl $\alpha^{32}$P-CTP (specific activity 800Ci/mmol). 0.1 mM CTP (0.02–1.0 μl) were added to the reactions, and the volume were adjusted to 20 μl with DEPC-treated water. Labeling reactions were incubated at 38° C. for 90 min, after which 2 units of RQ1 RNAse-free DNAse (Promega Corp.) were added to digest the template. The riboprobes were separated from unincorporated nucleotide by a spun G-50 column (Select D G-50(RF); 5 Prime-3 Prime, Inc.). TCA precipitation and liquid scintillation spectrometry were used to measure the amount of label incorporated into the probe. A fraction of all riboprobes synthesized were size-fractionated on 0.4 mm thick 5% acrylamide sequencing gels and autoradiographed to confirm that the probes synthesized were full-length and not degraded.

Solution Hybridization/Ribonuclease Protection Assay

For solution hybridization 2–15 μg of total RNA isolated from tissues were used. Sense RNA synthesized using the full-length coding sequence of the rGalR2 was used to characterize specific hybridization. Negative controls consisted of 30 μg transfer RNA (tRNA) or no tissue blanks. All samples were placed in 1.5-ml microfuge tubes and vacuum dried. Hybridization buffer (40 μl of 400 mM NaCl, 20 mM Tris, pH 6.4, 2 mM EDTA, in 80% formamide) containing 0.25–1.0×10$^6$ counts of each probe were added to each tube. Samples were heated at 90° C. for 15 min, after which the temperature were lowered to 45° C. for hybridization.

After hybridization for 14–18 hr, the RNA/probe mixtures were digested with RNAse A (Sigma) and RNAse T1 (Bethesda Research Labs). A mixture of 2.0 μg RNAse A and 1000 units of RNAse T1 in a buffer containing 330 mM NaCl, 10 mM Tris (pH 8.0) and 5 mM EDTA (400 μl) was added to each sample and incubated for 90 min at room temperature. After digestion with RNAses, 20 μl of 10% SDS and 50 μg proteinase K were added to each tube and incubated at 37° C. for 15 min. Samples were then extracted with phenol/chloroform:isoamyl alcohol and precipitated in 2 volumes of ethanol for 1 hr at −70° C. tRNA was added to each tube (30 mg) as a carrier to facilitate precipitation. Following precipitation, samples were centrifuged, washed with cold 70% ethanol, and vacuum dried. Samples were dissolved in formamide loading buffer and size-fractionated on a urea/acrylamide sequencing gel (7.6 M urea, 6% acrylamide in Tris-borate-EDTA). Gels were dried and apposed to Kodak XAR-5 x-ray film.

In Vivo Methods

The effects of galanin, galanin derivatives, and related peptides and compounds were evaluated by intracerebroventricular (i.c.v.) injection of the peptide or compound followed by measurement of food intake in the animal. Measurement of food intake was performed for 3 hours after injection, but other protocols may also be used. Saline was injected as a control, but it is understood that other vehicles may be required as controls for some peptides and compounds. In order to determine whether a compound is a GALR2 antagonist, food intake in rats may be stimulated by administration of (for example) the GALR2-selective peptide agonist [D-Trp$_2$]-galanin$_{(1-29)}$ through an intracerebroventricular (i.c.v.) cannula. A preferred anatomic location for injection is the hypothalamus, in particular, the paraventricular nucleus. Methods of cannulation and food intake measurements are well-known in the art, as are i.c.v. modes of administration (Kyrkouli et al., 1990, Ogren et al., 1992). To determine whether a compound reduces [D-Trp$_2$]-galanin$_{(1-29)}$ stimulated food intake, the compound may be administered either simultaneously with the peptide, or separately, either through cannula, or by subcutaneous, intramuscular, or intraperitoneal injection, or more preferably, orally.

Materials

Cell culture media and supplements are from Specialty Media (Lavallette, N.J.). Cell culture plates (150 mm and 96-well microtiter) are from Corning (Corning, N.Y.). Sf9, Sf21, and High Five insect cells, as well as the baculovirus transfer plasmid, pBlueBacIII™, are purchased from Invitrogen (San Diego, Calif.). TMN-FH insect medium complemented with 10% fetal calf serum, and the baculovirus DNA, BaculoGold™, is obtained from Pharmingen (San Diego, Calif.). Ex-Cell 400™ medium with L-Glutamine is purchased from JRH Scientific. Polypropylene 96-well microtiter plates are from Co-star (Cambridge, Mass.). All radioligands are from New England Nuclear (Boston, Mass.)

Galanin and related peptide analogs were either from Bachem Calif. (Torrance, Calif.), Peninsula (Belmont, Calif.); or were synthesized by custom order from Chiron Mimotopes Peptide Systems (San Diego, Calif.).

Bio-Rad Reagent was from Bio-Rad (Hercules, Calif.). Bovine serum albumin (ultra-fat free, A-7511) was from Sigma (St. Louis. Mo.). All other materials were reagent grade.

Experimental Results

Isolation of a GALR2 cDNA from Rat Hypothalamus

In order to clone additional members of the galanin receptor family, an expression cloning strategy based on the potential presence of multiple galanin receptors in hypothalamus was designed. Although recent evidence indicated that GALR1 receptor mRNA was present in rat hypothalamus (Gustafson et al., 1996; Parker et al., 1995), not all aspects of the cloned GALR1 pharmacological profile match that observed for galanin-mediated feeding (Crawley et al., 1993). These results suggested that the regulation of galanin-induced feeding may not be explained by the presence of only GALR1 in the rat hypothalamus.

A randomly-primed cDNA expression library was constructed from rat hypothalamus and screened by radioligand binding/photoemulsion detection using [$^{125}$I]-porcine galanin. The library consisted of 584 pools containing about 5,000 primary clones/pool for a total of about 3 million clones with an average insert size of 2.2 kb. Pools positive for rat GALR1 (about 110) were eliminated from the screen. Remaining pools were screened for radioligand binding using 1 nM [$^{125}$I]-porcine galanin; slides were inspected for positive cells by direct microscopic examination. One positive pool (J126) was subdivided into 96 pools of about 90 clones each and rescreened for galanin binding. Preliminary pharmacology carried out on the positive subpool J126-10 indicated that the [$^{125}$I]-porcine galanin binding was not sensitive to inhibition by galanin 3–29. 400 individual colonies of a positive pool (J26-10) were then screened to find two single purified cDNA clones. J126-10-334 was chosen for further analysis and designated K985. PCR analysis using three independent GALR1 primer sets (see Methods; data not shown) confirmed that the newly isolated cDNA was distinct from GALR1 and thus encoded a new galanin receptor subtype, termed GALR2.

The isolated clone K985 carries a 3.8 kb insert. Sequence analysis of this cDNA revealed a complete coding region for a novel receptor protein which we term GALR2 (see FIGS. 1 and 2). Searches of GenEMBL databases indicated that the sequence was novel, and that the most similar sequence was that of the galanin receptor GALR1, followed by other G protein-coupled receptors (GPCR). The nucleotide and deduced amino acid sequences are shown in FIGS. 1 and 2, respectively. The nucleotide sequence of the coding region is ~56% identical to rat GALR1 and ~54% identical to human GALR1 and encodes a 372 amino acid protein with 38% and 40% amino acid identity to rat and human GALR1, respectively. Hydropathy plots of the predicted amino acid sequence reveal seven hydrophobic regions that may represent transmembrane domains (TMs, data not shown), typical of the G protein-coupled receptor superfamily. In the putative TM domains, GALR2 exhibits 48–49% amino acid identity with rat and human GALR1. Like most GPCRs, the GALR2 receptor contains consensus sequences for N-linked glycosylation in the N-terminus (positions 2 and 11) as well as the predicted extracellular loop between TMs IV and V. The GALR2 receptor contains two highly conserved cysteine residues in the first two extracellular loops that are believed to form a disulfide bond stabilizing the functional protein structure (Probst et al., 1992). GALR2 shows five potential phosphorylation sites for protein kinase C in positions 138, 210, 227, 319, and 364, and two cAMP- and cGMP-dependent protein kinase phosphorylation sites in positions 232 and 316. It should be noted that six out of the seven potential phosphorylation sites are located in pre- dicted intracellular domains, and therefore could play a role in regulating functional characteristics of the GALR2 receptor (Probst et al., 1992).

Figure 3B:
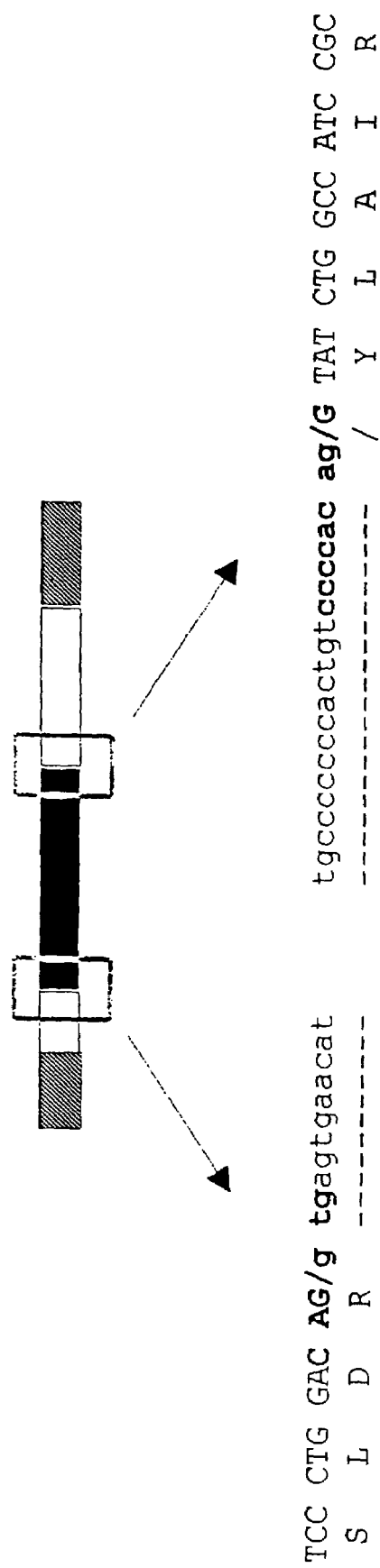

Within the GALR2 cDNA K985 (J126-10-334) isolated from the rat hypothalamus library, the coding region of GALR2 is interrupted by an intron of ~1 kb (FIGS. 3A, 3B, and 3C). A cDNA containing an intron may be produced by the action of reverse transcriptase on an incompletely spliced form of messenger RNA. The heterologous expression of the complete protein product is not necessarily impeded by the presence of the intron in the coding region, because the intron can typically be spliced out prior to translation by the host cell machinery. In the case of the GALR2 cDNA, the location of the intron combined with clear consensus sequences for 5' and 3' splice junctions (FIGS. 3A and 3B) confirm that the intervening sequence represents an intron. As shown in FIG. 3C, splicing of the intron at the indicated sites recreates an open reading frame within a highly conserved region of the GPCR family, at the end of TMIII (LDR/Y). It is of interest to note that several GPCRs have previously been reported to contain introns at this location, including the human dopamine D3, D4, and D5 receptors, the rat substance P receptor, and the human substance K receptor (Probst et al., 1992). In particular, the rat 5-HT$_7$ receptor (Shen et al., 1993) contains an intron in exactly the same location as is now reported for GALR2, within the AG/G codon for the highly conserved amino acid arginine at the end of TMIII (FIG. 3C).

To explore the possibility that incompletely or alternately spliced forms GALR2 mRNAs are present in the rat brain, RT-PCR using GALR2 PCR primers that are located in the coding region but that span the location of the intron was carried out. The sequences of the PCR primers are:

KS-1515 (Forward primer): 5'-CAAGGCTGT-TCATTTCCTCATCTTTC (loop between TMs II and III) (SEQ. ID NO: 10).

KS-1499 (Reverse primer): 5'-TTGGAGACCAGAGCG-TAAACGATGG (end of TMVII) (SEQ. ID NO: 11).

The PCR products were separated by gel electrophoresis, blotted, and hybridized with a radiolabeled oligonucleotide probe representing the predicted loop between TMs V and VI. The sequence of the oligonucleotide is:

KS-1540: 5'-AGTCGACCCGGTGACTGCAGGCT-CAGGTTCCCAGCGCGCCAAACG (SEQ ID NO: 12).

Figures 4, 4A, 5:
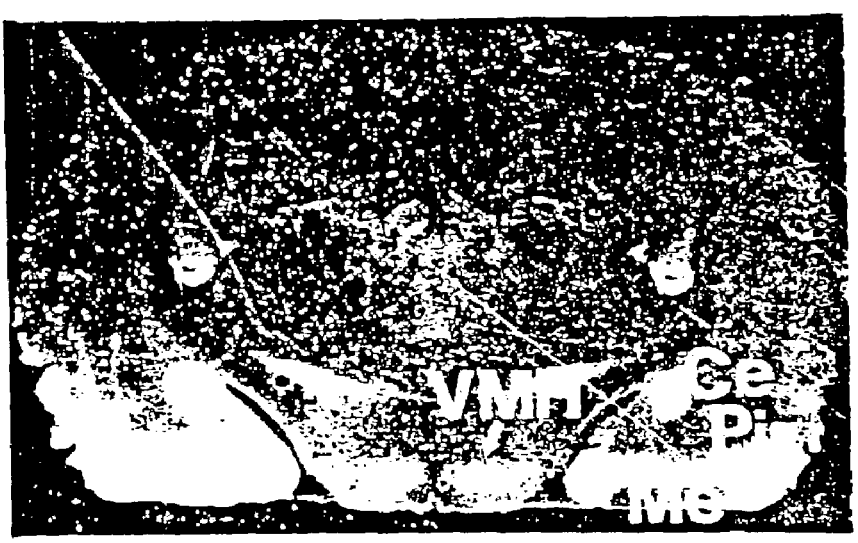
Figures 4, 4A, 5, 6:
Figures 1, 4B:
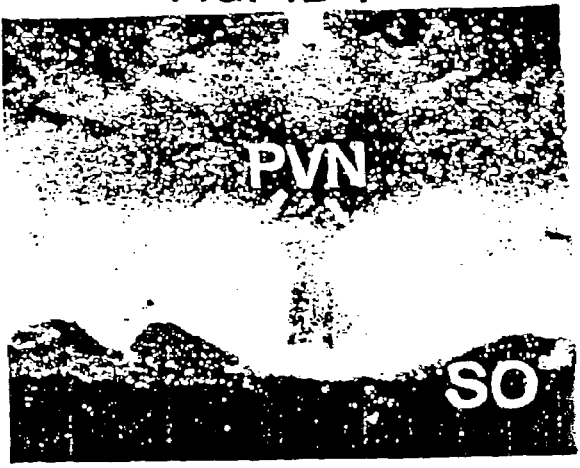
Figures 2, 4B:
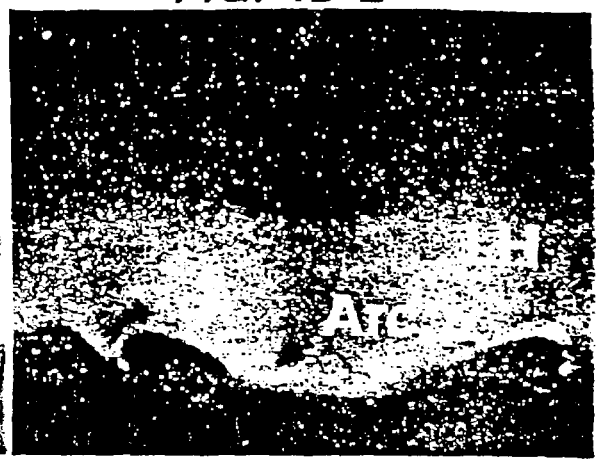
Figures 3, 4B:
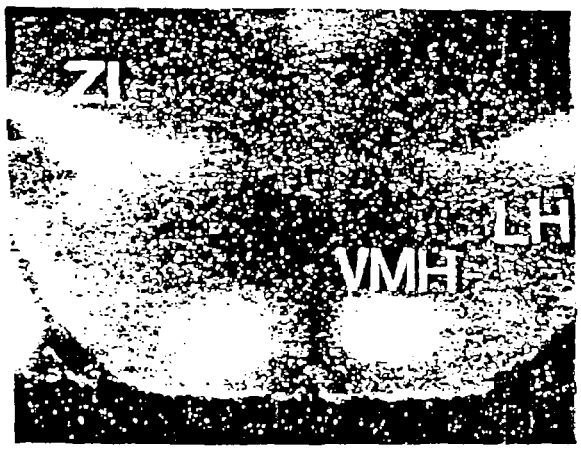
Figures 4, 4B:
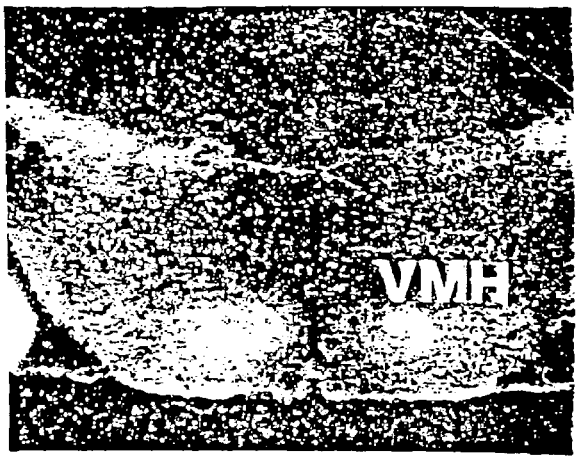
Figures 4, 4B, 5:
Figures 4, 4B, 5, 6:
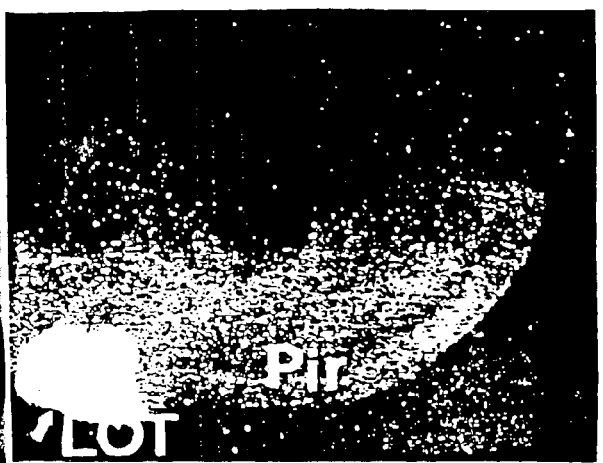
Figures 4, 4B, 5, 6, 7:
Figures 4, 4B, 5, 6, 7, 8:
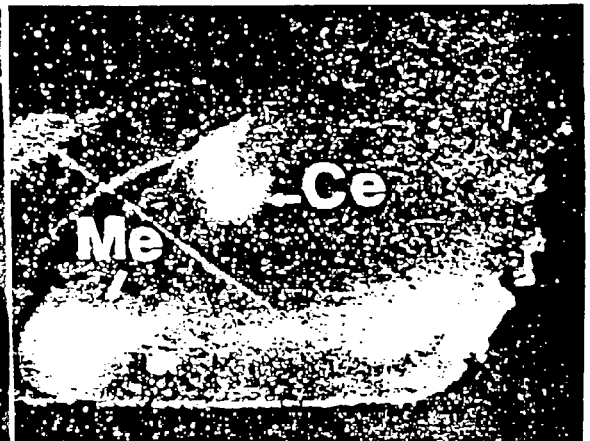
Figures 1, 4C:
Figures 2, 4C:
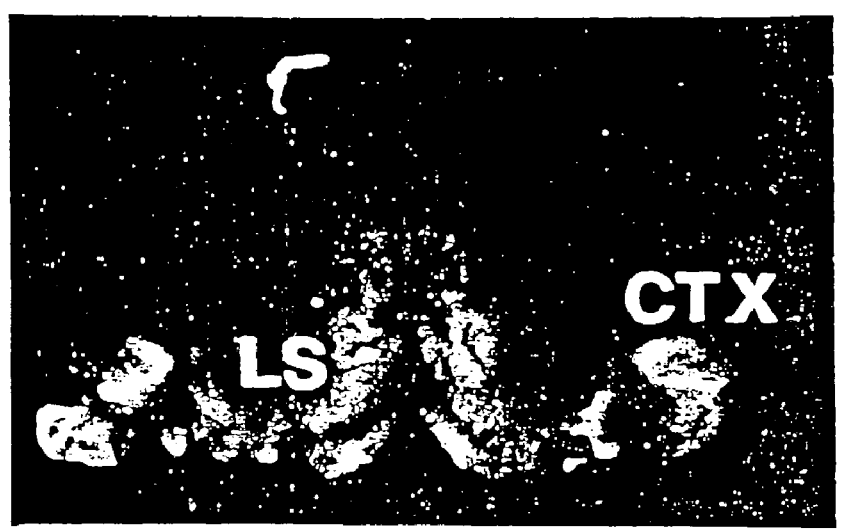
Figures 3, 4C:
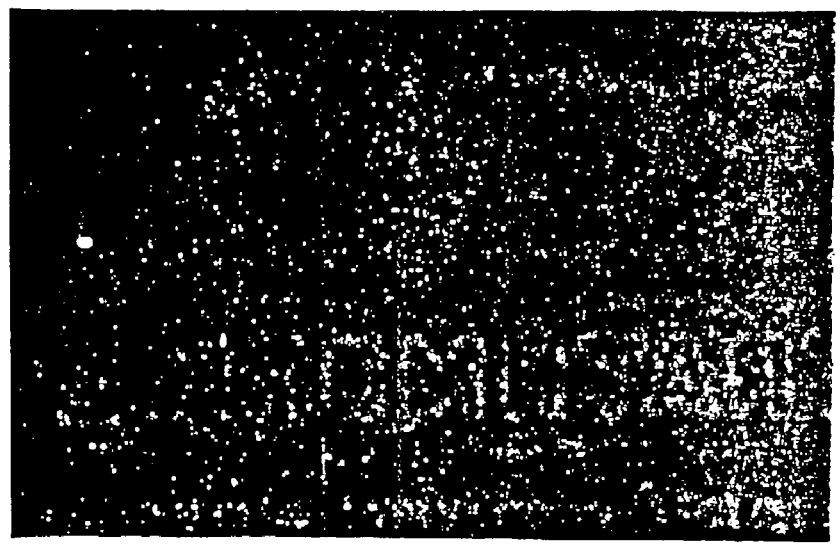
Figures 4, 4C:
Figures 4, 4C, 5:
Figures 4, 4C, 5, 6:
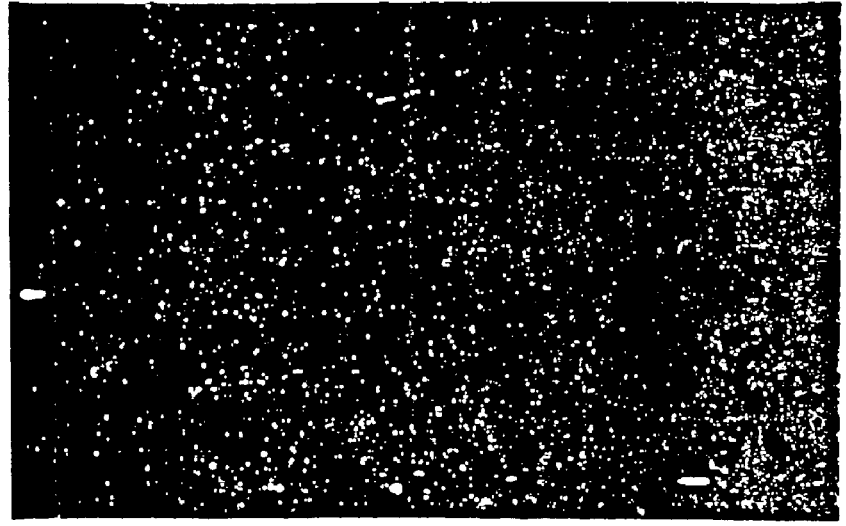
Figure 5:
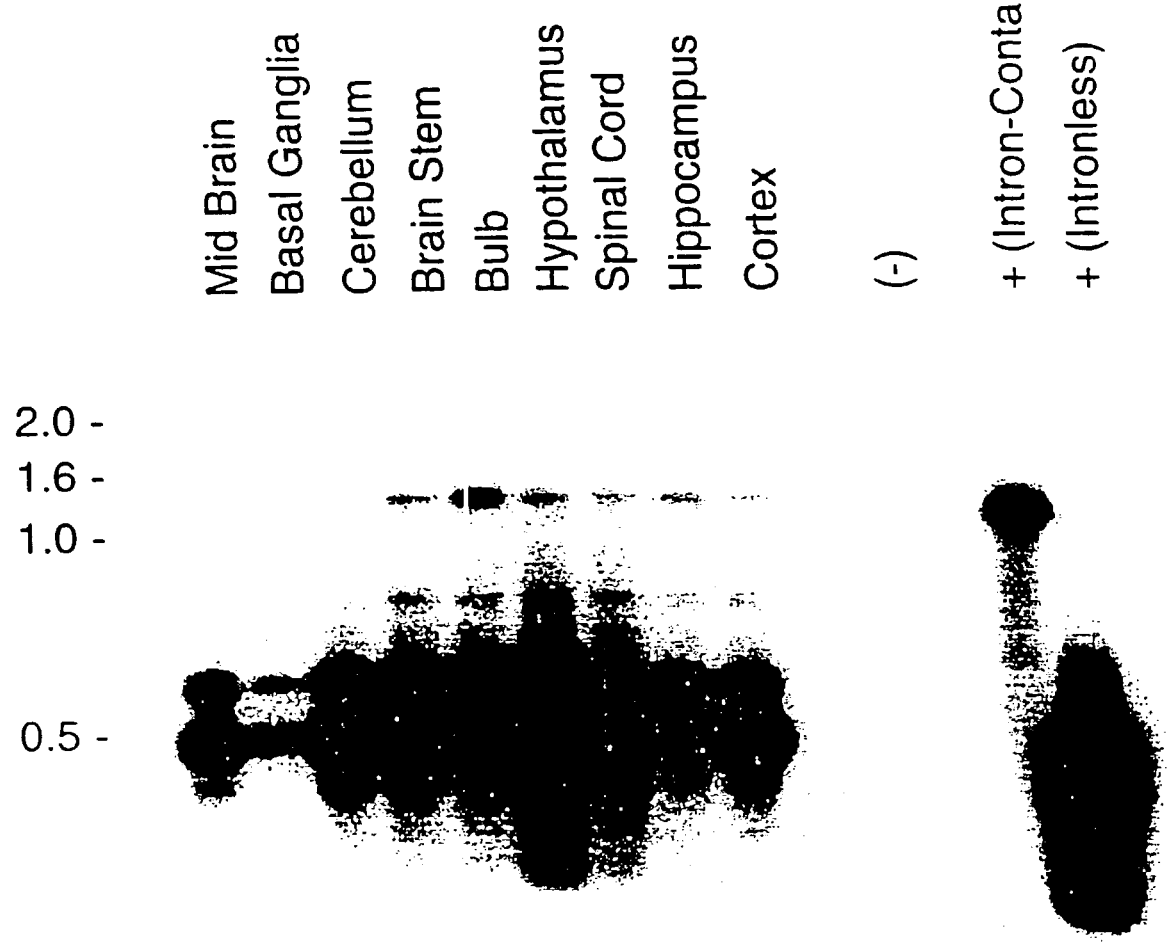

RT-PCR analysis of GALR2 mRNA from various rat brain regions as described above indicates the existence of PCR products that may represent both the intronless (spliced) and intron-containing (incompletely spliced) forms of GALR2 (FIG. 5). In addition, PCR products intermediate in size between intronless and intron-containing products that hybridize at high stringency with the GALR2 oligonucleotide probe KS-1540 are present and may represent additional variations in the GALR2 mRNA. One mechanism that could generate such variations is alternative splicing. These results suggest that intronless transcripts exist in native tissue. A full-length intronless cDNA encoding the rat GALR2 receptor has been amplified and subcloned from rat heart RNA, which when transiently or stably transfected into cells binds galanin with high affinity.

Northern Blot Analysis of GALR2 mRNA

To define the size and distribution of the mRNA encoding GALR2 Northern blot analysis of poly A$^+$ RNA from various rat tissues and brain regions was carried out. A ~1.2 kb fragment of rat GALR2 containing the entire coding region but not containing the intron (FIG. 1) was radiolabeled by random priming and used as a hybridization probe.

Figure 6A:
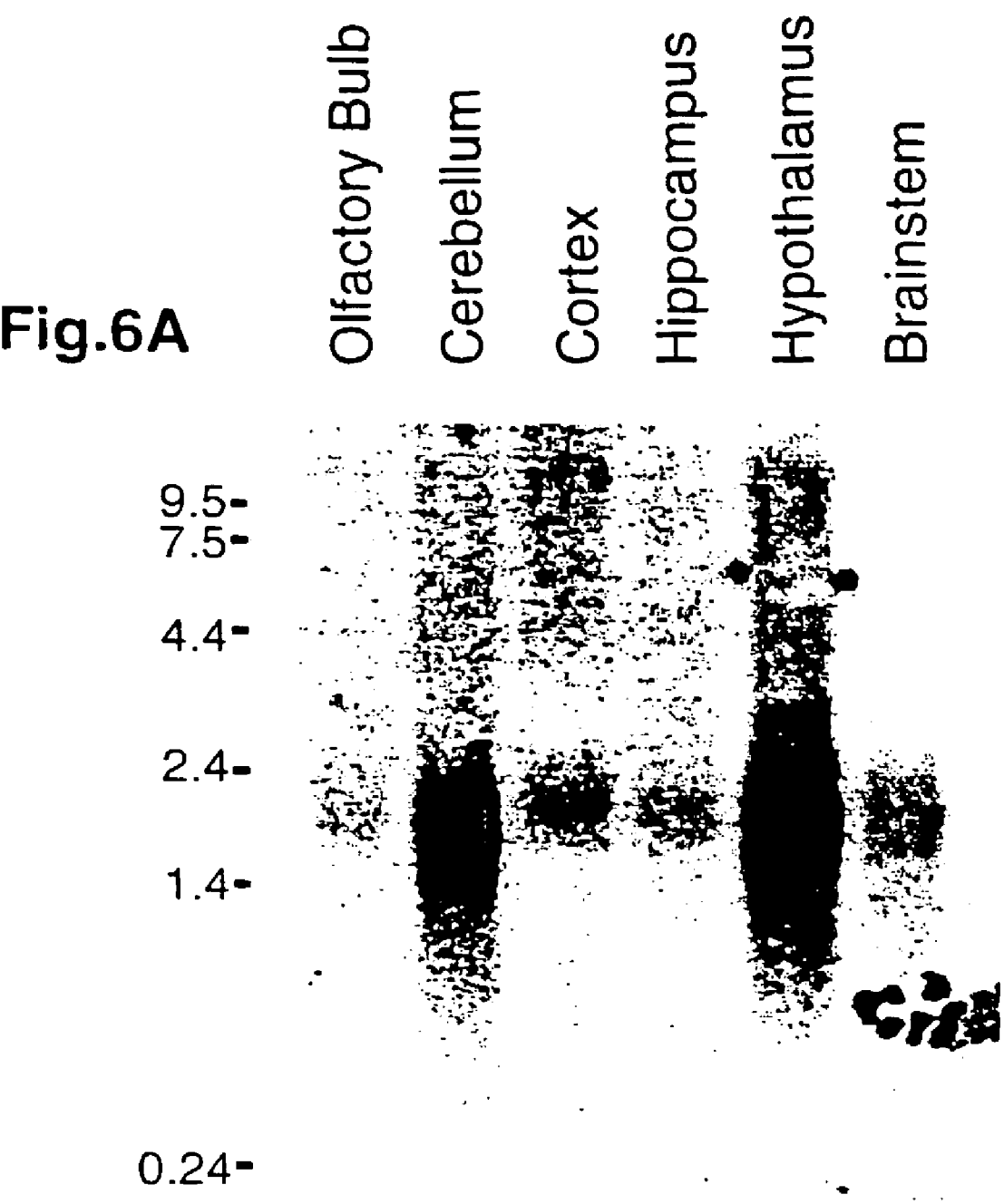
FIGS. 6A–6B. Northern blot analysis of GALR2 receptor mRNA from various rat brain regions. 6A. A Northern blot containing poly A+ RNA (~5 μg) from six different rat brain regions was hybridized at high stringency with a randomly primed radiolabeled fragment representing the entire rat GALR2 coding region (not including the intron). The autoradiogram represents a four day exposure and reveals a ~1.8–2.0 kb transcript. 6B. The blot was reprobed with 1B15 (~1 kb) to confirm that similar amounts of RNA were present in each lane.
Figure 6B:
Figure 7A:
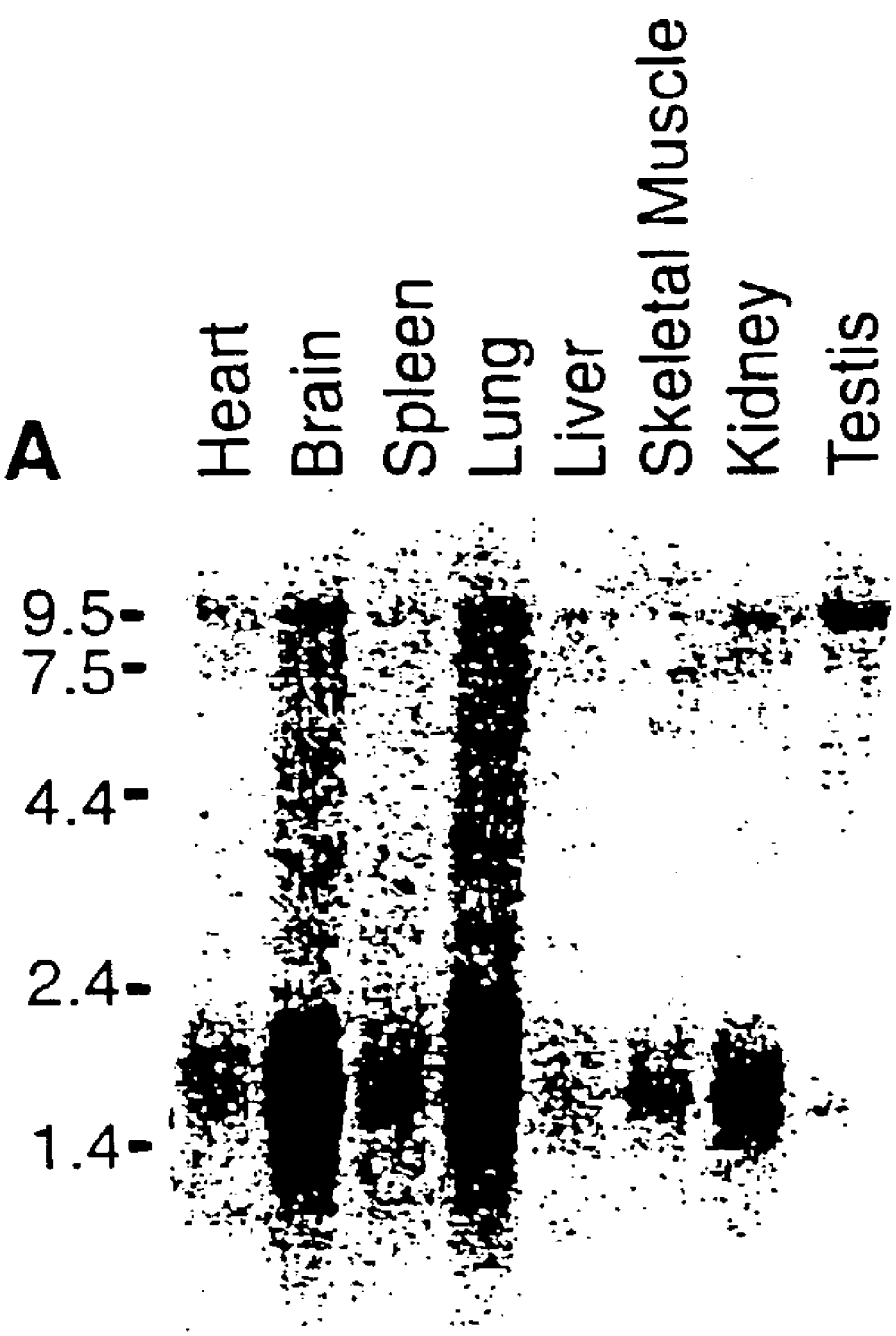
FIGS. 7A–7B. Northern blot analysis of GALR2 receptor mRNA from various rat tissues. 7A. A Northern blot containing poly A+ RNA (~2 μg) from eight different rat tissues was hybridized at high stringency with a randomly primed radiolabeled fragment representing the entire rat GALR2 coding region (not including the intron). The autoradiogram represents a four day exposure and reveals a single ~1.8–2.0 kb transcript. 7B. The Northern blot was reprobed for 1B15 (~1 kb) to confirm that similar amounts of RNA were present in each lane. A second Northern blot (not shown) was also hybridized under the same conditions and showed similar results (Table 3).
Figure 7B:
Figure 8A:
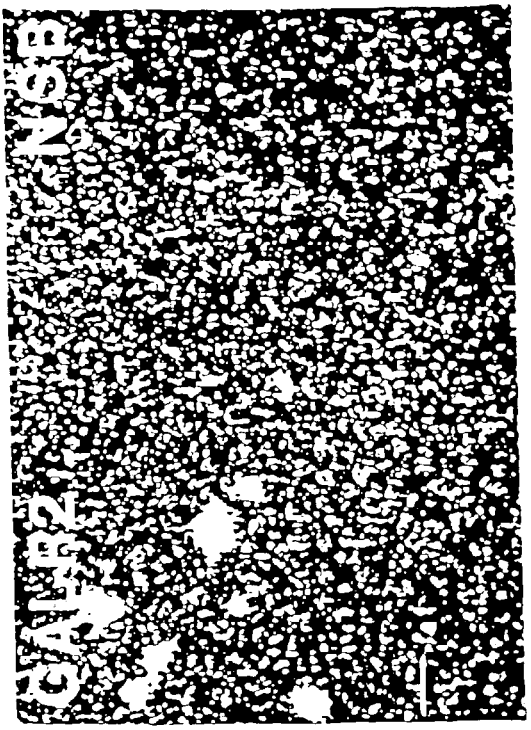
FIGS. 8A–8D. Rat GALR2 receptor autoradiography in COS-7 cells transfected with GALR1 and GALR2 cDNAs. $^{125}$I-[D-Trp$^2$]Galanin$_{(1-29)}$ was tested as a selective radioligand for GALR2. Panels represent dark-field photomicrographs (200×) of photoemulsion-dipped slides. 8A: Binding of 3 nM $^{125}$I-[D-Trp$^2$]Galanin$_{(1-29)}$ to COS-7 cells transiently transfected with GALR2. Note positive binding to cells.
Figure 8B:
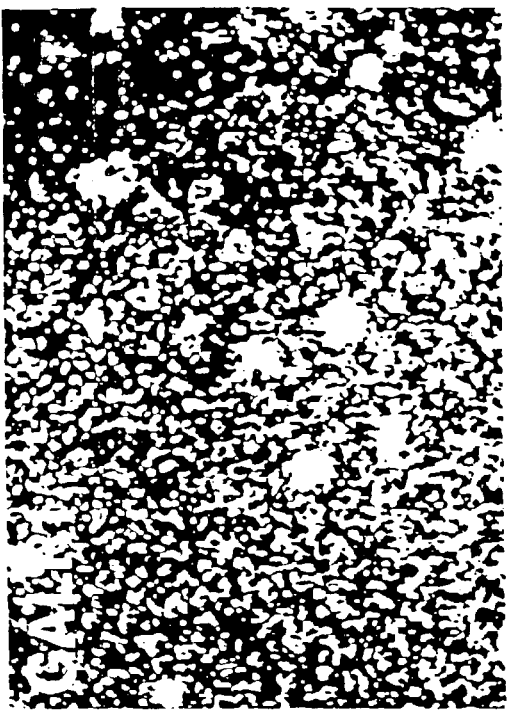
Figure 8C:
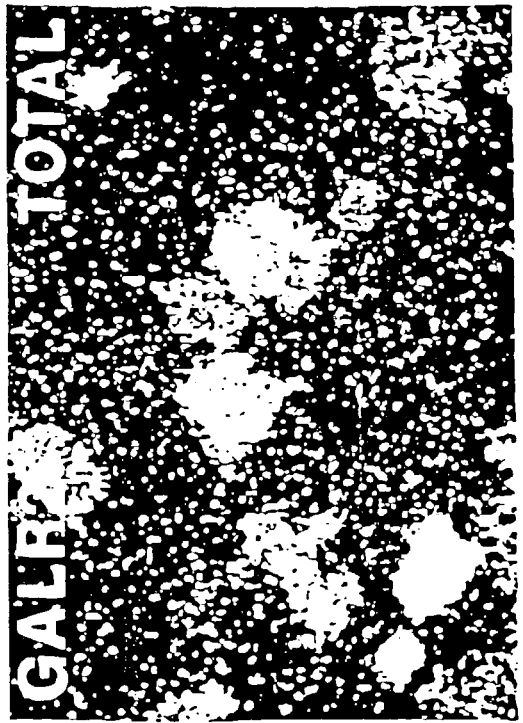
Figure 8D:
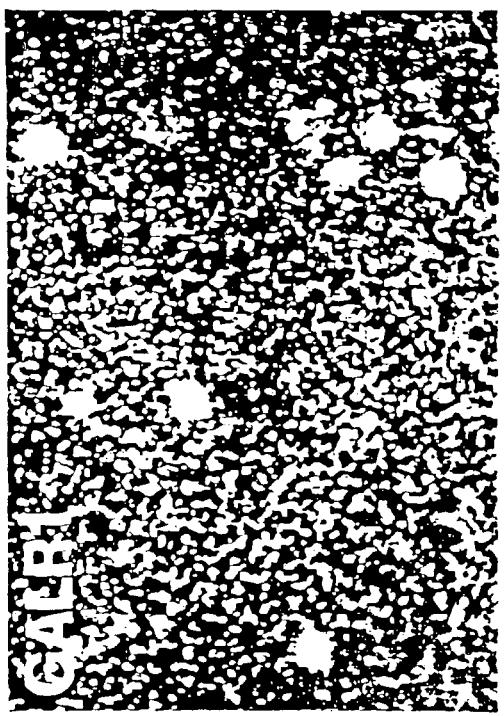

Northern blots containing rat poly A+ RNA were hybridized at high stringency and apposed to film. A single transcript of ~1.8–2.0 kb is detected after a 4 day exposure of the autoradiogram at −80° C. using Kodak Biomax MS film with one Biomax MS intensifying screen. Within the brain, the highest levels of GALR2 mRNA appear in hypothalamus (FIG. 6A). Among various rat tissues, the GALR2 transcript is widely but unevenly distributed: GALR2 mRNA is observed in brain, lung, heart, spleen, and kidney, with lighter bands in skeletal muscle, liver, and testis (FIG. 7A). Both Northern blots were reprobed with 1B15 to confirm that similar amounts of mRNA were present in each lane (FIGS. 6B and 7B).

Pharmacological Characterization of GALR2

The pharmacology of GALR2 was studied in COS-7 cells transiently transfected with the GALR2 cDNA, K985. Membrane preparations of Cos-7 cells transfected with K985 displayed specific binding to [$^{125}$I]porcine galanin. Scatchard analysis of equilibrium saturation binding data yielded a $K_d$=150 pM with a $B_{max}$=250 fmol/mg protein. The pharmacological properties of the protein encoded by the GALR2 cDNA were probed by measuring the binding affinities of a series of galanin anologs, and compared to those of the rat GALR1 receptor expressed in the same host cell line. As shown in Table 1, both GALR1 and GALR2 receptors showed a high affinity for galanin$_{(1-29)}$, the physiological ligand of these receptors. Both receptors also displayed high affinity for the truncated analogs galanin$_{(1-16)}$ and galanin$_{(1-15)}$. Furthermore, the binding of [$^{125}$I]porcine galanin to either GALR1 or GALR2 at concentrations up to 100 μM was not displaced by porcine galanin$_{(3-29)}$. However, the GALR2 receptor has 540- and 4200-fold higher affinity for [D-Trp$^2$]porcine galanin$_{(1-29)}$, and [D-Trp$^2$]galanin$_{(1-16)}$, respectively, than the GALR1 subtype. Also, [Ala$^5$]galanin$_{(1-16)}$, and [Phe$^2$]galanin$_{(1-15)}$ were moderately selective, with 15- and 17-fold greater affinities for the GALR2 receptor than for the GALR1 receptor subtype, respectively. [Ala$^9$]galanin$_{(1-16)}$ was the only analog that was found to have the opposite selectivity, with 70-fold higher affinity for the GALR1 receptor than for the GALR2 receptor. Interestingly, these two receptor subtypes showed no significant differences in their binding affinities for the chimeric galanin antagonists, galantide, C7, M32, M35, and M40.

In LM(tk-) cells stably expressing the rat GALR2 receptor cDNA, porcine galanin$_{(1-29)}$ was found to inhibit the formation of cyclic AMP induced by 10 μM forskolin. The effects of galanin were dose dependent with an $EC_{50}$=0.26±0.13 nM (n=3) (FIG. 9A). In the same cell line porcine galanin$_{(1-29)}$ stimulated the formation of [$^3$H]inositol phosphates, with an $EC_{50}$=112 nM (FIG. 9B). The phosphoinositide response mediated by the rat. GALR2 receptor suggests that this receptor can also couple to the intracellular calcium mobilization and diacylglycerol pathway. However, the 400-fold lower $EC_{50}$ of porcine galanin$_{(1-29)}$ suggests that the GALR2 receptor couples with low efficiency to this signaling pathway. In support of this notion stands the observation that porcine galanin$_{(1-29)}$ had no effect on intracellular calcium levels in COS-7 cells transfected with the cDNA encoding the rat GALR2 receptor. Thus, the data presented herein suggest that the GALR2 receptor couples preferentially to $G_{ialpha}$, since the stimulation of phosphoinositide metabolism and intracllular calcium mobilization are a hallmark or receptors to the $G_{q\alpha}$ family of G-proteins. Furthermore, the data presented herein also indicate that the inhibition of cAMP formation, as well as the stimulation of phosphoinositide metabolism, can be used as functional assays to measure receptor activity in heterologous cell systems expressing the rat GALR2 receptor. However, separate experiments using mouse fibroblast 293 cell lines stably expressing rat GALR2 receptors did not provide evidence for galanin-dependent inhibition of forskolin-stimulated cAMP.

In subsequent experiments, the inhibitory effect of rat GALR2 receptor stimulation on forskolin-stimulated cAMP accumulation in LM(tk-) cells could not be reproduced. However, the same LM(tk-) cells yielded a reproducible PI hydrolysis response (Table 4), and in independent binding assays a $B_{max}$ of 4000 fmol/mg protein and a $K_d$ of 1.1 nM when incubated with porcine $^{125}$I-galanin. It is concluded that in the cell lines studied thus far, the rat GalR2 is coupled primarily to the activation of phospholipase C and subsequent inositol phosphate metabolism, presumably through Gq or a related G protein. The PI response was evident as well in LM(tk-) cells stably transfected with the rat GALR2 receptor cDNA lacking an intron in the coding region (L-rGALR2I-4, see Table 4); membranes from these cells were shown in an independent experiment to bind porcine $^{125}$I-galanin with a $B_{max}$ of 4800 fmol/mg membrane protein and a $K_d$ of 0.2 nM.

The CHO cell line stably transfected with the rat GALR2 receptor (C-rGALR2-79) provided additional detail about the binding and signaling properties of the receptor. Membranes from stably transfected CHO cells were bound saturably by porcine $^{125}$I-galanin with a $B_{max}$ of 520 fmol/mg membrane protein and a $K_d$ of 0.53 nM. Peptides displaced the porcine $^{125}$I-galanin (Table 5) with binding affinities similar to those generated from transiently transfected COS-7 cells (Table 1). Receptor stimulation resulted in phosphatidyl inositol hydrolysis (which was resistant to pre-treatment with pertussis toxin, see FIG. 16D) but had no effect on cAMP accumulation, again supporting the proposal that the rat GALR2 receptor is coupled primarily to phospholipase C activation through Gq or a related G protein. Further support for the coupling of rat GALR2 to Gq is the observation that intracellular free [Ca$^{+2}$] was substantially increased by 1 μM rat galanin in C-rGALR2–79 (Δ[Ca$^{+2}$]=310±70 nM, n=9) but not in untransfected cells.

It was further demonstrated that rat GALR2 receptor activation could be monitored by arachidonic acid release (Table 5). Of interest, it was observed that the $EC_{50}$ values from the PI hydrolysis assays were larger than the $K_i$ values from binding assays whereas the $EC_{50}$ values from the arachidonic acid assays were comparable to the binding data. One possibility suggested by these data is that the diacylglycerol and calcium release associated with or induced by inositol phosphate metabolism leads to activation of protein kinase C, MAP kinase, phospholipase A2 and subsequently to the hydrolysis of arachidonic acid from membrane phospholipids. The lower $EC_{50}$ values in the arachidonic acid assays may reflect an amplification process in the second messenger pathway, such that a maximal arachidonic acid response occurs at submaximal inositol phosphate and diacylglycerol or calcium concentrations.

The stably transfected CHO cells were used to further explore the binding and signaling properties of the rat GalR2 receptors (Table 6). The peptide binding profile was similar to that generated previously with transiently transfected COS-7 cells. Porcine, rat and human galanin bound with high affinity as did C-terminally truncated peptides as short as galanin 1–12. Chimeric or putative "antagonist" peptides including C7, galantide, M32, M35 and M40 displayed relatively high binding affinity except for C7 (Ki=47 nM). Galanin analogs containing D-Trp$^2$ (D-Trp$^2$-galanin 1–29 and D-Trp$^2$-galanin 1–16) retained measurable binding affinity (K$_i$=41 and 110 nM, respectively). The N-terminally truncated peptide galanin 3–29 was inactive.

Selected peptides were subsequently tested in the arachidonic acid release assays. Peptides with measurable EC$_{50}$ values mimicked the maximal effect of rat galanin (1 µM) on arachidonic acid release and were classified as full agonists, including C7, galantide, M32, M35 and M40. Relative to rat galanin (EC$_{50}$=0.67 nM, the endogenous peptides galanin (–7) to (+29) and galanin (–9) to (+29), as well as the modified di-iodo analog D-Trp2-(3-iodo-L-Tyr9)-(-iodo-L-Tyr26)-galanin, were potent agonists in the GalR2 functional assay (EC$_{50}$ values between 2 and 4 nM). The binding and functional profiles were in general agreement. Notable exceptions include D-Trp$^2$-galanin 1–29, D-Trp$^2$-galanin 1–16, and C7, all of which generated larger K$_i$ values vs. EC$_{50}$ values; one possibility is that these peptides were less stable in the binding assay vs. the functional assay. It is, therefore, concluded that the arachidonic acid release assay is useful for assessing peptide potency and intrinsic activity for the rat GalR2 receptor when stably expressed in CHO cells.

Peptides were further evaluated for their ability to selectively activate the rat GALR1 receptor (monitored in stably transfected LM(tk–) cells using the forskolin-stimulated cAMP accumulation assay) vs. the rat GALR2 (monitored in stably transfected CHO cells using the arachidonic acid release assay). Data are reported in Table 7. Relative to galanin itself, D-Trp2-galanin analogs were selective for GALR2 vs. GALR1. For example, D-Trp2-(3-iodo-L-Tyr9)-(-iodo-L-Tyr26)-galanin was 1.5-fold less potent than porcine galanin in the rat GalR2 arachidonic acid assay but 15,000-fold less potent than porcine galanin in the rat GalR1 cAMP assay. D-Trp$^2$-galanin was 8.5-fold less potent than galanin in the rat GALR2 functional assay but>15000-fold less potent than galanin in the rat GALR1 functional assay. Similarly, D-Trp$^2$-galanin 1–16 was 38-fold less potent than galanin in the rat GALR2 functional assay but>170,000-fold less potent than galanin in the rat GALR1 functional assay. It is concluded that D-Trp$^2$-galanin and analogous peptides may serve as useful tools with which to explore the function of GALR2 vs. GALR1 receptors in native tissues and physiological systems. A similar proposal is made for the N-terminally extended peptides. In this case porcine galanin (–7) to (+29) and porcine galanin (–9) to (+29) were 3-fold and 2-fold less potent than porcine galanin in the rat GalR2 functional assay respectively, but 350-fold and 400-fold less potent than porcine galanin in the rat GalR1 functional assay. The N-terminal peptides can be purified from native tissues and may mediate GALR2-dependent processes in vivo.

The signal transduction pathway outlined for rat GalR2 allows for the development of functional assays other than inositol phosphate, calcium, and arachidonic acid determination. One such assay relies on the fact that binding of GTP to a G-protein precedes agonist-dependent activation of phospholipase C. We examined whether galanin-dependent activation of GALR2 could be monitored by the binding of GTPγ$^{35}$S to membranes from stably transfected cells. We observed that porcine galanin (1 µM) increased the binding of GTPγ$^{35}$S from 8,014±113 cpm (n=3) to 10,292±104 cpm (n=3) in membranes from C-rGALR2-79 cells. Similarly, porcine galanin (1 µM) increased the binding of GTPγ$^{35}$S from 27,545±504 cpm (n=3) to 29,011±526 cpm (n=3) in membranes from L-rGalR2I-4 cells (comprising the intronless plasmid).

Another functional assay relies on the fact that MAP kinase phosphorylation precedes the activation of phospholipase A2. We tested whether galanin-dependent activation of GALR2 could be monitored by changes in MAP kinase phosphorylation. Using an antibody specific for phosphorylated MAP kinase in a western blot protocol with a chemiluminescent endpoint, we observed an increase in phosphorylated MAP kinase levels when CHO cells expressing either the human or the rat GALR2 receptor were incubated for 10 minutes with human galanin (10 µM). These two assays (GTPγ$^{35}$S binding and MAP kinase activation) are useful alternatives to assays described previously and may in some cases have particular advantages regarding, for example, speed, throughput, reliability, sensitivity or reagent handling.

Feeding Assays

Rats were injected icv with either galanin, galanin derivatives, or saline. Cumulative food intake was measured over a period of 3 hours. Baseline food intake associated with the saline control was 1.5 gram. A maximal food intake of 6.81 grams was observed after a 10 mmole injection of galanin. The ED$_{50}$ for galanin is estimated to be 1 mmole. M40 was also tested in this paradigm. M40 was able to mimic the effects of galanin, with a maximal food intake of 6.3 grams observed after a 50 mmol injection. The ED$_{50}$ for M40 is estimated to be 20 mmoles. Another peptide, which was found to bind selectively to GALR2 over both GALR3 and GALR1, stimulated feeding in rats when administered by i.c.v. injection. This result suggests that GALR2 may mediate galanin-induced feeding behavior.

Heterologous Expression of GPCRs in *Xenopus* Oocytes

Heterologous expression of GPCRs in *Xenopus* oocytes has been widely used to determine the identity of signaling pathways activated by agonist stimulation (Gundersen et al., 1983; Takahashi et al., 1987). Application of porcine galanin (100–1000 nM) activates rapid inward currents in 36 of 46 oocytes injected with 5–50 pg rGalR2 mRNA (FIG. 13). Equimolar concentrations of C7 induces similar currents whereas galanin 3–29 is inactive (0/11 oocytes). Oocytes injected with buffer (ND96) alone or 5-HT1a receptor mRNA do not exhibit detectable (<5 nA) responses to galanin (0/19) Current magnitudes in rGalR2 mRNA-injected oocytes range from small fluctuations of less than 50 nA (excluded from analysis) to large rapid currents (up to 3 µA) resembling those activated by stimulation of other receptors (alpha1a receptors—data not shown) that are known to couple to IP3 release and stimulation of Cl– current from the resulting increase in intracellular free Ca$^{++}$ (Takahashi et al., 1987). The currents stimulated by galanin in oocytes expressing rGalR2 are most likely mediated by the endogenous calcium-activated Cl channel (Gunderson et al., 1983) because they are blocked in oocytes injected with 50 nl of 10 mM EGTA (5/5) and they display a current-voltage relation that exhibits outward rectification and a reversal potential of approximately –15 mV (data not shown).

Another functional assay which may be performed using the oocyte expression system utilizes aequorin. Aequorin, a luminescent photoprotein isolated from jellyfish, emits blue light upon binding calcium. Thus, aequorin is a useful tool to detect expression of receptors that trigger the release of intracellular calcium upon agonist stimulation. Application of galanin to oocytes that are injected with aequorin protein alone produces an average response of 1,140 relative light units (N=4). In contrast, oocytes injected with both rGalR2 mRNA and aequorin protein yield a response of 16,700 relative light units (N=5). Analysis of the time course of luminescence indicates that the oocytes which do not contain rGalR2 mRNA give off a constant, low level luminescence during the two minute recording interval. However, oocytes expressing the rGalR2 receptor emit light in a time dependent fashion with a peak luminescence at about 40 seconds after the addition of galanin. This time course is consistent with that seen for other G protein-coupled receptors whose expression has been monitored by aequorin.

Receptor Autoradiography

The relative proportion of the total [$^{125}$I]galanin binding attributable to the GALR2 receptor was determined as the binding which was removed by 60 nM [D-Trp$^2$]galanin$_{(1-29)}$. The numerical representations in Table 2 indicate: 1) the relative intensity of the total binding obtained with [$^{125}$I] galanin, with +3 being the maximum; and 2) the relative amount of this binding attributable to GALR2, with +3 again being the maximum.

Total [$^{125}$I]galanin binding was observed in many regions of the rat brain, and was especially intense in the forebrain, including the amygdala, parts of the hypothalamus and thalamus, the septum, and the ventral hippocampus. Other regions with intense binding signals included the superior colliculus, the central gray, and the dorsal horn of the spinal cord. The inclusion of 5 μM porcine galanin in the incubation resulted in a complete displacement of [$^{125}$I]galanin binding from the rat brain tissue sections. The use of 60 nM [D-Trp$^2$]galanin$_{(1-29)}$ partially displaced [$^{125}$I]galanin binding from many regions of the rat brain.

The areas most affected by the GALR2 selective ligand were the lateral septum, the paraventricular hypothalamic nucleus, the centromedial and centrolateral thalamic nuclei, the amygdalopiriform area of the amygdala, and the superior colliculus. Other forebrain regions with lesser but still significant reductions in [$^{125}$I]galanin binding included the piriform and entorhinal cortices, the globus pallidus, the supraoptic, lateral, and ventromedial hypothalamic nuclei, and the anterior, cortical, medial, and central amygdaloid nuclei. In the midbrain, pons and medulla, [D-Trp$^2$]galanin$_{(1-29)}$ partially reduced the total binding in the central gray, the raphe obscurus and raphe magnus, the parabrachial nucleus, the pontine reticular formation, the hypoglossal nucleus, and the gigantocellular reticular nucleus.

In contrast, there were a number of areas in which [D-Trp$_2$]galanin$_{(1-29)}$ had little or no effect on the total [$^{125}$I]galanin binding. Of these, the most striking were the nucleus of the lateral olfactory tract, the ventral hippocampus, and the dorsal horn of the spinal cord other areas in which significant binding remained included the olfactory bulb, the insular cortex, the islands of Calleja, the nucleus accumbens, the lateral habenula, the arcuate nucleus, and the spinal trigeminal nucleus.

Developmental In Situ Hybridization

Using oligonucleotide probes, GalR2 mRNA appeared to be developmentally regulated. At P1 and P5, film autoradiography of the hybridized brain sections revealed clear signals over many thalamic nuclei. In the hypothalamus, both the paraventricular and ventromedial nuclei were labeled. In addition, the superficial layers of neocortex contained visible hybridization signal, as did the dorsal hippocampus. In the mesencephalon, a low level of hybridization signal was observed in the pretectal region.

Ribonuclease Protection Assay

RNA was isolated and assayed as described from: heart, striated muscle, liver, kidney, and CNS regions. CNS regions included: spinal cord, amygdala, hypothalamus, cerebral cortex, cerebellum, and hippocampus. The highest levels of rGalR2 were detected in the hypothalamus (FIG. 14). Lower amounts were found in heart, kidney, hippocampus amygdala, spinal cord, and cerebellum (FIG. 14). mRNA coding for the rGalR2 was not detected in RNA extracted from striated muscle or liver.

Generation of Human GALR2 PCR Product:

Using PCR primers designed against the fourth and sixth transmembrane domains of the rat GALR2 sequence, NS 525 and NS526, a 300 base pair fragment was amplified from 3 different lots of human genomic DNA. Sequence from all three human genomic DNAs were >98% identical and displayed 84% nucleotide identity to the rat GALR2 gene, between the second extracellular domain and the 5' end of the sixth transmembrane. This level of homology is typical of a species homologue relationship in the GPCR superfamily.

5' and 3' RACE Analysis of Human GALR2

5' RACE was performed on human brain RNA to isolate hGALR2 sequence upstream of the genomic PCR product above. Using nested reverse primers from the fifth transmembrane domain of hGALR2, a 600 base pair fragment was amplified. The sequence of this RACE product displayed 91% nucleotide identity to rGALR2 from the 3' end of the second transmembrane domain to the 5' end of the fifth transmembrane domain.

3' RACE was performed on human lung RNA to determine the sequence of the COOH terminus of hGALR2. Using nested forward primers from the fifth transmembrane domain of hGlR2, a 500 bp RACE product was generated that showed a 77% identity to nucleotides 1080–1139 of rGALR2. The sequence of this RACE product downstream from this region showed less homology to rGALR2, and was presumed to represent the COOH terminus and 3' UT of the hGALR2 gene.

Construction and Screening of a Human Heart cDNA Library

To obtain a full-length hGALR2 clone, superpools of a human heart cDNA library were screened by PCR using primers BB153 and BB169. A 325 base pair fragment was amplified from superpools 6, 9 and 16. Two positive primary pools, 69 and 72, were identified from superpool 9, and 1 positive primary pool, 121, was identified from superpool 16. One positive primary pool, 69, was subdivided into 48 pools of 3333 individual clones and screened by PCR. Twelve positive subpools were identified and one, 69-11, was subdivided into 20 pools of 1200 clones, plated onto agar plates, and screened by southern analysis. Thirty colonies that appeared positive were rescreened by PCR using primers BB167 and BB170, revealing 4 positive colonies. One of these, 69-11-5 was chosen for further analysis. To evaluate whether this colony represented a single clone, a dilution of the colony was amplified on agar plates and colonies were screened by PCR using primers BB167 and BB170. Five of 20 colonies were positive for hGALR2, indicating that 69-11-5 was a mixture of 2 or more clones. One positive colony, 69-11-5-3, designated BO29, was amplified as a single hGlR2 clone. Vector-anchored PC-R revealed that BO29 is in the correct orientation for expression, and encodes approximately 200 base pairs of 5'UT and 5000 base pairs 3'UT. Preliminary single-stranded sequence analysis indicates that BO29 encodes an initiating methionine and a termination codon, and contains an intron between the third and fourth transmembrane domains which is approximately 1.2 kb in length. 69-11-5 has been demonstrated to confer $^{125}$I galanin binding in transfected COS-7 cells, as assessed by microscopic analysis of photoemulsion-dipped slides. In addition, COS-7 cells transfected with the single clone BO29 exhibit significant binding of $^{125}$I galanin in comparison with COS-7 cells transfected with control vector. In preliminary radioligand binding experiments, $^{125}$I porcine galanin bound to membranes from COS-7 cells transfected with BO29, with a specific binding of 4900 fmol/mg, when the membranes (0.005 mg/ml) were incubated with 0.4 nM porcine galanin for 30 min. at 30° C. No specific binding was detected to membranes from mock-transfected COS-7 cells when tested under the same conditions.

Human GALR2 Receptor Pharmacology

A human GALR2 receptor construct containing an intron in the coding region of the cDNA (BO29) was prepared and transiently transfected into COS-7 cells. Human GALR2 receptors expressed in the COS-7 cell membranes were labeled by porcine $^{125}$I-galanin with an apparent $B_{max}$ of 4200 fmol/mg membrane protein and a $K_d$ of 0.97 nM. The peptide binding profile for the human GALR2 receptor (Table 8) resembled that reported previously for the rat GALR2 in COS-7 cell membranes (Table 1).

A human GALR2 receptor cDNA construct lacking the intron in the coding region was also prepared (BO39) and transiently transfected into COS-7 cells. In a preliminary experiment, membranes from transiently transfected cells (membrane protein concentration=0.045 mg/ml) were incubated with porcine $^{125}$I-galanin (0.17 nM), and specific binding was measured as 480 fmol/mg membrane protein. Assuming an estimated $K_d$ of 1 nM, the estimated $B_{max}$ for this construct would be ~3400 fmol/mg membrane protein. Therefore, it is concluded that the absence of the intron in the coding region of the human GALR2 cDNA has no significant effect on receptor expression or porcine $^{125}$I-galanin binding.

Human GALR2 Localization by RT-PCR

RT-PCR was performed on human cDNAs from various brain regions and peripheral tissues. The primers used were BB182 (reverse primer from hGALR2 stop codon) and BB183 (forward primer from hGalR2 start codon); see methods. The PCR products were Southern blotted and hybridized with a $^{32}$P-labeled oligonucleotide probe (BB247). Of the tissues examined, the highest levels were found in the heart and kidney, with high levels also detected in hypothalamus, liver and small intestine. Moderate levels were detected in hippocampus, and somewhat lower levels were found in the retina. No signal was detected in cerebral cortex, adrenal gland, lung, lymph node, spleen or stomach.

Experimental Discussion

In order to clone additional members of the galanin receptor family, an expression cloning strategy based on the potential presence of multiple galanin receptors in the hypothalamus was designed. Using this strategy a cDNA clone encoding a galanin receptor from rat hypothalamus, termed GALR2, was isolated that is distinct from the previously cloned GALR1 receptors.

Transient transfection of the isolated cDNA (K985) encoding GALR2 resulted in high affinity binding of [$^{125}$I]-porcine galanin. The high binding affinity of the GALR2 receptor for galanin$_{(1-29)}$, and its truncated analogs galanin$_{(1-16)}$ and galanin$_{(1-15)}$ strongly supports the notion that the GALR2 receptor is a novel galanin receptor subtype. Both the rat GALR1 and GALR2 receptors seem to bind preferentially to the amino terminus of galanin. Deletion of 13 or 14 amino acids from the carboxyl terminus of galanin still yields peptides with high binding affinity at both the GALR1 and GALR2 receptors. Furthermore, the truncation of the first two amino acids of the amino terminus led to a complete loss of affinity at both GALR1 and GALR2. Consistent with this notion are the findings that the chimeric peptides, which share identical amino acid sequences in the first 12 amino acids with galanin had very similar binding affinities for either GALR1 or GALR2 receptors. In spite of these similarities, the substitution of L-tryptophan with D-tryptophan in position 2 of porcine galanin$_{(1-29)}$ ([D-Trp$^2$]galanin$_{(1-29)}$) led to a 7,000-fold loss in affinity at the GALR1 receptor compared to only a 14-fold reduction at the GALR2 receptor. The same substitution in the truncated analog galanin$_{(1-16)}$ led to a 4,200-fold reduction in affinity at the GALR1 receptor, and only a 6-fold reduction in affinity at the GALR2 receptor. Relative to porcine galanin, D-Trp2-(3-iodo-L-Tyr9)-(-iodo-L-Tyr26)-galanin was much more potent as a GalR2 agonist (only 1.5-fold less potent in arachidonic acid assays) than as a GalR1 agonist (15,000-fold less potent in cAMP assays; see Table 7). These data suggest that galanin analogs, with modifications at the 2-position, are better tolerated at the GALR2 receptor than at the GALR1 receptor as long as the side chain is an aromatic moiety. The data further suggest that the D-Trp2-galanin analogs may be used as tools to differentiate GalR2 from GalR1-dependent processes.

Conversely, the substitution of tyrosine with alanine in position 9 of galanin$_{(1-16)}$, (i.e., to make [Ala]$^9$ galanin) leads to a 680-fold reduction in affinity at the GALR1 receptor and to a 60,000-fold reduction in affinity at the GALR2 receptor. Altogether, the major differences in binding selectivity of the substituted analogs of galanin suggest the existence of substantial differences in the binding domains of these two receptor subtypes.

The existence of such structural differences between the GALR1 and GALR2 receptors are indicative of the potential for the design and discovery of novel subtype selective compounds. In this regard, the expression of the cDNA encoding the rat GALR2 receptors in cultured cell lines provides a unique tool for the discovery of therapeutic agents targeted at galanin receptors.

Localization of Galanin Receptors

The high affinity of [D-Trp$^2$]galanin$_{(1-29)}$ for the cloned GALR2 receptor (6 nM), and its low affinity for the GALR1 receptor (3 µM), makes it a useful tool for receptor autoradiographic studies. Thus, brain areas in which the total [$^{125}$I]galanin binding is significantly reduced by [D-Trp$_2$]galanin$_{(1-29)}$ are interpreted as areas containing a high proportion of GALR2 receptors, or other galanin receptors with similar high affinity for [D-Trp$^2$]galanin$_{(1-29)}$. Those with lesser reductions are seen as regions containing a higher concentration of GALR1 receptors. The lateral septum, the paraventricular hypothalamic nucleus, the centromedial and centrolateral thalamic nuclei, the amygdalopiriform area of the amygdala, and the superior colliculus all appear to contain primarily GALR2 receptors. In contrast, the nucleus of the lateral olfactory tract, the ventral hippocampus, and the dorsal horn of the spinal cord appear to contain primarily GALR1 receptors. The predominance of the GALR1 receptor in these regions is consistent with published reports of the GALR1 messenger RNA localization (Parker et. al., 1995; Gustafson et al., 1996). In most other regions, there appears to be a significant overlap between the two subtypes.

While the functional implications of the GALR2 receptor localization are not well understood at present, there are a number of physiological processes attributable to galanin that could be mediated by this receptor. These include feeding (paraventricular hypothalamic nucleus), cognition (septum and hippocampus), analgesia and/or sensory processing (midline thalamic nuclei), and anxiety and depression (amygdala and hypothalamus).

The observation that galanin is co-released with norepinephrine from sympathetic nerve terminals suggests that galanin could act via galanin receptors in the periphery to modulate nearly every physiological process controlled by sympathetic innervation. Additional therapeutic indications not directly related to localization (supra) include diabetes, hypertension, cardiovascular disorders, regulation of growth hormone release, regulation of fertility, gastric ulcers, gastrointestinal motility/transit/absorption/secretion, glaucoma, inflammation, immune disorders, respiratory disorders (eg. asthma, emphysema).

The physiological and anatomical distribution of galanin-containing neurons suggests potential roles of galanin receptors mediating effects on cognition, analgesia, neuroendocrine regulation, control of insulin release and control of feeding behavior. Of particular relevance to the role of the novel GALR2 receptor, are those functions mediated by galanin receptors in the rat hypothalamus.

Studies in rats indicate that the injection of galanin in the hypothalamus increases food intake (Kyrouli et al, 1990, and Schick et al, 1993) and that this stimulatory effect of galanin is blocked by prior administration of M40 and C7 (Liebowitz and Kim, 1992; and Corwin, 1993). The expression of the mRNA encoding the GALR1 receptor in the rat hypothalamus, (Parker et al., 1995, Gustafson et al., 1996) and the fact that the novel GALR2 receptor was cloned from a cDNA library prepared from rat hypothalamus argues in favor of either receptor subtype to be involved in the regulation of feeding behavior (Parker et al., 1996). However, the evidence against the involvement of GALR1 in the stimulation of feeding behavior stems from the fact that M40 and C7 are known to be agonists, and not antagonists, in cell lines expressing the cloned human and rat GALR1 receptors (Heuillet et al. 1994; Hale et al. 1993; and Bartfai et al. 1993).

The distribution of GALR2 mRNA in the rat brain and periphery has been determined by ribonuclease protection assay, in situ hybridization, Northern blot analysis and RT-PCR. The results of these studies suggest that this receptor is potentially involved in mediating many of the physiological roles ascribed to the peptide galanin. In the adult rat, localization of the GalR2 mRNA in the hypothalamus indicates a role for this receptor in homeostatic mechanisms, including food intake and neuroendocrine regulation. The presence of GALR2 mRNA in the neocortex and dorsal hippocampus suggest an involvement in cognition, which is consistent with documented changes in galanin and galanin receptor expression during aging and in the brains of Alzheimer's patients (Chan-Palay, 1988; Leverenz et al., 1996). Galanin also has antinociceptive effects, and the localization of GALR2 mRNA in the spinal cord (present investigation) and dorsal root ganglia (O'Donnell et al., 1996) implicate this receptor in pain neurotransmission. The localization of GALR2 mRNA in the cerebellum is intriguing, as it suggests a role for galanin and the GalR2 receptor in planned movements and potentially in movement disorders.

In addition to the localization observed in adult animals, it also appears that the GALR2 mRNA is developmentally regulated, with the highest levels observed early in postnatal development. Thus, it is possible that this galanin receptor plays a role in developmental processes which occur during the first postnatal week, such as axonal guidance and synapse formation.

A unique pharmacological profile for the GALR2 receptor has been generated through binding and functional assays. This profile can be used to deduce the physiological function of the GalR2 receptor in vivo. Consider the agonist activity of galanin 1–16, for example. Galanin 1–16 is reported to function as an agonist in various models of hypothalamic, pituitary and pancreatic function (Kask et al.) Galanin 1–16 is also reported to mimic the effects of galanin on the flexor reflex in the rat. The N-terminally extended peptides galanin (−7) to (+)29 and galanin (−9) to (+)29, also characterized as rat GALR2 agonists, can mimic the effects of galanin in a rat flexor reflex assay (Weisenfeld). Taken together, these data suggest a potential role for the rat GalR2 receptor in a range of physiology or pathophysiology including diabetes, pain, reproduction, obesity and eating disorders.

The agonist activity of M40 in GALR2 in vitro assays is particularly intriguing when viewed in the context of behavioral feeding models. From the literature, one might conclude that the agonist activity of M40 in vitro is in apparent conflict with the antagonist activity reported for M40 in behavioral models of food intake, and 2b that the GALR2 receptor is therefore unlikely to mediate the feeding response. The data generated and reported in the subject application do not support this conclusion. Rather, the data from behavioral feeding models indicate that M40 is an orexigenic peptide whose maximal effect is comparable to that for galanin itself. The agonist activity reported herein for M40 both in vitro and in vivo is consistent with the proposal that the rat GALR2 receptor mediates the stimulatory effect of galanin on food intake in the central nervous system. These data further suggest that the rat GALR2 receptor represents a target for the design of therapeutic compounds for the treatment of obesity and related disorders.

TABLE 1

Binding of galanin peptide analogs to the recombinant rat GALR1 and GALR2 receptors transiently expressed in COS 7 cells.

| Analog | GALR1 (pKi) | | GALR2 (pKi) | |
| --- | --- | --- | --- | --- |
| | Mean | SEM* | Mean | SEM |
| porcine galanin $_{(1-29)}$ | 9.34 | 0.15 | 9.35 | 0.14 |
| [D-Trp$^2$] porcine galanin $_{(1-29)}$ | 5.46 | 0.04 | 8.19 | 0.26 |
| [Phe$^2$] porcine galanin $_{(1-29)}$ | 5.99 | 0.13 | 5.64 | 0.11 |
| [D-Ala$^7$] porcine galanin $_{(1-29)}$ | 8.66 | 0.04 | 8.76 | 0.09 |
| galanin $_{(1-16)}$ | 8.66 | 0.01 | 8.76 | 0.13 |
| [D-Trp$^2$] galanin $_{(1-16)}$ | 4.40 | 0.09 | 8.02 | 0.10 |
| [Ala$^5$] galanin $_{(1-16)}$ | 6.27 | 0.05 | 7.46 | 0.13 |
| [Ala$^9$] galanin $_{(1-16)}$ | 5.83 | 0.02 | 3.98 | 0.10 |
| galanin $_{(1-15)}$ | 8.47 | 0.04 | 9.19 | 0.06 |
| [Phe$^2$] galanin $_{(1-15)}$ | 4.63 | 0.03 | 5.85 | 0.49 |
| porcine galanin $_{(3-29)}$ | <4.0 | | <4.0 | |
| galantide | 8.02 | 0.08 | 8.70 | 0.07 |
| C-7 | 7.79 | 0.01 | 7.72 | 0.09 |
| M32 | 9.21 | 0.10 | 9.23 | 0.05 |
| M35 | 9.48 | 0.07 | 9.24 | 0.10 |
| M40 | 8.44 | 0.09 | 9.14 | 0.21 |

*SEM = standard error of the mean, from 3 independent experiments.

TABLE 2

Distribution of [$^{125}$I]galanin binding in rat brain. Total binding is compared to the amount attributable to GALR2 (as indicated by displacement of [$^{125}$I]galanin by 60 nM [D-Trp$^2$]porcine galanin$_{(1-29)}$).

| Region | Total [$^{125}$I]Gal binding | Putative GALR2 sites | Potential Applications |
|---|---|---|---|
| Olfactory bulb | +3 | +1 | Modulation of olfactory sensation |
| Anterior olfactory n. | +3 | +1 | Modulation of olfactory sensation |
| Cortex | | | |
| dorsal neocortex, layer 4 | +1 | +1 | Sensory integration |
| piriform | +2 | +1 | Modulation of olfactory sensation |
| agranular insular | +3 | +1 | Processing of visceral information |
| entorhinal | +2 | +1 | |
| dorsal endopiriform | +2 | +1 | |
| Claustrum | +2 | +1 | Visual processing |
| Basal ganglia | | | |
| n. accumbens | +2 | 0 | Modulation of dopaminergic function |
| olfactory tubercle | +2 | +1 | |
| globus pallidus | +1 | +1 | |
| islands of Calleja | +3 | +1 | |
| Septal area | | | |
| lateral septum | +3 | +2 | Cognitive enhancement via cholinergic system |
| diagonal band n. | +2 | 0 | |
| Hypotalamus | | | |
| anterior | +1 | 0 | Neuroendocrine regulation |
| supraoptic n. | +2 | +1 | |
| paraventricular | +2 | +2 | Appetite/obesity |
| ventromedial | +2 | +1 | |
| arcuate | +1 | 0 | |
| lateral | +2 | +1 | |
| medial mammillary | +2 | +1 | |
| Thalamus | | | |
| paraventricular n. | +1 | 0 | Analgesia/sensory modulation |
| centromedial | +3 | +2 | |
| paracentral | +3 | +1 | |
| rhomboid | +1 | 0 | |
| reuniens | +2 | +1 | |
| mediodorsal | +2 | +1 | |
| reticular n. | +1 | +½ | |
| centrolateral n. | +3 | +2 | |
| zona incerta | +2 | +1 | |
| lateral dorsal | +1 | +½ | |
| habenula | +3 | +1 | Anxiety/sleep disorders |
| Hippocampus | | | |
| Cal, ventral | +3 | 0 | Cognition enhancement/ ischaemia |
| subiculum | +2 | +1 | |
| Amygdala | | | |
| bed n. stria terminalis | +3 | +1 | Anxiolytic, appetite, depression |
| n. lateral olfactory tract | +3 | 0 | |
| Amygdala | | | |
| anterior | +2 | +1 | Anxiolytic, appetite, |
| medial | +3 | +1 | |
| cortical | +2 | +1 | depression |
| central | +3 | +1 | |
| amygdalohippocampal | +2 | 0 | |
| amygdalopiriform | +3 | +2 | |
| Midbrain | | | |
| superior colliculus | +3 | +2 | Visual function |
| raphe obscurus | +2 | +1 | Analgesia |
| central gray | +2 | +1 | Analgesia |
| Pons/medulla | | | |
| raphe magnus | +2 | +1 | Analgesia |
| parabrachial n. | +2 | +1 | |
| pontine ret. n. | +2 | +1 | |
| reticulotegmental | +2 | +1 | |
| gigantocellular | +2 | +1 | |
| motor trigeminal | +1 | 0 | |
| spinal trigeminal | +3 | +1 | Migraine |
| hypoglossal n. | +2 | +1 | Motor coordination |
| area postrema | +1 | 0 | |
| Spinal cord | | | |
| dorsal horn | +3 | +1 | Analgesia |

TABLE 3

Northern blot hybridization of GALR2 receptor in brain and various peripheral rat tissues.

| Tissue | Blot 1 | Blot 2 | Mean Signal | Therapeutic Indications |
|---|---|---|---|---|
| Heart | +++ | ++ | 2.5 | Cardiovascular Indications (including hypertension and heart failure) |
| Brain | ++++ | ++++ | 4.0 | obesity/feeding, analgesia, cognition enhancement, Alzheimer's disease, depression, anxiety, sleep disorders, Parkinson's disease, traumatic brain injury, convulsion/epilepsy |
| Spleen | ++ | ++ | 2.0 | Immune functions, hematopoiesis |
| Lung | ++++ | ++++ | 4.0 | Respiratory disorders; asthma, emphysema, lung cancer diagnostics |
| Liver | ++ | − | 1.0 | Diabetes |
| Skeletal Muscle | + | ++ | 1.5 | Diabetes |
| Kidney | +++ | +++ | 3.0 | Hypertension, electrolyte balance, diuretic, anti-diuretic |
| Testis | +++ | + | 2.0 | Reproductive function |

TABLE 4

Inositol phosphate hydrolysis in LM(tk−) cells stably transfected with GALR2.

| Peptide | $EC_{50}$ PI (nM) rat GALR2 (with intron) | $EC_{50}$ PI (nM) L-rGALR2I-4 (intronless) |
|---|---|---|
| porcine galanin | 21 | 14 |
| M35 | 29 | 28 |
| D-Trp$^2$-galanin 1–16 | 1380 | 660 |
| D-Trp$^2$-galanin 1–29 | 200 | 230 |
| galanin 1–16 | 65 | 18 |
| M40 | 28 | 47 |
| M32 | 13 | 35 |

TABLE 5

Rat GALR2 receptors stably transfected in CHO Comparison of binding data, phosphatidyl inositol release, and arachidonic acid release in C-rGalR2-79.

| Peptide | $K_i$ from porcine $^{125}$I-galanin binding assays (nM) | $EC_{50}$ from PI hydrolysis assays (nM) | $EC_{50}$ from arachidonic acid assays (nM) |
|---|---|---|---|
| rat galanin | 0.52 | 14 | 0.67 |
| porcine galanin | 0.94 | 15 | 1.3 |
| porcine galanin 1–16 | 3.5 | 91 | 2.6 |
| D-Trp$^2$-galanin 1–16 | 110 | 590 | 50 |
| D-Trp$^2$- (3-iodo-L-Tyr9) - (3-iodo-L-Tyr26) -galanin | — | 580 | 2.0 |
| porcine galanin (−7) to (+) 29 | — | 220 | 3.9 |
| porcine galanin (−9) to (+) 29 | — | — | 2.8 |
| porcine galanin (1–15) | 1.5 | 200 | 2.3 |
| porcine galanin (3–29) | >1000 | >1000 | >1000 |
| galantide | 4.9 | 11 | 0.93 |
| C7 | 48 | 11 | 2.4 |
| M32 | 5.6 | 14 | 2.5 |
| M35 | 3.4 | 44 | 1.3 |
| M40 | 3.5 | 58 | 2.7 |

TABLE 6

CHO GALR2 pharmacology: binding ($K_i$ vs. $^{125}$I-porcine galanin) vs. function (arachidonic acid hydrolysis)

| Peptide | Rat GALR2 $K_i$, C-rGalR2-79 (nM) | Rat GALR2 $EC_{50}$ AA, C-rGalR2-79 (nM) |
|---|---|---|
| Human galanin | 1.2 | |
| Porcine galanin | 0.94 | 1.3 |
| rat galanin | 0.52 | 0.67 |
| porcine gal −7 to +29 | | 3.0 |
| porcine galanin −9 to +29 | | 4.0 |
| porcine galanin 3-iodo-L-Tyr9-galanin | | 0.8 |
| porcine galanin 3-iodo-L-Tyr26 galanin | | 1.0 |
| porcine Phe2-galanin | >1000 | |
| porcine D-Trp2-galanin | 41 | 11 |
| D-Trp2-3-iodo-L-Tyr9- | | 3.0 |
| porcine D-Trp2-3-iodo-L-Tyr26-galanin | | 6.0 |
| D-Trp2-(3-iodo-L-Tyr9)-(3-iodo-L-Tyr26)-galanin | | 2.0 |
| D-Ala7-galanin | 6.2 | 5.4 |
| porcine galanin 3–29 | >1000 | >1000 |
| porcine galanin 9–29 | >1000 | >1000 |
| porcine galanin 17–29 | >1000 | |
| porcine galanin 1–16 | 3.5 | 2.6 |
| porcine Ala2-galanin 1–16 | >1000 | |
| porcine D-Trp2-galanin 1–16 | 110 | 50 |
| porcine Ala5-galanin 1–16 | >620 | |
| porcine Ala9-galanin 1–16 | >1000 | |
| porcine galanin 1–15 | 1.5 | 2.3 |
| Phe2-galanin 1–16 | >1000 | >1000 |
| porcine galanin 1–12 | 2.1 | 2.3 |
| porcine galanin 1–9 | >1000 | >1000 |
| C7 | 48 | 2.4 |
| Galantide | 4.9 | 0.93 |
| M32 | 3.4 | 2.5 |
| M35 | 5.8 | 1.3 |
| M40 | 3.5 | 2.7 |

TABLE 7

Peptide-dependent activation of rat GALR1 vs. rat GALR2.

| Peptide | LM(tk−) Rat GALR1 cAMP assay $EC_{50}$ (nM) | C-RGalR2-79 arachidonic acid assay $EC_{50}$ (nM) |
|---|---|---|
| Porcine galanin | 0.06 | 1.3 |
| rat galanin | 0.05 | 0.67 |
| porcine D-Trp$^2$-galanin | >850 | 11 |
| porcine galanin 3–29 | >1000 | >1000 |
| porcine galanin 1–16 | 0.34 | 2.6 |
| porcine D-Trp$^2$-galanin 1–16 | >1000 | 50 |
| C7 | 0.52 | 2.4 |
| Galantide | 0.08 | 0.93 |
| M32 | 0.34 | 2.5 |
| M35 | 0.15 | 1.3 |
| M40 | 0.82 | 2.7 |
| D-Trp2- (3-iodo-L-Tyr9) - (3-iodo-L-Tyr26) -galanin | 900 | 2.0 |
| porcine galanin (−7) to (+29) | 21 | 3.9 |
| porcine galanin (−9) to (+29) | 24 | 2.8 |

TABLE 8

Peptide binding profile: Human GALR2 vs. rat GALR2 transiently expressed in COS-7

| Peptide | Human GALR2 $K_i$ (nM) | Rat GALR2 $K_i$ (nM) |
|---|---|---|
| porcine galanin 1–16 | 15 | 7.2* |
| porcine galanin | 0.72 | 0.45 |

TABLE 8-continued

Peptide binding profile: Human GALR2 vs. rat GALR2 transiently expressed in COS-7

| Peptide | Human GALR2 $K_i$ (nM) | Rat GALR2 $K_i$ (nM) |
|---|---|---|
| M40 | 5.3 | 0.72 |
| porcine D-Trp$^2$-galanin | 290 | 52* |
| M32 | 7.9 | 12* |
| rat galanin | 1.0 | 0.52* |

*additional experiments were performed with some of the peptides shown in Table 1.

REFERENCES

Ahrén, B. and S. Lindskog (1992) *Int. J. Pancreatol.* 11:147–160.

Amiranoff, B. A. M. Lorinet, and M. Laburthe (1991) *Eur. J. Biochem.* 195:459–463.

Amiranoff, B. A. L. Servin, C. Rouyer-Fessard, A. Couvineau, K. Tatemoto, and M. Laburthe (1987) *Endocrin.* 121:284–289.

Aruffo, A. and B. Seed (1987) *Proc. Natl. Acad. Sci. USA* 84:8573–8577.

Bhathena, S. J., H. K. Oie, A. F. Gazdar, N. R. Voyles, S. D. Wilkins, and L. Recant (1982) *Diabetes* 31:521–531.

Bartfai, T., K. Bedecs, T. Land, Ü. Langel, R. Bertorelli, P. Girotti, S. Consolo, Y.-J. Yu, Z. Weisenfeld-Hallin, S. Nilsson, V. Pieribone, and T. Hökfelt (1991) *Proc. Natl. Acad. Sci. USA* 88:10961–10965.

Bartfai, T., T. Hokfelt, and U. Langel, *Crit. Rev. Neurobiol.* 7:229–274.

Bartfai, T., Ü. Langel, K. Bedecs, S. Andell, T. Land, S. Gregersen, B. Ahren, P. Girotti, S. Consolo, R. Corwin, J. Crawley, X. Xu, Z. Weisenfeld-Hallin, and T. Hökfelt (1993) *Proc. Natl. Acad. Sci. USA* 88:11287–11291.

Bennet, W. M., S. F. Hill, M. A. Ghatei, and S. R. Bloom (1991) *J. Endocrin.* 130:463–467.

Borden, L. A., K. E. Smith., P. R. Hartig, T. A. Branchek, and R. L. Weinshank (1992) *J. Biol. Chem.* 267: 21098–21104.

Borden, L. A., K. E. Smith, E. L. Gustafson, T. A. Branchek, and R. L. Weinshank (1995) *J. Neurochem.* 64977–984.

Boyle, M. R., C. B. Verchere, G. McKnight, S. Mathews, K. Walker, and G. J. Taborsky, Jr. (1994) *Reg. Peptides* 50:1–11.

Bradford, M. M. (1976). A rapid and sensitive method for the quantitation of microgram quantities of protein utilizing the principle of protein-dye binding. *Anal. Biochem.* 72: 248–254.

Burbach, J. P. and O. C. Meijer (1992) *Eur. J. Pharmacol.* 227:1–18.

Burgevin, M.-C., Loquet, I., Quarteronet, D., and Habert-Ortoli, E. (1995) *J. Molec. Neurosci.,* 6:33–41.

Burns, C. M., Chu, H., Rueter, S. M., Sanders-Bush, E., and R. B. Erneson. (1996) *Neuroscience Abstracts* 385.9.

Bush, A. W., Borden, L. A., Greene, L. A., and Maxfield, F. R. (1991) *J. Neurochem.* 57:562–574.

Chan-Palay, V. (1988) *J. Comp. Neurol.* 273:543–557. Chen, Y., A. Fournier, A. Couvineau, M. Laburthe, and B. Amiranoff (1993) *Proc. Natl. Acad. Sci. USA* 90:3845–3849.

Chirgwin, J. M., A. E. Przybyla, R. J. MacDonald, and W. J. Rutter. (1979) *Biochemistry* 18:5294–5299.

Chu, H., Burns, C., Canton, H., Emeson, R. B., and E. Sanders-Bush. (1996) *Neuroscience Abstracts* 385.10.

Consolo, S., R. Bertorelli, P. Girotti, C. La Porta, T. Bartfai, M. Parenti, and M. Zambelli (1991) *Neurosci. Lett.* 126: 29–32.

Crawley, J. N. (1993) *Behav. Brain Res.* 57:133–141.

Crawley, J. N., J. K. Robinson, Ü. Langel, and T. Bartfai (1993) *Brain. Res.* 600:268–272.

Cullen, B. (1987). Use of eukaryotic expression technology in the functional analysis of cloned genes. *Methods Enzymol.* 152: 685–704.

D'Andrea, A. D., H. F. Lodish, and G. W. Gordon (1989) *Cell* 57:277–285.

Fisone, G., C. F. Wu, S. Consolo, Ö. Nördstrom, N. Brynne, T. Bartfai, T. Melander, T. Hökfelt (1987) *Proc. Natl. Acad. Sci USA* 84:7339.

Gearing, D. P., King, J. A., Gough, N. M. and Nicola N. A. (1989) *EMBO J.* 8:3667–3676.

Gerald, C., M. Walker, T. Branchek, and R. Weinshank (1994) DNA Encoding a Human Neuropeptide Y/Peptide YY (Y2) Receptor and Uses Thereof, U.S. patent application Ser. No. 08/192,288, filed Feb. 3, 1994.

Gillison, S. L., and W. G. Sharp (1994) *Diabetes* 43:24–32. Gregersen, S., S. Lindskog, T. Land, U. Langel, T. Bartfai, and B. Ahren (1993) *Eur J. Pharmacol.* 232:35–39.

Gu, Z.-F., W. J. Rossowski, D. H. Coy, T. K. Pradhan, and R. T. Jensen (1993) *J. Phamacol. Exper. Ther.* 266: 912–918.

Gu, Z.-F., Pradhan, T. K., Coy, D. H., and Jensen, R. T. (1995) *J. Pharmacol. Exp. Ther.,* 272:371–378.

Gubler, U abd B. J. Hoffman. (1983). A simple and very efficient method for generating cDNA libraries. *Gene.* 25, 263–269.

Gundersen, C. B., R. Miledi, and I. Parker. 1983. *Proc. R. Soc., London Ser. B* 219:103–109.

Gustafson, E. L., Smith, K. E., Durkin, M. M., Gerald, C., and Branchek, T. A. (1996) *Neuroreport,* 7:953–957.

Habert-Ortoli, E., Amiranoff, B., Loquet, I., Laburthe, M., and J.-F. Mayaux (1994) *Proc. Natl. Acad. Sci. USA* 91:9780–9783.

Hedlund, P. B., N. Yanaihara, and K. Fuxe (1992) *Eur. J. Pharm.* 224:203–205.

Heuillet, E., Bouaiche, Z., Menager, J., Dugay, P., Munoz, N., Dubois, H., Amiranoff, B., Crespo, A., Lavayre, J., Blanchard, J.-C., and Doble, A. (1994) *Eur. J. Pharmacol.,* 269:139–147.

Kaplan, L. M., S. M. Gabriel, J. I. Koenig, M. E. Sunday, E. R. Spindel, J. B. Martin, and W. W. Chin (1988) *Proc. Natl. Acad. Sci. USA* 85:7408–7412.

Kieffer, B., Befort, K., Gaveriaux-Ruff, C. and Hirth, C.G. (1992). The δ-opioid receptor: Isolation of a cDNA by expression cloning and pharmacological characterization. *Proc. Natl. Acad. Sci. USA* 89:12048–12052.

Kluxen, F. W., Bruns, C. and Lubbert H. (1992). Expression cloning of a rat brain somatostatin receptor cDNA. *Proc. Natl. Acad. Sci. USA* 89:4618–4622.

Kornfeld, R. and Kornfeld, S. (1985). Assembly of asparagine linked oligosaccharides. *Annu. Rev. Biochem.* 54:631–664.

Kozak, M. (1989). The scanning model for translation: an update. *J. Cell Biol.* 108: 229–241.

Kozak, M. (1991). Structural features in eukaryotic mRNAs that modulate the initiation of translation. *J. Biol. Chem.* 266: 19867–19870.

Kyrkouli, S. E., B. G. Stanley, R. D. Seirafi and S. F. Leibowitz (1990) *Peptides* 11:995–1001.

Lagny-Pourmir, I., A. M. Lorinet, N. Yanaihara, and M. Laburthe (1989) *Peptides* 10:757–761.

Landschultz, W. H., Johnson, P. F. and S. L. McKnight. (1988). The leucine zipper: a hypothetical structure common to a new class of DNA binding proteins. *Science* 240: 1759–1764.

Leibowitz, S. F. and T. Kim (1992) Brain Res. 599:148–152.

Maggio, R., Vogel Z. and J. Wess. (1993). Coexpression studies with mutant muscarinic/adrenergic receptors provide evidence for intermolecular "cross-talk" between G-protein-linked receptors. *Proc. Natl. Acad. Sci. USA* 90: 3103–3107.

McCormick, M. (1987). Sib Selection. *Methods in Enzymoloqv,* 151: 445–449.

Melander, T., C. Köhler, S. Nilsson, T. Hökfelt, E. Brodin, E. Theodorsson, and T. Bartfai (1988) *J. Chem. Neuroanat.* 1:213–233.

Merchenthaler, I., F. J. López, and A. Negro-Vilar (1993) *Prog. Neurobiol.* 40:711–769.

Miller, J. and Germain, R.N. (1986). Efficient cell surface expression of class II MHC molecules in the absence of associated invariant chain. *J. Exp. Med.* 164: 1478–1489.

Ögren, S.-O., T. Hökfelt, K. Kask, Ü. Langel, and T. Bartfai (1992) *Neurosci.* 51:1.

Palazzi, E., G. Fisone, T. Hökfelt, T. Bartfai, and S. Consolo (1988) *Eur. J. Pharmacol.* 148:479.

Parker, E. M., Izzarelli, D., Nowak, H., Mahle, C., Iben, L., Wang, J., and Goldstein, M. E. (1995) *Mol. Brain Res.,* 34:179–189.

Post, C., L. Alari, and T. Hökfelt (1988) *Acta Physiol. Scand.* 132:583.

Probst, W. C., Snyder, L. A., Schuster, D. I., Brosius, J and Sealfon, S.C. (1992). Sequence alignment of the G-protein coupled receptor superfamily. *DNA and Cell Bio.* 11: 1–20.

Quick, M. W. and H. A. Lester. 1994. Methods for expression of excitability proteins in *Xenopus* oocytes. *Meth. Neurosci.* 19:261–279.

Sanger, S. (1977) *Proc. Natl. Acad. Sci. USA* 74:5463–5467.

Servin, A. L., B. Amiranoff, C. Rouyer-Fessard, K. Tatemoto, and M. Laburthe (1987) *Biochem. Biophys. Res. Comm.* 144:298–306.

Shen, Y., Monsma, F. J. Jr., Metcalf, M. A., Jose, P. A., Hamblin, M. W., and Sibley, D. R. (1993) Molecular Cloning and Expression of a 5-Hydroxytryptamine$_7$ Serotonin Receptor Subtype. *J. Biol. Chem.* 268:18200–18204.

Sims, J. E., C. J. March, D. Cosman, M. B. Widmer, H. R. Macdonald, C. J. McMahan, C. E. Grubin, J. M. Wignal, J. L. Jackson, S. M. Call, D. Freind, A. R. Alpert, S. Gillis, D. L. Urdal, and S. K. Dower (1988) *Science* 241: 585–588.

Skofitsch, G. and D. M. Jacobowitz (1985) *Peptides* 6:509–546.

Skofitsch, G., M. A. Sills, and D. M. Jacobowitz (1986) *Peptides* 7:1029–1042.

Smith, K. E., L. A. Borden, P. R. Hartig, T. Branchek, and R. L. Weinshank (1992) *Neuron* 8: 927–935.

Smith, K. E., L. A. Borden, C-H. D. Wang, P. R. Hartig, T. A. Branchek, and R. L. Weinshank (1992a) *Mol. Pharmacol.* 42:563–569.

Smith, K. E., S. G. Fried, M. M. Durkin, E. L. Gustafson, L. A. Borden, T. A. Branchek, and R. L. Weinshank (1995) *FEBS Letters,* 357:86–92.

Sundström, E., T. Archer, T. Melander, and T. Hökfelt (1988) *Neurosci. Lett.* 88:331.

Takahashi, T., E. Neher, and B. Sakmann. 1987. Rat brain serotonin receptors in *Xenopus* oocytes are coupled by intracellular calcium to endogenous channels. *Proc. Natl. Acad. Sci. USA* 84:5063–6067.

Tempel, D. L., K. J. Leibowitz, and S.F. Leibowitz (1988) *Peptides* 9:300–314.

Vrontakis, M. E., L. M. Peden, M. L Duckworth, and H. G. Friesen (1987) *J. Biol. Chem.* 262:16755–16760.

Warden, D. and H. V. Thorne. (1968). Infectivity of polyoma virus DNA for mouse embryo cells in presence of diethylaminoethyl-dextran. *J. Gen. Virol.* 3: 371.

Wiesenfeld-Hallin, Z., X. J. Xu, J. X. Hao, and T. Hökfelt (1993) *Acta Physiol. Scand.* 147:457–458.

Wiesenfeld-Hallin, Z., et al. (1992) *Proc. Natl. Acad. Sci. USA* 89:3334–3337.

Wynick D., D. M. Smith, M. Ghatei, K. Akinsanya, R. Bhogal, P. Purkiss, P. Byfield, N. Yanaihara, and S. R. Bloom (1993) *Proc. Natl. Acad. Sci. USA* 90:4231–4245.0

---

What is claimed is:

1. A process for determining whether a chemical compound specifically binds to and activates a human or a rat galanin receptor (GALR2), which comprises contacting cells producing a second messenger response and transfected with DNA encoding and expressing on their cell surface the human or the rat galanin receptor (GALR2), or a membrane preparation from such cells, wherein such cells prior to being transfected with such DNA do not normally express the human or rat galanin receptor (GALR2), with the chemical compound under conditions suitable for activation of the human or the rat galanin receptor (GALR2), and measuring the second messenger response in the presence and in the absence of the chemical compound, a change in second messenger response in the presence of the chemical compound indicating that the chemical compound activates the human or the rat galanin receptor (GALR2), wherein the human galanin receptor (GALR2) has an amino acid sequence identical to that (a) shown in SEQ ID NO: 28, (b) expressed by COS-7 cells transfected with plasmid BO29 (ATCC Accession No. 97735) or (c) expressed by COS-7 cells transfected with plasmid BO39 (ATCC Accession No. 97851) and the rat galanin receptor (GALR2) has an amino acid sequence identical to that (a) shown in SEQ ID NO: 8 or (b) expressed by LM(tk−) cells, COS-7 cells or CHO cells transfected with (i) plasmid K985 (ATCC Accession No. 97426) or (ii) plasmid K1045 (ATCC Accession No. 97778).

2. The process of claim 1, wherein the second messenger response comprises arachidonic acid release and the change in second messenger response is an increase in arachidonic acid levels.

3. The process of claim 1, wherein the second messenger response comprises intracellular calcium levels and the change in second messenger response is an increase in intracellular calcium levels.

4. The process of claim 1, wherein the second messenger response comprises inositol phospholipid hydrolysis and the change in second messenger response is an increase in inositol phospholipid hydrolysis.

5. A process for determining whether a chemical compound specifically binds to and inhibits activation of the human or the rat galanin receptor (GALR2), which comprises separately contacting cells producing a second messenger response and transfected with DNA encoding and expressing on their cell surface the human or the rat galanin receptor (GALR2), or a membrane preparation from such cells, wherein such cells prior to being transfected with such DNA do not normally express the human or the rat galanin receptor (GALR2), with both the chemical compound and a second chemical compound known to activate the human or the rat galanin receptor (GALR2), and with only the second chemical compound, under conditions suitable for activation of the human or the rat galanin receptor (GALR2), and measuring the second messenger response in the presence of only the second chemical compound and in the presence of both the second chemical compound and the chemical compound, a smaller change in the second messenger response in the presence of both the chemical compound and the second chemical compound than in the presence of only the second chemical compound indicating that the chemical compound inhibits activation of the human or rat galanin receptor (GALR2), wherein the human galanin receptor (GALR2) has an amino acid sequence identical to that (a) shown in SEQ ID NO: 28, (b) expressed by COS-7 cells transfected with plasmid BO29 (ATCC Accession No. 97735) or (c) expressed by COS-7 cells transfected with plasmid BO39 (ATCC Accession No. 97851), and the rat galanin receptor (GALR2) has an amino acid sequence identical to that (a) shown in SEQ ID NO: 8 or (b) expressed by LM(tk−) cells, COS-7 cells or CHO cells transfected with (i) plasmid K985 (ATCC Accession No. 97426) or (ii) plasmid K1045 (ATCC Accession No. 97778).

6. The process of claim 5, wherein the second messenger response comprises arachidonic acid release, and the change in second messenger response is a smaller increase in the level of arachidonic acid in the presence of both the chemical compound and the second chemical compound than in the presence of only the second chemical compound.

7. The process of claim 5, wherein the second messenger response comprises intracellular calcium levels, and the change in second messenger response is a smaller increase in the level of intracellular calcium in the presence of both the chemical compound and the second chemical compound than in the presence of only the second chemical compound.

8. The process of claim 5, wherein the second messenger response comprises inositol phospholipid hydrolysis, and the change in second messenger response is a smaller increase in inositol phospholipid hydrolysis in the presence of both the chemical compound and the second chemical compound than in the presence of only the second chemical compound.

9. A process for determining whether a chemical compound is a human or rat galanin receptor (GALR2) agonist which comprises contacting cells transfected with DNA encoding and expressing on their cell surface the human or rat galanin receptor (GALR2), or a membrane preparation from such cells, with the compound under conditions permitting the activation of the human or rat galanin receptor (GALR2), and detecting an increase in human or rat galanin receptor (GALR2) activity, so as to thereby determine whether the compound is a human or rat galanin receptor (GALR2) agonist, wherein such cells prior to being transfected with such DNA do not normally express the human or rat galanin receptor (GALR2), and wherein the human galanin receptor (GALR2) has an amino acid sequence identical to that (a) shown in SEQ ID NO: 28, (b) expressed by COS-7 cells transfected with plasmid BO29 (ATCC Accession No. 97735) or (c) expressed by COS-7 cells transfected with plasmid BO39 (ATCC Accession No. 97851), and the rat galanin receptor (GALR2) has an amino acid sequence identical to that (a) shown in SEQ ID NO: 8 or (b) expressed by LM(tk−) cells, COS-7 cells or CHO cells transfected with (i) plasmid K985 (ATCC Accession No. 97426) or (ii) plasmid K1045 (ATCC Accession No. 97778).

10. A process for determining whether a chemical compound is a human or rat galanin receptor (GALR2) antagonist which comprises contacting cells transfected with DNA encoding and expressing on their cell surface the human or rat galanin receptor (GALR2), or a membrane preparation from such cells, with the compound in the presence of a known human or rat galanin receptor (GALR2) agonist, under conditions permitting the activation of the human or rat galanin receptor (GALR2), and detecting a decrease in human or rat galanin receptor (GALR2) activity, so as to thereby determine whether the compound is a human or rat galanin receptor (GALR2) antagonist, wherein such cells prior to being transfected with such DNA do not normally express the human or rat galanin receptor (GALR2), and wherein the human galanin receptor (GALR2) has an amino acid sequence identical to that (a) shown in SEQ ID NO: 28, (b) expressed by COS-7 cells transfected with plasmid BO29 (ATCC Accession No. 97735) or (c) expressed by COS-7 cells transfected with plasmid BO39 (ATCC Accession No. 97851), and the rat galanin receptor (GALR2) has an amino acid sequence identical to that (a) shown in SEQ ID NO: 8 or (b) expressed by LM(tk−) cells, COS-7 cells or CHO cells transfected with (i) plasmid K985 (ATCC Accession No. 97426) or (ii) plasmid K1045 (ATCC Accession No. 97778).

11. The process of claims 9 or 10, wherein activation of the human or rat galanin receptor (GALR2) is determined by a second messenger assay.

12. The process of claim 11, wherein the second messenger is arachidonic acid, intracellular calcium or a phosphoinositol lipid metabolite.

13. A method of obtaining a composition which comprises identifying a chemical compound by the process of any one of claims 1, 5, 9, or 10, recovering said compound free of any receptor, and admixing said compound with a pharmaceutically acceptable carrier.

14. The process of any one of claims 1, 5, 9, or 10, wherein the cells are insect cells.

15. The process of any one of claims 1, 5, 9, or 10, wherein the cells are mammalian cells.

16. The process of claim 15, wherein the mammalian cells are nonneuronal in origin.

17. The process of claim 15, wherein the nonneuronal cells are COS-7 cells, 293 human embryonic kidney cells, CHO cells, NIH-3T3 cells or LM(tk−) cells.

18. The process of claim 15, wherein the nonneuronal cells are LM(tk−) cells designated L-rGALR2-8 (ATCC Accession No. CRL-12074).

19. The process of claim 15, wherein the nonneuronal cells are LM(tk−) cells designated L-rGALR2I-4 (ATCC Accession No. CRL-12223).

20. The process of claim 15, wherein the nonneuronal cells are CHO cells designated C-rGALR2-79 (ATCC Accession No. CRL-12262).

21. A method of screening a plurality of chemical compounds not known to activate a human or rat galanin receptor (GALR2) to identify a compound which activates the human or rat galanin receptor (GALR2) which comprises:
  (a) contacting cells transfected with and expressing DNA encoding the human or rat galanin receptor (GALR2), or a membrane preparation from such cells, wherein such cells prior to being transfected with such DNA do not express the human or rat galanin receptor (GALR2), with the plurality of compounds not known to activate the human or rat galanin receptor (GALR2), under conditions permitting activation of the human or rat galanin receptor (GALR2);
  (b) determining whether the activity of the human or rat galanin receptor (GALR2) is increased in the presence of one or more of the compounds; and if so
  (c) separately determining whether the activation of the human or rat galanin receptor (GALR2) is increased by any compound included in the plurality of compounds, so as to thereby identify each compound which activates the human or rat galanin receptor (GALR2),
wherein the human galanin receptor (GALR2) has an amino acid sequence identical to that (a) shown in SEQ ID NO: 28, (b) expressed by COS-7 cells transfected with plasmid BO29 (ATCC Accession No. 97735) or (c) expressed by COS-7 cells transfected with plasmid BO39 (ATCC Accession No. 97851), and the rat galanin receptor (GALR2) has an amino acid sequence identical to that (a) shown in SEQ ID NO: 8 or (b) expressed by LM(tk−) cells, COS-7 cells or CHO cells transfected with (i) plasmid K985 (ATCC Accession No. 97426) or (ii) plasmid K1045 (ATCC Accession No. 97778).

22. A method of screening a plurality of chemical compounds not known to inhibit the activation of a human or rat galanin receptor (GALR2) to identify a compound which inhibits the activation of the human or rat galanin receptor (GALR2) which comprises:
  (a) contacting cells transfected with and expressing DNA encoding the human or rat galanin receptor (GALR2), or a membrane preparation from such cells, wherein such cells prior to being transfected with such DNA do not express the human or rat galanin receptor (GALR2), with the plurality of compounds in the presence of a known human or rat galanin receptor (GALR2) agonist, under conditions permitting activation of the human or rat galanin receptor (GALR2);

(b) determining whether the activation of the human or rat galanin receptor (GALR2) is reduced in the presence of the plurality of compounds, relative to the activation of the human or rat galanin receptor (GALR2) in the absence of the plurality of compounds; and if so (c) separately determining the inhibition of activation of the human or rat galanin receptor (GALR2) for each compound included in the plurality of compounds, so as to thereby identify each compound which inhibits the activation of the human or rat galanin receptor (GALR2), wherein the human galanin receptor (GALR2) has an amino acid sequence identical to that (a) shown in SEQ ID NO: 28, (b) expressed by COS-7 cells transfected with plasmid BO29 (ATCC Accession No. 97735) or (c) expressed by COS-7 cells transfected with plasmid BO39 (ATCC Accession No. 97851), and the rat galanin receptor (GALR2) has an amino acid sequence identical to that (a) shown in SEQ ID NO: 8 or (b) expressed by LM(tk−) cells, COS-7 cells or CHO cells transfected with (i) plasmid K985 (ATCC Accession No. 97426) or (ii) plasmid K1045 (ATCC Accession No. 97778).

23. The process of claims 21 or 22, wherein activation of the human or rat galanin receptor (GALR2) is determined by a second messenger assay.

24. The process of claim 23, wherein the second messenger is arachidonic acid, intracellular calcium or a phosphoinositol lipid metabolite.

25. A method of obtaining a composition which comprises identifying a chemical compound by the method of claims 21 or 22, recovering said compound free of any receptor, and admixing said compound with a pharmaceutically acceptable carrier.

26. The method of claims 21 or 22, wherein the cells are insect cells.

27. The method of claims 21 or 22, wherein the cells are mammalian cells.

28. The method of claim 27, wherein the mammalian cells are nonneuronal in origin.

29. The method of claim 27, wherein the nonneuronal cells are COS-7 cells, 293 human embryonic kidney cells, CHO cells, NIH-3T3 cells or LM(tk−) cells.

30. The method of claim 27, wherein the nonneuronal cells are LM(tk−) cells designated L-rGALR2-8 (ATCC Accession No. CRL-12074).

31. The method of claim 27, wherein the nonneuronal cells are LM(tk−) cells designated L-rGALR2I-4 (ATCC Accession No. CRL-12223).

32. The method of claim 27, wherein the nonneuronal cells are CHO cells designated C-rGALR2-79 (ATCC Accession No. CRL-12262).

* * * * *

SEQUENCE LISTING

```
<160> NUMBER OF SEQ ID NOS: 37

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
tgggcaacag cctagtgatc accg                                            24

<210> SEQ ID NO 2
<211> LENGTH: 24
<212> TYPE: DNA
<213> ORGANISM: Artificial Sequence
<220> FEATURE:
<223> OTHER INFORMATION: Primer
```

-continued

```
<400> SEQUENCE: 2
ctgctcccag cagaaggtct ggtt                                              24

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
cctcagtgaa gggaatggga gcga                                              24

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
ctcattgcaa acacggcact tgaaca                                            26

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
cttgcttgta cgccttccgg aagt                                              24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
gagaacttca tcacgctggt ggtg                                              24

<210> SEQ ID NO 7
<211> LENGTH: 1193
<212> TYPE: DNA
<213> ORGANISM: Rattus sp

<400> SEQUENCE: 7
caagacccgg acagctgcgg gagcggcgtc cactttggtg ataccatgaa tggctccggc       60
agccagggcg cggagaacac gagccaggaa ggcggtagcg gcggctggca gcctgaggcg      120
gtccttgtac ccctattttt cgcgctcatc ttcctcgtgg gcaccgtggg caacgcgctg      180
gtgctggcgg tgctgctgcg cggcggccag gcggtcagca ccaccaacct gttcatcctc      240
aacctgggcg tggccgacct gtgtttcatc ctgtgctgcg tgccttttca ggccaccatc      300 tacacctgg acgactgggt gttcggctcg ctgctctgca aggctgttca tttcctcatc      360
tttctcacta tgcacgccag cagcttcacg ctggccgcc tctccctgga caggtatctg      420
gccatccgct acccgctgca ctcccgagag ttgcgcacac ctcgaaacgc gctggccgcc      480
atcgggctca tctgggggct agcactgctc ttctccgggc cctacctgag ctactaccgt      540
```

-continued

```
cagtcgcagc tggccaacct gacagtatgc cacccagcat ggagcgcacc tcgacgtcga    600
gccatggacc tctgcacctt cgtctttagc tacctgctgc cagtgctagt cctcagtctg    660
acctatgcgc gtaccctgcg ctacctctgg cgcacagtcg acccggtgac tgcaggctca    720
ggttcccagc gcgccaaacg caaggtgaca cggatgatca tcatcgtggc ggtgcttttc    780
tgcctctgtt ggatgcccca ccacgcgctt atcctctgcg tgtggtttgg tcgcttcccg    840
ctcacgcgtg ccacttacgc gttgcgcatc ctttcacacc tagtttccta tgccaactcc    900
tgtgtcaacc ccatcgttta cgctctggtc tccaagcatt ccgtaaagg tttccgcaaa     960 atctgcgcgg gcctgctgcg ccctgccccg aggcgagctt cgggccgagt gagcatcctg   1020
gcgcctggga accatagtgg cagcatgctg aacaggaat ccacagacct gacacaggtg    1080
agcgaggcag ccgggcccct tgtcccacca cccgcacttc ccaactgcac agcctcgagt   1140
agaaccctgg atccggcttg ttaaaggacc aaagggcatc taacagcttc tag          1193
```

<210> SEQ ID NO 8
<211> LENGTH: 372
<212> TYPE: PRT
<213> ORGANISM: Rattus sp

<400> SEQUENCE: 8

```
Met Asn Gly Ser Gly Ser Gln Gly Ala Glu Asn Thr Ser Gln Glu Gly
  1               5                  10                  15

Gly Ser Gly Gly Trp Gln Pro Glu Ala Val Leu Val Pro Leu Phe Phe
                 20                  25                  30

Ala Leu Ile Phe Leu Val Gly Thr Val Gly Asn Ala Leu Val Leu Ala
             35                  40                  45

Val Leu Leu Arg Gly Gly Gln Ala Val Ser Thr Thr Asn Leu Phe Ile
         50                  55                  60

Leu Asn Leu Gly Val Ala Asp Leu Cys Phe Ile Leu Cys Cys Val Pro
 65                  70                  75                  80

Phe Gln Ala Thr Ile Tyr Thr Leu Asp Asp Trp Val Phe Gly Ser Leu
                 85                  90                  95

Leu Cys Lys Ala Val His Phe Leu Ile Phe Leu Thr Met His Ala Ser
                100                 105                 110

Ser Phe Thr Leu Ala Ala Val Ser Leu Asp Arg Tyr Leu Ala Ile Arg
            115                 120                 125

Tyr Pro Leu His Ser Arg Glu Leu Arg Thr Pro Arg Asn Ala Leu Ala
        130                 135                 140

Ala Ile Gly Leu Ile Trp Gly Leu Ala Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Leu Cys Thr Phe
            180                 185                 190

Val Phe Ser Tyr Leu Pro Val Leu Val Leu Ser Leu Thr Tyr Ala
            195                 200                 205

Arg Thr Leu Arg Tyr Leu Trp Arg Thr Val Asp Pro Val Thr Ala Gly
        210                 215                 220

Ser Gly Ser Gln Arg Ala Lys Arg Lys Val Thr Arg Met Ile Ile Ile
225                 230                 235                 240

Val Ala Val Leu Phe Cys Leu Cys Trp Met Pro His His Ala Leu Ile
                245                 250                 255

Leu Cys Val Trp Phe Gly Arg Phe Pro Leu Thr Arg Ala Thr Tyr Ala
```

```
                     260                 265                 270
Leu Arg Ile Leu Ser His Leu Val Ser Tyr Ala Asn Ser Cys Val Asn
            275                 280                 285

Pro Ile Val Tyr Ala Leu Val Ser Lys His Phe Arg Lys Gly Phe Arg
        290                 295                 300

Lys Ile Cys Ala Gly Leu Leu Arg Pro Ala Pro Arg Arg Ala Ser Gly
305                 310                 315                 320

Arg Val Ser Ile Leu Ala Pro Gly Asn His Ser Gly Ser Met Leu Glu
                325                 330                 335

Gln Glu Ser Thr Asp Leu Thr Gln Val Ser Glu Ala Ala Gly Pro Leu
            340                 345                 350

Val Pro Pro Pro Ala Leu Pro Asn Cys Thr Ala Ser Ser Arg Thr Leu
        355                 360                 365

Asp Pro Ala Cys
    370

<210> SEQ ID NO 9
<211> LENGTH: 2200
<212> TYPE: DNA
<213> ORGANISM: Rattus sp

<400> SEQUENCE: 9
caagacccgg acagctgcgg gagcggcgtc cactttggtg ataccatgaa tggctccggc      60
agccagggcg cggagaacac gagccaggaa ggcggtagcg gcggctggca gcctgaggcg     120
gtccttgtac ccctattttt cgcgctcatc ttcctcgtgg gcaccgtggg caacgcgctg     180
gtgctggcgg tgctgctgcg cggcggccag gcggtcagca ccaccaacct gttcatcctc     240
aacctgggcg tggccgacct gtgtttcatc ctgtgctgcg tgccttttcca ggccaccatc     300 tacaccctgg acgactgggt gttcggctcg ctgctctgca aggctgttca tttcctcatc     360
tttctcacta tgcacgccag cagcttcacg ctggccgccg tctccctgga caggtgagtg     420
aacatcggag aactattgta tctgagatag gggcttgggc tggagtcact acacagggga     480
tccagaaggc atgagcagaa tgggcgagaa cactgaaatt acaaagtggc ctgaggccgt     540
gaaacgcaag ggggagggag attaagactc agtgactgag agtgtctaag tcgatgggag     600
aaatcgggtc tctgggggtcc tcgcattatt actgcttgag ttaaatgtct ctgtgaaaca     660
ttgcagttct caggccagag ttggcaggaa aagtaactcg ccagtgttca gatgctgttt     720
gagagctgca gagaagcatc tgcttcttag caccaagctc agcacctggg gcgttgtccg     780
gcgccttagg cttaggactg ggctgtgctg tgttaagacc catgctcaag tccaacggag     840
tgtaagcgag ggctcctagc tgacacccag agccctccag gccaaggctc ccctcaccga     900
gatgccagcg gttttatgct ccttccatag gtaaaggacc cagaaagaaa catccagtat     960
gcccggaggg atcttgactg gaaaagactg aatcctggtc tggtgacctt agttccctgc    1020
cctttcacat cacttggaca ttcccacaga agagcggtga agaggcggtg gtccttattc    1080
tcctctggtt tccactgagt gcaacatgtg cgtcctgagt acgctggagg gactcacaaa    1140
atttcagctt tctttaggag tttccttgct gtagtttgac ccaagtcttc tccaggtttc    1200
tgtcagaacc tcaggcatga gggatctgcc tcccctggtt gtcaccagag ataacaatc     1260 actgccccca gaaatccaga cagattctac aactttttagt cttcggtgtt ttgggggtgc    1320
cccttcacgt ggagtaggtc ggtggccaca ttcccaggag tgacaatagc ctagcagtga    1380
atcctctcgc ttagctgatg ccccccccact gtccccacag gtatctggcc atccgctacc    1440
```

```
cgctgcactc ccgagagttg cgcacacctc gaaacgcgct ggccgccatc gggctcatct      1500
gggggctagc actgctcttc tccgggccct acctgagcta ctaccgtcag tcgcagctgg      1560
ccaacctgac agtatgccac ccagcatgga gcgcacctcg acgtcgagcc atggacctct      1620
gcaccttcgt ctttagctac ctgctgccag tgctagtcct cagtctgacc tatgcgcgta      1680
ccctgcgcta cctctggcgc acagtcgacc cggtgactgc aggctcaggt tcccagcgcg      1740
ccaaacgcaa ggtgacacgg atgatcatca tcgtggcggt gcttttctgc ctctgttgga      1800
tgccccacca cgcgcttatc ctctgcgtgt ggtttggtcg cttcccgctc acgcgtgcca      1860
cttacgcgtt gcgcatcctt tcacacctag tttcctatgc caactcctgt gtcaacccca      1920
tcgtttacgc tctggtctcc aagcatttcc gtaaaggttt ccgcaaaatc tgcgcgggcc      1980
tgctgcgccc tgccccgagg cgagcttcgg gccgagtgag catcctggcg cctgggaacc      2040
atagtggcag catgctggaa caggaatcca cagacctgac acaggtgagc gaggcagccg      2100
ggccccttgt cccaccaccc gcacttccca actgcacagc ctcgagtaga accctggatc      2160
cggcttgtta aaggaccaaa gggcatctaa cagcttctag                            2200
```

<210> SEQ ID NO 10
<211> LENGTH: 26
<212> TYPE: DNA
<213> ORGANISM: artificial sequence
<220> FEATURE:
<223> OTHER INFORMATION: Primer

<400> SEQUENCE: 10
caaggctgtt catttcctca tctttc                                             26

<210> SEQ ID NO 11
<211> LENGTH: 25
<212> TYPE: DNA
<213> ORGANISM: artificial sequence
<220> FEATURE:
<223> OTHER INFORMATION: Primer

<400> SEQUENCE: 11
ttggagacca gagcgtaaac gatgg                                              25

<210> SEQ ID NO 12
<211> LENGTH: 45
<212> TYPE: DNA
<213> ORGANISM: artificial sequence
<220> FEATURE:
<223> OTHER INFORMATION: Primer/Probe

<400> SEQUENCE: 12
agtcgacccg gtgactgcag gctcaggttc ccagcgcgcc aaacg                        45

<210> SEQ ID NO 13
<211> LENGTH: 23
<212> TYPE: DNA
<213> ORGANISM: artificial sequence
<220> FEATURE:
<223> OTHER INFORMATION: Primer/Probe

<400> SEQUENCE: 13
ccctacctga gctactaccg tca                                                23

<210> SEQ ID NO 14
<211> LENGTH: 24
<212> TYPE: DNA
<213> ORGANISM: artificial sequence

```
<220> FEATURE:
<223> OTHER INFORMATION: Primer/Probe

<400> SEQUENCE: 14
accaaaccac acgcagagga taag                                              24

<210> SEQ ID NO 15
<211> LENGTH: 26
<212> TYPE: DNA
<213> ORGANISM: artificial sequence
<220> FEATURE:
<223> OTHER INFORMATION: Primer/Probe

<400> SEQUENCE: 15
ccacgatgag gatcatgcgt gtcacc                                            26

<210> SEQ ID NO 16
<211> LENGTH: 26
<212> TYPE: DNA
<213> ORGANISM: artificial sequence
<220> FEATURE:
<223> OTHER INFORMATION: Primer/Probe

<400> SEQUENCE: 16
taggtcaggc cgagaaccag cacagg                                            26

<210> SEQ ID NO 17
<211> LENGTH: 24
<212> TYPE: DNA
<213> ORGANISM: artificial sequence
<220> FEATURE:
<223> OTHER INFORMATION: Primer/Probe

<400> SEQUENCE: 17
caggtagctg aagacgaagg tgca                                              24

<210> SEQ ID NO 18
<211> LENGTH: 25
<212> TYPE: DNA
<213> ORGANISM: artificial sequence
<220> FEATURE:
<223> OTHER INFORMATION: Primer/Probe

<400> SEQUENCE: 18
ctgcaccttc gtcttcagct acctg                                             25

<210> SEQ ID NO 19
<211> LENGTH: 26
<212> TYPE: DNA
<213> ORGANISM: artificial sequence
<220> FEATURE:
<223> OTHER INFORMATION: Primer/Probe

<400> SEQUENCE: 19
cctgtgctgg ttctcggcct gaccta                                            26

<210> SEQ ID NO 20
<211> LENGTH: 26
<212> TYPE: DNA
<213> ORGANISM: artificial sequence
<220> FEATURE:
<223> OTHER INFORMATION: Primer/Probe

<400> SEQUENCE: 20
tatctggcca tccgctaccc gctgca                                            26
```

<210> SEQ ID NO 21
<211> LENGTH: 45
<212> TYPE: DNA
<213> ORGANISM: artificial sequence
<220> FEATURE:
<223> OTHER INFORMATION: Primer/Probe

<400> SEQUENCE: 21
ttgcgctacc tctggcgcgc cgtcgacccg gtggccgcgg gctcg                45

<210> SEQ ID NO 22
<211> LENGTH: 25
<212> TYPE: DNA
<213> ORGANISM: artificial sequence
<220> FEATURE:
<223> OTHER INFORMATION: Primer/Probe

<400> SEQUENCE: 22
ccaacaatga ctccaactct gtgac                                      25

<210> SEQ ID NO 23
<211> LENGTH: 25
<212> TYPE: DNA
<213> ORGANISM: artificial sequence
<220> FEATURE:
<223> OTHER INFORMATION: Primer/Probe

<400> SEQUENCE: 23
aggcgcagaa ctggtaggta tggaa                                      25

<210> SEQ ID NO 24
<211> LENGTH: 25
<212> TYPE: DNA
<213> ORGANISM: artificial sequence
<220> FEATURE:
<223> OTHER INFORMATION: Primer/Probe

<400> SEQUENCE: 24
aagcttctag agatccctcg acctc                                      25

<210> SEQ ID NO 25
<211> LENGTH: 28
<212> TYPE: DNA
<213> ORGANISM: artificial sequence
<220> FEATURE:
<223> OTHER INFORMATION: Primer

<400> SEQUENCE: 25
acggaattcg acatgaatgg ctccggca                                   28

<210> SEQ ID NO 26
<211> LENGTH: 34
<212> TYPE: DNA
<213> ORGANISM: artificial sequence
<220> FEATURE:
<223> OTHER INFORMATION: Primer

<400> SEQUENCE: 26
gctctagagc ccctttggtc ctttaacaag ccgg                            34

<210> SEQ ID NO 27
<211> LENGTH: 1365
<212> TYPE: DNA
<213> ORGANISM: homo sapiens

<400> SEQUENCE: 27

```
agtcgcacta ggagttgcag cggccgcagc cccgggagct tcccgctcgc ggagacccag      60
acggctgcag gagcccgggc agcctcgggg tcagcggcac catgaacgtc tcgggctgcc     120
caggggccgg gaacgcgagc caggcgggcg gcggggagg ctggcacccc gaggcggtca     180
tcgtgcccct gctcttcgcg ctcatcttcc tcgtgggcac cgtgggcaac acgctggtgc     240
tggcggtgct gctgcgcggc ggccaggcgg tcagcactac caacctgttc atccttaacc     300
tgggcgtggc cgacctgtgt ttcatcctgt gctgcgtgcc cttccaggcc accatctaca     360
ccctggacgg ctgggtgttc ggctcgctgc tgtgcaaggc ggtgcacttc ctcatcttcc     420
tcaccatgca cgccagcagc ttcacgctgg ccgccgtctc cctggacagg tatctggcca     480
tccgctaccc gctgcactcc cgcgagctgc gcacgcctcg aaacgcgctg gcagccatcg     540
ggctcatctg ggggctgtcg ctgctcttct ccgggcccta cctgagctac taccgccagt     600
cgcagctggc caacctgacc gtgtgccatc ccgtggag cgcccctcgc cgccgcgcca     660
tggacatctg caccttcgtc ttcagctacc tgcttcctgt gctggttctc ggcctgacct     720
acgcgcgcac cttgcgctac ctctggcgcg ccgtcgaccc ggtggccgcg ggctcgggtg     780
cccggcgcgc caagcgcaag gtgacacgca tgatcctcat cgtggccgcg ctcttctgcc     840
tctgctggat gccccaccac cgcgctcatcc tctgcgtgtg gttcggccag ttcccgctca     900
cgcgcgccac ttatgcgctt cgcatcctct cgcacctggt ctcctacgcc aactcctgcg     960
tcaaccccat cgtttacgcg ctggtctcca agcacttccg caaaggcttc cgcacgatct    1020
gcgcgggcct gctgggccgt gccccaggcc gagcctcggg ccgtgtgtgc gctgccgcgc    1080 ggggcacccca cagtggcagc gtgttggagc gcgagtccag cgacctgttg cacatgagcg    1140
aggcggcggg ggcccttcgt ccctgccccg gcgcttccca gccatgcatc ctcgagccct    1200
gtcctggccc gtcctggcag ggcccaaagg caggcgacag catcctgacg gttgatgtgg    1260
cctgaaagca cttagcgggc gcgctgggat gtcacagagt tggagtcatt gttggggac    1320 cgtggggaga gctttgcctg ttaataaaac gcacaaacca tttca                      1365
```

<210> SEQ ID NO 28
<211> LENGTH: 387
<212> TYPE: PRT
<213> ORGANISM: homo sapiens

<400> SEQUENCE: 28

```
Met Asn Val Ser Gly Cys Pro Gly Ala Gly Asn Ala Ser Gln Ala Gly
1               5                  10                  15

Gly Gly Gly Gly Trp His Pro Glu Ala Val Ile Val Pro Leu Leu Phe
            20                  25                  30

Ala Leu Ile Phe Leu Val Gly Thr Val Gly Asn Thr Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125
```

Tyr Pro Leu His Ser Arg Glu Leu Arg Thr Pro Arg Asn Ala Leu Ala
    130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Ala Met Asp Ile Cys Thr Phe
            180                 185                 190

Val Phe Ser Tyr Leu Leu Pro Val Leu Val Leu Gly Leu Thr Tyr Ala
    195                 200                 205

Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
    275                 280                 285

Pro Ile Val Tyr Ala Leu Val Ser Lys His Phe Arg Lys Gly Phe Arg
    290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Ile Leu Glu Pro Cys Pro
    355                 360                 365

Gly Pro Ser Trp Gln Gly Pro Lys Ala Gly Asp Ser Ile Leu Thr Val
    370                 375                 380

Asp Val Ala
385

<210> SEQ ID NO 29
<211> LENGTH: 1384
<212> TYPE: DNA
<213> ORGANISM: homo sapiens

<400> SEQUENCE: 29
gtgagccagc gccttggcct ccctgggaga tgggcatcca cgcggggat ggagcgggag      60 gcgggactgg ggaccaagaa gggacgcgca gagtgggaca ggacactaag aaggcagtgg     120
aagacaagcg ggcgcggagg aggaaaaaga ggaataagaa tggggaccg tgtgtccct      180 cggttagatg cgtcctgggg cctggaagcc tggagaatgt ggctctccag cgccgcccgt    240
gcctgacaac gcgcagcgtt tcccagtacg acgcgtttgt gcgcgttcat ctcgcttgag    300
cttaatgccc tccgtgaggg tgggatagga caaagtgccc aatatacaga agagttgagt    360
tcctaagtaa ctcgctcaga gtcgccagcc agggatcggg tgcgtgaagt gaccgtctgt    420
ctcctgcagc caacttcagg cgcctccact gcgctcgcct ccaagccacg gtttggttgg    480
ttggtgcagc tggctcaggt ccaggctgtg gatcttgggt cctttgcaag gatccactcc    540
ggagtcccag cgagcgtgcc taaaggtccc tagctcagtc ccagcccact ctgcctctcg    600

-continued

```
cctccaaaca aaacaaaaca aaataaaatc caaaacaagt cggggccggg agaggagcgt    660
gccctggggt tcttcctccc cagccagagg agagcgagag acgcacattc gggagagcgc    720
gggactcagg tggagcttga aaggacactg ggatggttcc tggggaggaa atccgggtat    780
ttcccctctc catcctctgg aaaaacagag aggcgaggcc agactgcccc cacacctcct    840
gtagccactg agcgcgaagt gcgttggttc cgagcgcgct ggtgggatcc acaaagctcg    900
cattctctca ggaatcccct gagaaattaa ctgtcccttg cccaacatgt cttctccagg    960
ctgtctgcta gagcctcagg cgcctccgcc ctccctcccg cggcaccgtc accagtgggt   1020
agtcacagcc tcccggagcc catagccggt tctccaacct ttagtcttca gtggctttgg   1080
ggtgccctct cagtggagac tgtggttgca gtccccgggg gcagcgggag aatggcttga   1140
aggcacacct ttcctgctgc cgggcccgcc ccatttccag gctccgctga gtgtctggga   1200
cacgctggga ggcccccacc tccgccctca cgccgagcct caccccccacc tcctctgtgt   1260
gcggtgtaac catgcgctaa ggaccttcct cgagagcagc cttgggaccg aggtgcaggg   1320
gtcgcggccc tccagcatga atgtgcccgc tcagccgacg tctcccttcc cggtctgacc   1380
gcag                                                                1384
```

<210> SEQ ID NO 30
<211> LENGTH: 346
<212> TYPE: PRT
<213> ORGANISM: Rattus sp

<400> SEQUENCE: 30

```
Met Glu Leu Ala Pro Val Asn Leu Ser Glu Gly Asn Gly Ser Asp Pro
1               5                   10                  15

Glu Pro Pro Ala Glu Pro Arg Pro Leu Phe Gly Ile Gly Val Glu Asn
            20                  25                  30

Phe Ile Thr Leu Val Val Phe Gly Leu Ile Phe Ala Met Gly Val Leu
        35                  40                  45

Gly Asn Ser Leu Val Ile Thr Val Leu Ala Arg Ser Lys Pro Gly Lys
    50                  55                  60

Pro Arg Ser Thr Thr Asn Leu Phe Ile Leu Asn Leu Ser Ile Ala Asp
65                  70                  75                  80

Leu Ala Tyr Leu Leu Phe Cys Ile Pro Phe Gln Ala Thr Val Tyr Ala
                85                  90                  95

Leu Pro Thr Trp Val Leu Gly Ala Phe Ile Cys Lys Phe Ile His Tyr
            100                 105                 110

Phe Phe Thr Val Ser Met Leu Val Ser Ile Phe Thr Leu Ala Ala Met
        115                 120                 125

Ser Val Asp Arg Tyr Val Ala Ile Val His Ser Arg Arg Ser Ser Ser
    130                 135                 140

Leu Arg Val Ser Arg Asn Ala Leu Leu Gly Val Gly Phe Ile Trp Ala
145                 150                 155                 160

Leu Ser Ile Ala Met Ala Ser Pro Val Ala Tyr Tyr Gln Arg Leu Phe
                165                 170                 175

His Arg Asp Ser Asn Gln Thr Phe Cys Trp Glu His Trp Pro Asn Gln
            180                 185                 190

Leu His Lys Lys Ala Tyr Val Val Cys Thr Phe Val Phe Gly Tyr Leu
        195                 200                 205

Leu Pro Leu Leu Leu Ile Cys Phe Cys Tyr Ala Lys Val Leu Asn His
    210                 215                 220
```

```
Leu His Lys Lys Leu Lys Asn Met Ser Lys Lys Ser Glu Ala Ser Lys
225                 230                 235                 240

Lys Lys Thr Ala Gln Thr Val Leu Val Val Val Val Phe Gly Ile
            245                 250                 255

Ser Trp Leu Pro His His Val Ile His Leu Trp Ala Glu Phe Gly Ala
                260                 265                 270

Phe Pro Leu Thr Pro Ala Ser Phe Phe Phe Arg Ile Thr Ala His Cys
            275                 280                 285

Leu Ala Tyr Ser Asn Ser Ser Val Asn Pro Ile Ile Tyr Ala Phe Leu
            290                 295                 300

Ser Glu Asn Phe Arg Lys Ala Tyr Lys Gln Val Phe Lys Cys Arg Val
305                 310                 315                 320

Cys Asn Glu Ser Pro His Gly Asp Ala Lys Glu Lys Asn Arg Ile Asp
                325                 330                 335

Thr Pro Pro Ser Thr Asn Cys Thr His Val
            340                 345
```

<210> SEQ ID NO 31
<211> LENGTH: 40
<212> TYPE: DNA
<213> ORGANISM: artificial sequence
<220> FEATURE:
<223> OTHER INFORMATION: Primer

<400> SEQUENCE: 31
tcgtaataga agcttggcca catcaaccgt caggatgctg          40

<210> SEQ ID NO 32
<211> LENGTH: 40
<212> TYPE: DNA
<213> ORGANISM: artificial sequence
<220> FEATURE:
<223> OTHER INFORMATION: Primer

<400> SEQUENCE: 32
tatcgatagg aattcagcgg caccatgaac gtctcgggct          40

<210> SEQ ID NO 33
<211> LENGTH: 41
<212> TYPE: DNA
<213> ORGANISM: artificial sequence
<220> FEATURE:
<223> OTHER INFORMATION: Primer

<400> SEQUENCE: 33
atcgtttacg cgctggtctc caagcacttc cgcaaaggct t          41

<210> SEQ ID NO 34
<211> LENGTH: 37
<212> TYPE: DNA
<213> ORGANISM: artificial sequence
<220> FEATURE:
<223> OTHER INFORMATION: Primer

<400> SEQUENCE: 34
cgcggatcca ttatgtctgc actccgaagg aaatttg          37

<210> SEQ ID NO 35
<211> LENGTH: 38
<212> TYPE: DNA
<213> ORGANISM: artificial sequence
<220> FEATURE:
<223> OTHER INFORMATION: Primer

```
<400> SEQUENCE: 35
cgcgaattct tatgtgaagc gatcagagtt cattttc                                    38

<210> SEQ ID NO 36
<211> LENGTH: 34
<212> TYPE: DNA
<213> ORGANISM: artificial sequence
<220> FEATURE:
<223> OTHER INFORMATION: Primer

<400> SEQUENCE: 36
gcgggatccg ctatggctgg tgattctagg aatg                                       34

<210> SEQ ID NO 37
<211> LENGTH: 29
<212> TYPE: DNA
<213> ORGANISM: artificial sequence
<220> FEATURE:
<223> OTHER INFORMATION: Primer

<400> SEQUENCE: 37
ccggaattcc cctcacaccg agcccctgg                                             29
```